US012416015B2

(12) United States Patent
Roy et al.

(10) Patent No.: US 12,416,015 B2
(45) Date of Patent: Sep. 16, 2025

(54) MULTIPLEX PRODUCTION AND BARCODING OF GENETICALLY ENGINEERED CELLS

(71) Applicants: The Board of Trustees of the Leland Stanford Junior University, Palo Alto, CA (US); Brandeis University, Waltham, MA (US)

(72) Inventors: Kevin Roy, Mountain View, CA (US); Justin D. Smith, Redwood City, CA (US); Robert P. St. Onge, San Francisco, CA (US); Lars M. Steinmetz, Stanford, CA (US); James E. Haber, Waltham, MA (US)

(73) Assignees: THE BOARD OF TRUSTEES OF THE LELAND STANFORD JUNIOR UNIVERSITY, Palo Alto, CA (US); BRANDEIS UNIVERSITY, Waltham, MA (US)

( * ) Notice: Subject to any disclaimer, the term of this patent is extended or adjusted under 35 U.S.C. 154(b) by 403 days.

(21) Appl. No.: 16/646,999

(22) PCT Filed: Sep. 14, 2018

(86) PCT No.: PCT/US2018/051240
§ 371 (c)(1),
(2) Date: Mar. 12, 2020

(87) PCT Pub. No.: WO2019/055878
PCT Pub. Date: Mar. 21, 2019

(65) Prior Publication Data
US 2020/0270632 A1 Aug. 27, 2020

Related U.S. Application Data

(60) Provisional application No. 62/559,493, filed on Sep. 15, 2017.

(51) Int. Cl.
*C12N 15/85* (2006.01)
*C12N 9/22* (2006.01)
*C12N 15/10* (2006.01)
*C12N 15/113* (2010.01)
*C12N 15/81* (2006.01)

(52) U.S. Cl.
CPC .............. *C12N 15/85* (2013.01); *C12N 9/22* (2013.01); *C12N 15/1082* (2013.01); *C12N 15/113* (2013.01); *C12N 15/81* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | |
|---|---|---|
| 4,415,732 A | 11/1983 | Caruthers et al. |
| 4,458,066 A | 7/1984 | Caruthers et al. |
| 4,816,567 A | 3/1989 | Cabilly et al. |
| 5,122,458 A | 6/1992 | Post et al. |
| 5,135,855 A | 8/1992 | Moss et al. |
| 5,139,941 A | 8/1992 | Muzyczka et al. |
| 5,168,062 A | 12/1992 | Stinski |
| 5,173,414 A | 12/1992 | Lebkowski et al. |
| 5,219,740 A | 6/1993 | Miller et al. |
| 5,385,839 A | 1/1995 | Stinski |
| 5,676,950 A | 10/1997 | Small et al. |

(Continued)

FOREIGN PATENT DOCUMENTS

| | | |
|---|---|---|
| CN | 106133138 A | 11/2016 |
| DE | 10329454 A1 | 1/2005 |

(Continued)

OTHER PUBLICATIONS

Shan, Targeted genome modification of crop plants using a CRISPR-Cas system, Nature Biotechnology, vol. 31, No. 8, Aug. 2013 (Year: 2013).*
Gupta, Expanding the genetic editing tool kit: ZFNs, TALENs, and CRISPR-Cas9, The Journal of Clinical Investigation, 2014; 124(10) (Year: 2014).*
Nagasaki, Enhanced nuclear import and transfection efficiency of plasmid DNA using streptavidin-fused importin-Beta, Journal of Controlled Release, 103 (2005), pp. 199-207 (Year: 2005).*
Li, Jin, et al. "Regulation of budding yeast mating-type switching donor preference by the FHA domain of Fkh1." PLoS genetics 8.4 (2012): e1002630. (Year: 2012).*
"DIY Bacterial Gene Engineering Crispr Kit." The ODIN, 2017, www.the-odin.com/diy-crispr-kit/. Accessed Feb. 12, 2024. (Year: 2017).*

(Continued)

*Primary Examiner* — Weihua Fan
*Assistant Examiner* — Brian James Sullivan
(74) *Attorney, Agent, or Firm* — Mintz, Levin, Cohn, Ferris, Glovsky & Popeo, P.C.

(57) ABSTRACT

The present disclosure relates to multiplex production and phenotyping of genetically engineered cells using RNA-guided nucleases and genomic barcoding. In particular, high-throughput multiplex genome editing is achieved utilizing a system that facilitates precise genome editing at desired target chromosomal loci by homology directed repair. Integration of guide RNA and donor DNA sequences as a genomic barcode at a separate chromosomal locus allows identification, isolation, and massively-parallel validation of individual variants from a pool of transformants. Strains can be arrayed according to their precise genetic modifications, as specified by donor DNA incorporation in heterologous or native genes. The present disclosure further relates to a method of editing codons outside of canonical guide RNA recognition regions, which enables complete saturation mutagenesis of protein-coding genes, a marker-based internal cloning method, which removes background due to oligonucleotide synthesis errors and incomplete vector backbone cleavage, and a method of enhancing homology directed repair by active donor recruitment.

15 Claims, 33 Drawing Sheets

(56) References Cited

U.S. PATENT DOCUMENTS

| | | | |
|---|---|---|---|
| 5,789,245 | A | 8/1998 | Dubensky et al. |
| 5,831,005 | A | 11/1998 | Zuckerman et al. |
| 5,840,051 | A | 11/1998 | Towsley |
| 5,843,723 | A | 12/1998 | Dubensky et al. |
| 5,844,107 | A | 12/1998 | Hanson et al. |
| 5,877,278 | A | 3/1999 | Zuckermann et al. |
| 5,877,302 | A | 3/1999 | Hanson et al. |
| 5,972,900 | A | 10/1999 | Ferkol et al. |
| 5,972,901 | A | 10/1999 | Ferkol et al. |
| 5,977,301 | A | 11/1999 | Zuckerman et al. |
| 6,008,336 | A | 12/1999 | Hanson et al. |
| 6,077,835 | A | 6/2000 | Hanson et al. |
| 6,200,801 | B1 | 3/2001 | Ferkol et al. |
| 2002/0150626 | A1 | 10/2002 | Kohane et al. |
| 2003/0032615 | A1 | 2/2003 | Felgner et al. |
| 2003/0203865 | A1 | 10/2003 | Harvie et al. |
| 2004/0048787 | A1 | 3/2004 | Cooper et al. |
| 2004/0133138 | A1 | 7/2004 | Modglin |
| 2010/0137143 | A1 | 6/2010 | Rothberg et al. |
| 2010/0304982 | A1 | 12/2010 | Hinz et al. |
| 2011/0105971 | A1 | 5/2011 | Ingimundarson et al. |
| 2015/0031132 | A1 | 1/2015 | Church et al. |
| 2016/0122748 | A1 | 5/2016 | St. onge et al. |
| 2016/0228279 | A1 | 8/2016 | Modglin et al. |
| 2017/0058298 | A1 | 3/2017 | Kennedy et al. |
| 2017/0233765 | A1* | 8/2017 | Kay ............... C12N 9/22 435/462 |
| 2019/0085356 | A1 | 3/2019 | Xia et al. |

FOREIGN PATENT DOCUMENTS

| | | | | |
|---|---|---|---|---|
| EP | 3024964 | A2 | 6/2016 | |
| GB | 2276169 | A | 9/1994 | |
| WO | 8903429 | A1 | 4/1989 | |
| WO | 9112882 | A1 | 9/1991 | |
| WO | 9201070 | A1 | 1/1992 | |
| WO | 9203545 | A1 | 3/1992 | |
| WO | 9303769 | A1 | 3/1993 | |
| WO | 9426911 | A1 | 11/1994 | |
| WO | 9507995 | A2 | 3/1995 | |
| WO | 9617072 | A2 | 6/1996 | |
| WO | 0061772 | A2 | 10/2000 | |
| WO | 0071096 | A2 | 11/2000 | |
| WO | 0181609 | A2 | 11/2001 | |
| WO | 02080982 | A2 | 10/2002 | |
| WO | 02099035 | A2 | 12/2002 | |
| WO | 2015013583 | A2 | 1/2015 | |
| WO | 2015095804 | A1 | 6/2015 | |
| WO | 2016183448 | A1 | 11/2016 | |
| WO | WO-2016176404 | A1 * | 11/2016 | ........... C12N 15/102 |
| WO | WO-2017070056 | A1 * | 4/2017 | ............. C12N 15/88 |
| WO | 2017092201 | A1 | 6/2017 | |
| WO | 2017223538 | A1 | 12/2017 | |
| WO | 2019051240 | A1 | 3/2019 | |

OTHER PUBLICATIONS

Bolukbasi, Mehmet Fatih, et al. "DNA-binding-domain fusions enhance the targeting range and precision of Cas9." Nature methods 12.12 (2015): 1150-1156. (Year: 2015).*

Bonilla, Braulio, et al. "RAD51 gene family structure and function." Annual review of genetics 54 (2020): 25-46. (Year: 2020).*

Tarantola, A. (Jun. 30, 2016). I played god with the Odin's DIY CRISPR kit. Engadget. https://www.engadget.com/2016-06-30-i-played-god-with-the-odins-diy-crispr-kit.html (Year: 2016).*

Lee, Kunwoo, et al. "Synthetically modified guide RNA and donor DNA are a versatile platform for CRISPR-Cas9 engineering." elife 6 (2017): e25312. (Year: 2017).*

Schumann, Kathrin, et al. "Generation of knock-in primary human T cells using Cas9 ribonucleoproteins." Proceedings of the National Academy of Sciences 112.33 (2015): 10437-10442. (Year: 2015).*

Dou, Hong, Sankar Mitra, and Tapas K. Hazra. "Repair of oxidized bases in DNA bubble structures by human DNA glycosylases NEIL1 and NEIL2." Journal of Biological Chemistry 278.50 (2003): 49679-49684. (Year: 2003).*

"DEF1 DNA Damage-Responsive RNA Polymerase-Degradation Factor Def1 [Saccharomyces cerevisiae S288C]—Gene—NCBI." National Center for Biotechnology Information, U.S. National Library of Medicine, Feb. 4, 2024, www.ncbi.nlm.nih.gov/gene/ 853811. (Year: 2024).*

"TPA: DNA Damage-Responsive RNA Polymerase-Degradation Factor DEF1 [SAC—Protein—NCBI." National Center for Biotechnology Information, U.S. National Library of Medicine, Jan. 23, 2024, www.ncbi.nlm.nih.gov/protein/285813206. (Year: 2024).*

Wang, Baosheng, et al. "Maize defensin ZmDEF1 is involved in plant response to fungal phytopathogens." African Journal of Biotechnology 10.72 (2011): 16128-16137. (Year: 2011).*

Ma, Ming, et al. "Efficient generation of mice carrying homozygous double-floxp alleles using the Cas9-Avidin/Biotin-donor DNA system." Cell Research 27.4 (2017): 578-581. (Year: 2017).*

Bao et al. (May 15, 2015) "Homology-Integrated CRISPR-Cas (HI-CRISPR) System for One-Step Multigene Disruption in Saccharomyces cerevisiae", ACS Synthetic Biology, 4(5):585-594.

Baranick et al. (Mar. 25, 2008) "Splicing Mediates the Activity of Four Putative Cellular Internal Ribosome Entry Sites", Proceedings of the National Academy of Sciences of the United States of America, 105(12):4733-4738.

Beaucage et al. (Mar. 20, 1992) "Advances in the Synthesis of Oligonucleotides by the Phosphoramidite Approach", Tetrahedron, 48(12):2223-2311.

Bentley et al. (Nov. 6, 2008) "Accurate Whole Human Genome Sequencing Using Reversible Terminator Chemistry", Nature, 456(7218):53-59.

Benvenisty et al. (Dec. 1986) "Direct Introduction of Genes into Rats and Expression of the Genes", Proceedings of the National Academy of Sciences of the United States of America, Dec. 1986, 83(24):9551-9555.

Bert et al. (Apr. 6, 2006) "Assessing IRES Activity in the HIF-1α and Other Cellular 5' UTRs", RNA, 12(6):1074-1083.

Bett et al. (Oct. 1993) "Packaging Capacity and Stability of Human Adenovirus Type Vectors", Journal of Virology, 67(10):5911-5921.

Birling et al. (May 15, 2009) "Site-Specific Recombinases for Manipulation of The Mouse Genome", Methods in Molecular Biology, 561:245-263.

Boris-Lawrie et al. (Feb. 1993) "Recent Advances in Retrovirus Vector Technology", Current Opinion in Genetics & Development, 3(1):102-109.

Boshart et al. (Jun. 1985) "A Very Strong Enhancer is Located Upstream of an Immediate Early Gene of Human Cytomegalovirus.", Cell, 41(2):521-530.

Branda et al. (Jan. 2004) "Talking about a Revolution: The Impact of Site-Specific Recombinases on Genetic Analyses in Mice", Developmental Cell, 6(1):7-28.

Brown et al. (1979) "Chemical Synthesis and Cloning of a Tyrosine TRNA Gene", Methods in Enzymology, 68:109-151.

Bucholtz F. (May 29, 2008) "Principles of Site-Specific Recombinase (SSR) Technology", Journal of Visualized Experiments, 15:652-658.

Burns et al. (Sep. 1, 1993) "Vesicular Stomatitis Virus G Glycoprotein Pseudotyped Retroviral Vectors: Concentration to Very High Titer and Efficient Gene Transfer into Mammalian and Nonmammalian Cells", Proceedings of the National Academy of Science of the USA, 90(17):8033-8037.

Carter Barrie J. (Oct. 1992) "Adeno-Associated Virus Vectors", Current Opinion in Biotechnology, 3(5):533-539.

Chen et al. (Feb. 2, 1994) "A Self-Initiating Eukaryotic Transient Gene Expression System Based on Cotransfection of Bacteriophage T7 RNA Polymerase and DNA Vectors Containing a T7 Autogene", Nucleic Acids Research, 22(11):2114-2120.

Chen et al. (Aug. 1987) "High-Efficiency Transformation of Mammalian Cells by Plasmid DNA", Molecular and Cellular Biology, 7(8):2745-2752.

Chu et al. (May 2015) "Increasing the Efficiency of Homology-Directed Repair for CRISPR-Cas9-Induced Precise Gene Editing in Mammalian Cells", Nature Biotechnology, 33(5):543-548.

(56) References Cited

OTHER PUBLICATIONS

Chu et al. (Mar. 1981) "SV40 DNA Transfection of Cells in Suspension: Analysis of Efficiency of Transcription and Translation of T-Antigen.", Gene, 13(2):197-202.
Chylinski et al. (Jun. 2014) "Classification and Evolution of Type II CRISPR-Cas Systems", Nucleic Acids Research, 42(10):6091-6105.
Cleary et al. (Dec. 2004) "Production of complex nucleic acid libraries using highly parallel in situ oligonucleotide synthesis", Nature Methods, 1(3):241-248.
Cox et al. (Oct. 2001) "Automated Selection of Anti-Protein Aptamers", Bioorganic & Medicinal Chemistry, 9(10):2525-2531.
Cox et al. (Oct. 15, 2002) "Automated Selection of Aptamers Against Protein Targets Translated in Vitro: From Gene to Aptamer", Nucleic Acids Research, e108, 30(20):14 pages.
Deng et al. (Jun. 10, 1994) "Self-Amplifying Expression from the T7 Promoter in 3T3 Mouse Fibroblasts", Gene, 143(2):245-249.
Desmet et al. (Oct. 30, 2014) "Structural basis of IL-23 antagonism by an Alphabody protein scaffold", Nature Communications, 5(5237):1-12.
DiCarlo et al. (Apr. 2013) "Genome Engineering in *Saccharomyces cerevisiae* using CRISPR-Cas Systems", Nucleic Acids Research, 41(7):4336-4343.
Dijkema et al. (Mar. 1985) "Cloning and Expression of the Chromosomal Immune Interferon Gene of the Rat", The EMBO Journal, 4(3):761-767.
Dobrikova et al. (Dec. 9, 2003) "Activity of a Type 1 Picornavirus Internal Ribosomal Entry Site is Determined by Sequences within the 3 Nontranslated Region", Proceedings of the National Academy of Sciences of the United States of America, 100(25):15125-15130.
Drmanac et al. (Jan. 1, 2010) "Human Genome Sequencing Using Unchained Base Reads on Self-Assembling DNA Nanoarrays", Science, 327(5961):78-81.
Dubensky et al. (Dec. 1, 1984) "Direct Transfection of Viral and Plasmid DNA into the Liver or Spleen of Mice", Proceedings of the National Academy of Sciences of the United States of America, 81(23):7529-7533.
Dubensky et al. (Jan. 1996) "Sindbis Virus DNA-Based Expression Vectors: Utility for in Vitro and in Vivo Gene Transfer", Journal of Virology, 70(1):508-519.
Durand et al. (Feb. 2011) "The Inside Out of Lentiviral Vectors", Viruses, 3(2):132-159.
Ebersbach et al. (Sep. 7, 2007) "Affilin—Novel Binding Molecules Based on Human γ-B-Crystallin, an All β-Sheet Protein", Journal of Molecular Biology, 372(1):172-185.
Ehrlich et al. (Aug. 19, 1980) "Isolation of an Active Heavy-Chain Variable Domain from a Homogeneous Rabbit Antibody by Cathepsin B Digestion of the Aminoethylated Heavy Chain", Biochemistry, 19(17):4091-4096.
Eid et al. (Jan. 2, 2009) "Real-time DNA Sequencing from Single Polymerase Molecules", Science, 323(5910):133-138.
Elayadi et al. (Apr. 2001) "Application of PNA and LNA Oligomers to Chemotherapy", Current Opinion in Investigational Drugs, 2(4):558-561.
Elroy-Stein et al. (Sep. 1990) "Cytoplasmic Expression System Based on Constitutive Synthesis of Bacteriophage T7 RNA Polymerase in Mammalian Cells", Proceedings of the National Academy of Sciences of the United States of America, 87(17):6743-6747.
Fechheimer et al. (Dec. 1, 1987) "Transfection of Mammalian Cells with Plasmid DNA by Scrape Loading and Sonication Loading", Proceedings of the National Academy of Sciences of the United States of America, 84(23):8463-8467.
Ferkol et al. (Aug. 1, 1993) "Regulation of the Phosphoenolpyruvate Carboxykinase/Human Factor IX Gene Introduced into the Livers of Adult Rats by Receptor-Mediated Gene Transfer", The FASEB Journal, 7(11):1081-1091.
Ferry et al. (2011) "Retroviral Vector-mediated Gene Therapy for Metabolic Diseases: An Update", Current Pharmaceutical Design, 17(24):2516-2517.

Fonfara et al. (Feb. 2014) "Phylogeny of Cas9 Determines Functional Exchangeability of Dual-RNA and Cas9 Among Orthologous Type II CRISPR-Cas Systems", Nucleic Acids Research, 42(4):2577-2590.
Fraley et al. (Jul. 1, 1979) "Entrapment of a Bacterial Plasmid in Phospholipid Vesicles: Potential for Gene Transfer", Proceedings of the National Academy of Sciences of the United States of America, 76(7):3348-3352.
Fuerst et al. (Nov. 1, 1986) "Eukaryotic Transient-Expression System Based on Recombinant Vaccinia Virus that Synthesizes Bacteriophage T7 RNA Polymerase", Proceedings of the National Academy of Sciences of the United States of America, 83(21):8122-8126.
Furler et al. (Jun. 22, 2001) "Recombinant AAV Vectors Containing the Foot and Mouth Disease Virus 2A Sequence Confer Efficient Bicistronic Gene Expression in Cultured Cells and Rat Substantia Nigra Neurons", Gene Therapy, 8(11):864-873.
Gaj et al. (Jan. 2014) "Expanding the Scope of Site-Specific Recombinases for Genetic and Metabolic Engineering", Biotechnology and Bioengineering, 111(1):1-15.
Gao et al. (May 15, 1994) "A Sustained, Cytoplasmic Transgene Expression System Delivered by Cationic Liposomes", Biochemical and Biophysical Research Communications, 200(3):1201-1206.
Gao et al. (Jun. 25, 1993) "Cytoplasmic Expression of a Reporter Gene by Co-Delivery of T7 RNA Polymerase and T7 Promoter Sequence with Cationic Liposomes", Nucleic Acids Research, 21(12):2867-2872.
Garcia-Otin et al. (Jan. 1, 2006) "Mammalian Genome Targeting Using Site-Specific Recombinases", Frontiers in Bioscience, 11:1108-1136.
Garlapati et al. (Jan. 30, 2004) "Identification of a Novel Internal Ribosome Entry Site in Giardiavirus That Extends to Both Sides of the Initiation Codon", Journal of Biological Chemistry, 279(5):3389-3397.
Garst et al. (Dec. 12, 2016) "Genome-Wide Mapping of Mutations at Single-Nucleotide Resolution for Protein, Metabolic and Genome Engineering", Nature Biotechnology, 35(1):48-55.
Gilbert et al. (Oct. 23, 2014) "Genome-Scale CRISPR-Mediated Control of Gene Repression and Activation", Cell, 159(3):647-661.
Glenn et al. (Sep. 2011) "Field Guide to Next-Generation DNA Sequencers", Molecular Ecology Resources, 11(5):759-769.
Gopal Venkatt. (May 1985) "Gene Transfer Method for Transient Gene Expression, Stable Transformation, and Cotransformation of Suspension Cell Cultures", Molecular and Cellular Biology, 5(5):1188-1190.
Gorman et al. (Nov. 1, 1982) "The Rous Sarcoma Virus Long Terminal Repeat is a Strong Promoter when Introduced into a Variety of Eukaryotic Cells by DNA-Mediated Transfection", Proceedings of the National Academy of Sciences of the United States of America, 79(22):6777-6781.
Grabulovski et al. (Mar. 2007) "A Novel, Non-immunogenic Fyn SH3-derived Binding Protein with Tumor Vascular Targeting Properties", Journal of Biological Chemistry, 282(5):3196-3204.
Graham et al. (Apr. 1973) "A New Technique for the Assay of Infectivity of Human Adenovirus 5 DNA", Virology, 52(2):456-467.
Greco et al. (May 5, 2015) "Improving the Safety of Cell Therapy With the TK-Suicide Gene", Frontiers in Pharmacology, 6:13 pages.
Gurtu et al. (Dec. 4, 1996) "IRES bicistronic expression vectors for efficient creation of stable mammalian cell lines", Biochemical and Biophysical Research Communications, 229(1):295-298.
Hackland et al. (1994) "Coat Protein-Mediated Resistance in Transgenic Plants", Archives of Virology, 139(1-2):1-22.
Haj-Ahmad et al. (Jan. 1986) "Development of a Helper-Independent Human Adenovirus Vector and Its Use in the Transfer of the Herpes Simplex Virus Thymidine Kinase Gene", Journal of Virology, 57(1):267-274.
Harland et al. (Sep. 1, 1985) "Translation of MRNA Injected into Xenopus Oocytes is Specifically Inhibited by Antisense RNA", Journal of Cell Biology, 101(3):1094-1099.
Havlicek et al. (Feb. 1, 2017) "Re-engineered RNA-Guided FokI-Nucleases for Improved Genome Editing in Human Cells", Molecular Therapy, 25(2):342-355.

(56) References Cited

OTHER PUBLICATIONS

Huston et al. (Aug. 1, 1988) "Protein Engineering of Antibody Binding Sites: Recovery of Specific Activity in an Anti-Digoxin Single-Chain Fv Analogue Produced in *Escherichia coli*.", Proceedings of the National Academy of Sciences of the United States of America, 85(16):5879-5883.
Inbar et al. (Sep. 1, 1972) "Localization of Antibody-Combining Sites within the Variable Portions of Heavy and Light Chains", Proceedings of the National Academy of Sciences of the United States of America, 69(9);2659-2662.
Jakočiūna et al. (Mar. 2015) "Multiplex Metabolic Pathway Engineering Using CRISPR/Cas9 In *Saccharomyces cerevisiae*", Metabolic Engineering, 28:213-222.
Jang et al. (Apr. 1989) "Initiation of protein synthesis by internal entry of ribosomes into the 5' nontranslated region of encephalomyocarditis virus RNA in vivo.", Journal of Virology, 63(4):1651-1660.
Jinek et al. (Aug. 17, 2012) "A Programmable Dual-RNA-Guided DNA Endonuclease in Adaptive Bacterial Immunity", Science, 337(6069):816-821.
Johnson et al. (Jul. 26, 2012) "Sensitive affimer and antibody based impedimetric label-free assays for C-reactive protein", Analytical Chemistry, 84(15):6553-6560.
Jones et al. (Nov. 27, 2014) "Improving the Safety of Cell Therapy Products by Suicide Gene Transfer", Frontiers in Pharmacology, 5:8 pages.
Junemann et al. (Apr. 5, 2013) "Updating Benchtop Sequencing Performance Comparison", Nature Biotechnology, 31(4):294-296.
Kaneda et al. (Jan. 20, 1989) "Increased Expression of DNA Cointroduced with Nuclear Protein in Adult Rat Liver", Science, 243(4889):375-378.
Kapitonov et al. (Dec. 28, 2015) "ISC, a Novel Group of Bacterial and Archaeal DNA Transposons That Encode Cas9 Homologs", Journal of Bacteriology, 198(5):797-807.
Kato et al. (Feb. 25, 1991) "Expression of Hepatitis B Virus Surface Antigen in Adult Rat Liver. Co-Introduction of DNA and Nuclear Protein by a Simplified Liposome Method", Journal of Biological Chemistry, 266(6):3361-3364.
Kaufman et al. (Aug. 25, 1991) "Improved vectors for stable expression of foreign genes in mammalian cells by use of the untranslated leader sequence from EMC virus", Nucleic Acids Research, 19(16):4485-4490.
Kenan et al. (1999) "In Vitro Selection of Aptamers from RNA Libraries", Methods in Molecular Biology, 118:217-231.
Kim et al. (Apr. 29, 2011) "High Cleavage Efficiency of a 2A Peptide Derived from Porcine Teschovirus-1 in Human Cell Lines, Zebrafish and Mice", PLoS One, e18556, 6(4):8 pages.
Kim et al. (Jun. 8, 2007) "Polony Multiplex Analysis of Gene Expression (PMAGE) in Mouse Hypertrophic Cardiomyopathy", Science, 316(5830):1481-1484.
Klein et al. (May 7, 1987) "High-Velocity Microprojectiles for Delivering Nucleic Acids into Living Cells", Nature, 327:70-73.
Koide et al. (Feb. 2007) "Monobodies: Antibody Mimics Based on the Scaffold of the Fibronectin Type III Domain", Methods in Molecular Biology, 352:95-109.
Koike-Yusa et al. (Mar. 2014) "Genome-Wide Recessive Genetic Screening in Mammalian Cells with a Lentiviral CRISPR-Guide RNA Library", Nature Biotechnology, 32(3):267-273.
Kolb Andreas F. (2002) "Genome Engineering Using Site-Specific Recombinases", Cloning Stem Cells, 4(1):65-80.
Konermann et al. (Jan. 29, 2015) "Genome-Scale Transcriptional Activation by an Engineered CRISPR-Cas9 Complex", Nature, 517(7536):583-588.
Koshkin et al. (Apr. 2, 1998) "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition", Tetrahedron, 54(14):3607-3630.

Kotin Robertm. (Jul. 1994) "Prospects for the Use of Adeno-Associated Virus as a Vector for Human Gene Therapy", Human Gene Therapy, 5(7):793-801.
Krappmann Sven. (Mar. 2014) "Genetic Surgery In Fungi: Employing Site-Specific Recombinases For Genome Manipulation", Applied Microbiology and Biotechnology, 98(5):1971-1982.
Krehenbrink et al. (Nov. 28, 2008) "Artificial binding proteins (Affitins) as probes for conformational changes in secretin PulD", Journal of Molecular Biology, 383(5):1058-1068.
Kurreck et al. (May 1, 2002) "Design of Antisense Oligonucleotides Stabilized by Locked Nucleic Acids", Nucleic Acids Research, 30(9):1911-1918.
Lebkowski et al. (Oct. 1988) "Adeno-associated virus: a vector system for efficient introduction and integration of DNA into a variety of mammalian cell types", Molecular and Cellular Biology, 8(10):3988-3996.
Ledford Heidi. (Oct. 1, 2015) "Bacteria Yield New Gene Cutter", Molecular Biology, 526(7571):17.
Li et al. (Apr. 2012) "Regulation of Budding Yeast Mating-Type Switching Donor Preference by the FHA Domain of Fkh1", PLoS Genetics, 8(4):e1002630:14 pages.
Lin et al. (Oct. 2016) "Increasing the Efficiency of CRISPR/Cas9-mediated Precise Genome Editing of HSV-1 Virus in Human Cells", Scientific Reports, 6(1):13 pages.
Lois et al. (Feb. 1, 2002) "Germline Transmission and Tissue-Specific Expression of Transgenes Delivered by Lentiviral Vectors", Science, 295(5556):868-872.
Lopatniuk et al. (Mar. 24, 2015) "Testing the Utility of Site-Specific Recombinases For Manipulations of Genome of Moenomycin Producer *Streptomyces ghanaensis* ATCC14672", Journal of Applied Genetics, 56:547-550.
Lundstrom et al. (Mar. 2003) "Latest development in viral vectors for gene therapy", Trends Biotechnology, 21(3):117-122.
Lyu et al. (2016) "Generating Cell Targeting Aptamers for Nanotheranostics Using Cell-SELEX", Theranostics, 6(9):1440-1452.
Margulies et al. (Sep. 15, 2005) "Genome sequencing in microfabricated high-density picolitre reactors", Nature, 437:376-380.
Martin et al. (Dec. 30, 2003) "Translation of the Human Angiotensin II Type 1 Receptor mRNA is Mediated by a Highly Efficient Internal Ribosome Entry Site", Molecular and Cellular Endocrinology, 212(1-2):51-61.
Martineau et al. (Sep. 2004) "Internal Ribosome Entry Site Structural Motifs Conserved among Mammalian Fibroblast Growth Factor 1 Alternatively Spliced mRNAs", Molecular and Cell Biology, 24(17):7622-7635.
Maruyama et al. (May 2015) "Increasing the efficiency of precise genome editing with CRISPR-Cas9 by inhibition of nonhomologous end joining", National Biotechnology, 33(5):538-542.
Michael et al. (Apr. 5, 1993) "Binding-Incompetent Adenovirus Facilitates Molecular Conjugate-Mediated Gene Transfer by the Receptor-Mediated Endocytosis Pathway", The Journal of Biological Chemistry, 268(10):6866-6869.
Miller et al. (Oct. 7, 1989) "Improved Retroviral Vectors for Gene Transfer and Expression", Biotecniques, 7(9):980-990.
Miller A. Dusty. (1990) "Retrovirus Packaging Cells", Human Gene Therapy, 1(1):5-14.
Mitsui et al. (Jun. 16, 2017) "Viral Vector-Based Innovative Approaches to Directly Abolishing Tumorigenic Pluripotent Stem Cells for Safer Regenerative Medicine", Molecular Therapy Methods & Clinical Developments, 5:51-58.
Mittereder et al. (Jun. 1994) "Adenovirus-Mediated Transfer of the Human Cystic Fibrosis Transmembrane Conductance Regulator cDNA", Human Gene Therapy, 5(6):717-729.
Moffatt et al. (May 5, 1986) "Use of Bacteriophage T7 RNA Polymerase to Direct Selective High-Level Expression of Cloned Genes", Journal of Molecular Biology, 189(1):113-130.
Mosser et al. (1997) "Use of a Dicistronic Expression Cassette Encoding the Green Fluorescent Protein for the Screening and Selection of Cells Expressing Inducible Gene Products", BioTechniques, 22(1):150-161.

(56) References Cited

OTHER PUBLICATIONS

Murovec et al. (Aug. 2017) "New Variants of CRISPR RNA-Guided Genome Editing Enzymes", Plant Biotechnology Journal, 15(8):917-926.
Muzyczka N (1992) "Use of Adeno-Associated Virus as a General Transduction Vector for Mammalian Cells", Current Topics in Microbiology and Immunology, 158:97-129.
Narang et al. (1979) "Improved phosphotriester method for the synthesis of gene fragments", Methods in Enzymology, 8:90-98.
NCBI (May 4, 2021) "Belliella Baltica Dsm 15883, Complete Sequence", NCBI Accession No. NC_018010.1, 2 pages.
NCBI (Jan. 31, 2021) "Corynebacterium Diphtheriae 241, Complete Sequence", NCBI Accession No. NC_016782.1, 2 pages.
NCBI (Feb. 7, 2021) "Corynebacterium Diphtheriae Hc01, Complete Sequence", NCBI Accession No. NC_016786.1, 2 pages.
NCBI (Jan. 17, 2021) "Corynebacterium Ulcerans 809, Complete Sequence", NCBI Accession No. NC_017317.1, 2 pages.
NCBI (Jan. 17, 2021) "Corynebacterium Ulcerans Br-ad22, Complete Sequence", NCBI Accession No. NC_015683.1, 2 pages.
NCBI (Aug. 3, 2016) "Crispr-Associated Protein [*Campylobacter jejuni* Subsp. *jejuni* Nctc 11168=Atcc 700819]", NCBI Accession No. YP_002344900.1, 2 pages.
NCBI (Dec. 16, 2014) "Crispr-System-like Protein [*Streptococcus thermophilus* Lmd-9]", NCBI Accession No. YP_820832.1, 2 pages.
NCBI (Oct. 29, 2018) "Hypothetical Protein [campylobacter Fetus]", NCBI Accession No. WP_059434633.1, 1 page.
NCBI (Dec. 17, 2014) "Hypothetical Protein Lin2744 [listeria Innocua Clip11262]", NCBI Accession No. NP_472073.1, 2 pages.
NCBI (Dec. 16, 2014) "Hypothetical Protein Nma0631 [neisseria Meningitidis Z2491]", NCBI Accession No. YP_002342100.1, 2 pages.
NCBI (Oct. 9, 2019) "Multispecies: Type II Crispr Rna-guided Endonuclease Cas9 [campylobacter]", NCBI Accession No. WP_022552435.1, 2 pages.
NCBI (Nov. 28, 2020) "Prevotella Intermedia 17 Chromosome II, Complete Sequence", NCBI Accession No. NC_017861.1, 2 pages.
NCBI, (May 4, 2021) "Psychroflexus Torquis Atcc 700755, Complete Sequence", NCBI Accession No. NC_018721.1, 2 pages.
NCBI (Jan. 24, 2021) "Spiroplasma Syrphidicola Ea-1, Complete Sequence", NCBI Accession No. NC_021284.1, 2 pages.
NCBI (Jan. 24, 2021) "Spiroplasma Taiwanense Ct-1, Complete Sequence", NCBI Accession No. NC_021846.1 2 pages.
NCBI (Dec. 18, 2014) "*Streptococcus iniae* Sf1, Complete Genome", NCBI Accession No. NC_021314.1, 1 page.
NCBI (Oct. 9, 2019) "Type II Crispr Rna-guided Endonuclease Cas9 [*Campylobacter coli*]", NCBI Accession No. WP_060786116.1, 2 pages.
NCBI (Oct. 9, 2019) "Type II Crispr Rna-guided Endonuclease Cas9 [enterococcus Faecalis]", NCBI Accession No. WP_033919308.1, 2 pages.
NCBI (Oct. 9, 2019) "Type II Crispr Rna-Guided Endonuclease Cas9 [lacticaseibacillus Rhamnosus]", NCBI Accession No. WP_032965177.1, 2 pages.
NCBI (Oct. 9, 2019) "Type II Crispr Rna-Guided Endonuclease Cas9 [lactobacillus Rhamnosus]", NCBI Accession No. WP_048482595.1, 2 pages.
NCBI (Oct. 9, 2019) "Type II Crispr Rna-Guided Endonuclease Cas9 [listeria Monocytogenes]", NCBI Accession No. WP_061665472.1, 2 pages.
NCBI (Oct. 9, 2019) "Type II Crispr Rna-Guided Endonuclease Cas9 [neisseria Meningitidis]", NCBI Accession No. WP_061704949.1, 2 pages.
NCBI (Oct. 9, 2019) "Type II Crispr Rna-Guided Endonuclease Cas9 [*Staphylococcus aureus*]", NCBI Accession No. WP_001573634.1, 2 pages.
NCBI (Oct. 9, 2019) "Type II Crispr Rna-guided Endonuclease Cas9 [*Streptococcus mutans*]", NCBI Accession No. WP_024786433.1, 2 pages.
NCBI (Oct. 9, 2019) "Type II Crispr Rna-guided Endonuclease Cas9 [*Streptococcus mutans*]", NCBI Accession No. WP_061046374.1, 2 pages.
NCBI (Oct. 9, 2019) "Type II Crispr Rna-guided Endonuclease Cas9 [*Streptococcus pyogenes*]", NCBI Accession No. WP_002989955.1, 2 pages.
NCBI (Oct. 9, 2019) "Type II Crispr Rna-guided Endonuclease Cas9 [*Streptococcus pyogenes*]", NCBI Accession No. WP_011528583.1, 2 pages.
NCBI, (Oct. 9, 2019) "Type II Crispr Rna-guided Endonuclease Cas9 [*Streptococcus pyogenes*]", NCBI Accession No. WP_038434062.1, 2 pages.
NCBI (Jun. 20, 2019) "Type II-B CRISPR-Associated RNA-Guided Endonuclease Cas9/Csx12 [Francisella hispaniensis]", NCBI Accession No. WP_014548420.1, 2 pages.
NCBI (Jun. 20, 2019) "Type II-B Crispr-Associated Rna-Guided Endonuclease Cas9/csx12 [francisella Tularenisis]", NCBI Accession No. WP_032729892.1, 2 pages.
NCBI (Jun. 19, 2019) "Type II-B Crispr-associated Rna-Guided Endonuclease Cas9/csx12 [legionella Pneumophila]", NCBI Accession No. WP_062726656.1, 2 pages.
Nern et al. (Aug. 23, 2011) "Multiple new site-specific recombinases for use in manipulating animal genomes", Proceedings of the National Academy of Sciences of the United States of America, 108(34):14198-14203.
Nguyen et al. (Jul. 1, 2000) "Improving SH3 Domain Ligand Selectivity Using a Non-Natural Scaffold", Chemistry & Biology, 7(7):463-473.
Nicolau et al. (1987) "[16]Lipsomes as Carriers for in Vivo Gene Transfer and Expression", Methods in Enzymology, 149:157-176.
Nicolau et al. (Oct. 11, 1982) "Liposome-Mediated DNA Transfer in Eukaryotic Cells. Dependence of the Transfer Efficiency Upon the Type of Liposomes Used and the Host Cell Cycle Stage", Biochimica et Biophysica Acta, 721(2):185-190.
Nygren Per-Ake. (Jun. 2008) "Alternative binding proteins: affibody binding proteins developed from a small three-helix bundle scaffold", The FEBS Journal, 275(11):2668-2676.
Obika et al. (Jul. 23, 1998) "Stability and Structural Features of the Duplexes Containing Nucleoside Analogues with a Fixed N-type Conformation, 2'-o,4'-c-methyleneribonucleosides", Tetrahedron Letters, 39(30):5401-5404.
Pack et al. (Feb. 18, 1992) "Miniantibodies: use of amphipathic helices to produce functional, flexibly linked dimeric FV fragments with high avidity in *Escherichia coli*", Biochemistry, 31(6):1579-1584.
Pan et al. (Oct. 2016) "CRISPR RNA-Guided FokI Nucleases Repair a PAH Variant in a Phenylketonuria Model", Scientific Reports, 6(1):7 pages.
Pedersen et al. (Apr. 1, 2002) "Human Insulin-like Growth Factor II Leader 2 Mediates Internal Initiation of Translation", Biochemical Journal, 363(Pt 1):37-44.
Perales et al. (Apr. 1, 1994) "Gene Transfer In Vivo: Sustained Expression and Regulation of Genes Introduced into the Liver by Receptor-Targeted Uptake", Proceedings of the National Academy of Sciences of the United States of America, 91(9):4086-4090.
Perri et al. (Oct. 2003) "An Alphavirus Replicon Particle Chimera Derived from Venezuelan Equine Encephalitis and Sindbis Viruses is a Potent Gene-Based Vaccine Delivery Vector", Journal of Virology, 77(19):10394-10403.
Porta et al. (Jun. 1, 1996) "Use of Viral Replicons for the Expression of Genes in Plants", Molecular Biotechnology, 5(3):209-221.
Potter et al. (Nov. 1, 1984) "Enhancer-Dependent Expression of Human Kappa Immunoglobulin Genes Introduced into Mouse Pre-B Lymphocytes by Electroporation", Proceedings of the National Academy of Sciences of the United States of America, 81(22):7161-7165.
Provost et al. (Oct. 2007) "Viral 2A peptides allow expression of multiple proteins from a single ORF in transgenic zebrafish embryos", Genesis, 45(10):625-629.
Ramesh et al. (Jul. 1, 1996) "High-Riter Bicistronic Retroviral Vectors Employing Foot-and-Mouth Disease Virus Internal Ribosome Entry Site", Nucleic Acids Research, 24(14):2697-2700.

(56) References Cited

OTHER PUBLICATIONS

Rees et al. (Jan. 1996) "Bicistronic vector for the creation of stable mammalian cell lines that predisposes all antibiotic-resistant cells to express recombinant protein", BioTechniques, 20(1):102-110.
Rich et al. (Aug. 1993) "Development and Analysis of Recombinant Adenoviruses for Gene Therapy of Cystic Fibrosis", Human Gene Therapy, 4(4):461-476.
Richardson et al. (Jan. 20, 2016) "Enhancing Homology-Directed Genome Editing by Catalytically Active and Inactive CRISPR-Cas9 Using Asymmetric Donor DNA", Nature Biotechnology, 34(3):339-344.
Riechmann et al. (1988) "Reshaping Human Antibodies for Therapy", Nature, Mar. 24, 332(6162):323-327.
Rippe et al. (Feb. 1990) "DNA-Mediated Gene Transfer into Adult Rat Hepatocytes in Primary Culture", Molecular and Cellular Biology, 10(2):689-695.
Ronda et al., "Credit: CRISPR Mediated Multi-Loci Gene Integration In *Saccharomyces cerevisiae*", Microbial Cell Factory, 2015, 14:11 pages.
Roy et al. (Jul. 2018) "Multiplexed Precision Genome Editing with Trackable Genomic Barcodes in Yeast", Nature Biotechnology, 36(6):512-520.
Ryan et al. (2014) "Multiplex Engineering of Industrial Yeast Genomes Using Crisprm", Methods in Enzymology, 546:473-489.
Ryan et al. (Aug. 19, 2014) "Selection of Chromosomal DNA Libraries Using a Multiplex CRISPR System", eLife, 3:e03703:15 pages.
Scarpa et al. (Feb. 1991) "Characterization of Recombinant Helper Retroviruses from Moloney-Based Vectors in Ecotropic and Amphotropic Packaging Cell Lines", Virology, 180(2):849-852.
Seth et al. (Feb. 1994) "Mechanism of enhancement of DNA expression consequent to cointernalization of a replication-deficient adenovirus and unmodified plasmid DNA", Journal of Virology, 68(2):933-940.
Shalem et al. (Jan. 3, 2014) "Genome-Scale CRISPR-Cas9 Knockout Screening in Human Cells", Science, 343(6166):84-87.
European Search Report received in EP Application No. 18856837.2, mailed on Apr. 22, 2021, 8 pages.
Shen et al. (Jul. 9, 2012) "Particlecall: A Particle Filter for Base Calling in Next-Generation Sequencing Systems", BMC Bioinformatics, 13:11 pages.
Shmakov et al. (Nov. 5, 2015) "Discovery and Functional Characterization of Diverse Class 2 CRISPR-Cas Systems", Molecular Cell, 60(3):385-397.
Silverman et al. (Nov. 20, 2005) "Multivalent Avimer Proteins Evolved by Exon Shuffling of a Family of Human Receptor Domains", Nature Biotechnology, 23(12):1556-1561.
Simon et al. (Oct. 15, 1992) "Peptoids: A Modular Approach to Drug Discovery", Proceedings of the National Academy of Sciences of the United States of America, 89(20):9367-9371.
Skerra Arne. (Jun. 2008) "Alternative Binding Proteins: Anticalins—Harnessing the Structural Plasticity of the Lipocalin Ligand Pocket to Engineer Novel Binding Activities", The FEBS Journal, 275(11):2677-2683.
Smith et al. (Feb. 13, 2017) "A method for high-throughput production of sequence-verified DNA libraries and strain collections", Molecular Systems Biology, 13(2):15 pages.
Smith et al. (Dec. 1981) "Comparison of Biosequences", Advances in Applied Mathematics, 2(4):482-489.
Smith et al. (Apr. 2010) "Site-specific recombination by phiC31 integrase and other large serine recombinases", Biochemical Society Transactions, 38(2):388-394.
Song et al. (Jan. 28, 2016) "RS-1 enhances CRISPR/Cas9- and TALEN-mediated knock-in efficiency", Nature Communications, 7:7 pages.
Stein et al. (Jun. 1998) "Translation of vascular endothelial growth factor mRNA by internal ribosome entry: implications for translation under hypoxia", Molecular and Cellular Biology, 18(6):3112-3119.

Stumpp et al. (Aug. 2008) "DARPins: a new generation of protein therapeutics", Drug Discovery Today, 13(15-16):695-701.
Svensen et al. (Sep. 23, 2011) "Microarray Generation of Thousand-Member Oligonucleotide Libraries", PLoS One, 6(9):e24906(8 pages).
Talas et al. (Jun. 30, 2017) "A Convenient Method to Pre-screen Candidate Guide RNAs for CRISPR/Cas9 Gene Editing by NHEJ-mediated Integration of a 'Self-cleaving' GFP-expression Plasmid", DNA Research, 24(6):609-621.
Thudi et al. (Jan. 2012) "Current State-of-Art of Sequencing Technologies for Plant Genomics Research", Briefings in Functional Genomics, 11(1):3-11.
Trichas et al. (Sep. 15, 2008) "Use of the viral 2A peptide for bicistronic expression in transgenic mice", BMC Biology, 6(40):13 pages.
Tsai et al. (Jun. 2014) "Dimeric CRISPR RNA-Guided FokI Nucleases for Highly Specific Genome Editing", Nature Biotechnology, 32(6):569-576.
Turan et al. (Sep. 2, 2011) "Site-specific recombinases: from tag-and-target- to tag-and-exchange-based genomic modifications", The Faseb Journal, 25:4088-4107.
Tur-Kaspa et al. (Feb. 1986) "Use of Electroporation to Introduce Biologically Active Foreign Genes into Primary Rat Hepatocytes", Molecular and Cellular Biology, 6(2):716-718.
Verhoeyan et al. (Mar. 25, 1988) "Reshaping human antibodies: grafting an antilysozyme activity", Science, 239(4847):1534-1536.
Vincke et al. (Aug. 2012) "Introduction to Heavy Chain Antibodies and Derived Nanobodies", Methods in Molecular Biology, 911:15-26.
Wagner et al., Jul. 1, 1992, "Coupling of Adenovirus to Transferrin-Polylysine/DNA Complexes Greatly Enhances Receptor-Mediated Gene Delivery and Expression of Transfected Genes", Proceedings of the National Academy of Sciences of the United States of America, 89(13):6099-6103.
Wagner et al. (May 1990) "Transferrin-Polycation Conjugates as Carriers for DNA Uptake into Cells", Proceedings of the National Academy of Sciences of the United States of America, 87(9):3410-3414.
Walther et al. (Aug. 2000) "Viral Vectors for Gene Transfer: A Review of Their Use in The Treatment of Human Diseases", Drugs, 60(2):249-271.
Wang et al. (Jan. 3, 2014) "Genetic Screens in Human Cells Using the CRISPR-Cas9 System", Science, 343(6166):80-84.
Wang et al. (Jul. 21, 2016) "Nanobody-Derived Nanobiotechnology Tool Kits or Diverse Biomedical and Biotechnology Applications", International Journal of Nanomedicine, 11:3287-3303.
Wang et al. (May 29, 2018) "Systematic Evaluation of CRISPR-Cas Systems Reveals Design Principles for Genome Editing in Human Cells", Genome Biology, 19(1):2 pages.
Warnock et al. (Apr. 2, 2011) "Introduction to Viral Vectors", Methods in Molecular Biology, 737:1-25.
Winter et al. (Jan. 24, 1991) "Man-Made Antibodies", Nature, 349(6307):293-299.
Wirth et al. (Oct. 2007) "Road to Precision: Recombinase-Based Targeting Technologies for Genome Engineering", Current Opinion in Biotechnology, 18(5):411-419.
Wu et al. (Feb. 1, 1988) "Evidence for Targeted Gene Delivery to Hep G2 Hepatoma Cells in Vitro", Biochemistry, 27(3):887-892.
Wu et al. (Dec. 1993) "Liver-Directed Gene Delivery", Advanced Drug Delivery Reviews, 12(3):159-167.
Wu et al. (Apr. 5, 1987) "Receptor-Mediated in Vitro Gene Transformation by a Soluble DNA Carrier System", The Journal of Biological Chemistry, 262(10):4429-4432.
Xie et al. (Dec. 28, 2007) "Distinct Roles of Chromatin-Associated Factors MDC1 and 53BP1 in Mammalian Double Strand Break Repair", Molecular Cell, 28(6):1045-1057.
Yang et al. (Dec. 1, 1990) "In Vivo and In Vitro Gene Transfer to Mammalian Somatic Cells by Particle Bombardment", Proceedings of the National Academy of Sciences of the United States of America, 87(24):9568-9572.
Zetsche et al. (Oct. 22, 2015) "Cpf1 is a Single RNA-Guided Endonuclease of a Class 2 CRISPR-Cas System", Cell, 163(3):759-771.

(56) References Cited

OTHER PUBLICATIONS

Zhang et al. (Feb. 14, 2017) "Progress in Genome Editing Technology and Its Application in Plants", Frontiers in Plant Science, 8:17 pages.

Zhou et al. (Jun. 1, 1994) "Adeno-Associated Virus 2-Mediated High Efficiency Gene Transfer into Immature and Mature Subsets of Hematopoietic Progenitor Cells in Human Umbilical Cord Blood", Journal of Experimental Medicine, 179(6):1867-1875.

Zhou et al. (May 22, 2014) "High-Throughput Screening of a CRISPR/Cas9 Library for Functional Genomics in Human Cells", Nature, 509(7501):487-491.

International Search Report and Written Opinion received for PCT Application No. PCT/US2018/051240, mailed on Mar. 4, 2019, 12 pages.

Barr et al. (Jan. 1, 1994) "Efficient Catheter-Mediated Gene Transfer into the Heart Using Replication-Defective Adenovirus", Gene Therapy, 1(1):51-58. (Abstract).

Cumber et al. (Jul. 1, 1992) "Comparative stabilities in vitro and in vivo of a recombinant mouse antibody FvCys fragment and a bisFvCys conjugate", The Journal of Immunology, 149(1):120-126.

Fernandes et al. (Jan. 2016) "Type II and Type V Crispr Effector Nucleases From a Structural Biologist's Perspective", Postepy Biochemical, 62(3):315-326. (Abstract).

Li et al. (2015) "Metabolic Engineering of *Escherichia coli* Using CRISPR-Cas9 Meditated Genome Editing", Metabolic Engineering, 31:13-21.

Orum et al. (Jun. 1, 2001) "Locked Nucleic Acids: A Promising Molecular Family for Gene-function Analysis and Antisense Drug Development", Current Opinion in Molecular Therapeutics, 3(3):239-243. (Abstract).

Shelling et al. (May 1, 1994) "Targeted Integration of Transfected and Infected Adeno-Associated Virus Vectors Containing the Neomycin Resistance Gene", Gene Therapy, 1(3):165-169 (Abstract).

\* cited by examiner

FIG. 2B

CRISPR/Cas9 editing of target genomic locus (ADE2)

```
WT sequence: CGCAAGCATCAATGGTATAATGTCCAGAGTTGTGAGGCCTTGGGGCAATTTCGTTAATAA
clone #1:    CGCAAGCATCAATGGTACAGCGT-CAGAGCTGTCACGCCTTGGGGCAATTTCGTTAATAA
clone #2:    CGCAAGCATCAATGGTACAGCGT-CAGAGCTGTCACGCCTTGGGGCAATTTCGTTAATAA
clone #3:    CGCAAGCATCAATGGTACAGCGT-CAGAGCTGTCACGCCTTGGGGCAATTTCGTTAATAA
clone #4:    CGCAAGCATCAATGGTACAGCGT-CAGAGCTGTCACGCCTTGGGGCAATTTCGTTAATAA
clone #5:    CGCAAGCATCAATGGTACAGCGT-CAGAGCTGTCACGCCTTGGGGCAATTTCGTTAATAA
clone #6:    CGCAAGCATCAATGGTACAGCGT-CAGAGCTGTCACGCCTTGGGGCAATTTCGTTAATAA
donor:       CGCAAGCATCAATGGTACA*GT-CAGAG**GT*A*GCCTTGGGGCAATTTCGTTAATAA
```

85% sequence-perfect guide-donor
15% mutated guide RNA spiked-in

FIG. 8 (cont'd)

VALIDATE EDIT

9) -re-array unique variants in 1536 format with edits embedded within a distinct chromosomal window
-pool colonies and extract genomic DNA 10) -PCR amplify desired chromosomal windows followed by tagmentation- or shearing-based high-throughput amplicon sequencing
-minimum depth of 100*number of variants reads per variant 11) -consensus sequence of reads harboring designed variant enables variant validation
-lack of reads harboring designed variants indicates unsuccessful editing 12) -consolidate validated/desired clones, discard unedited/undesired clones 13) -on select clones of high-interest (~1000s), whole-genome sequencing to confirm test for off-target edits, genome abnormalities

FIG. 10B

```
                GGTGTGTCACTGTTACTCAAGATTCTTCTTTGCAAGACGGT →
                 G  V  V  T  V  T  Q  D  S  L  Q  D  G guide RNA                        CAAGATTCTTCTTTGCAAGA
                                 ||||||||||||||||||||
variant      ...GCCGTAGTAACAGTAACACAGGACCAGCAGCCTACAGGACCAGT...
donor DNA       A  V  V  T  V  T  Q  D  S  L  Q  D  G pseudo-WT    ...GGTGTAGTAACAGTAACAGGACCAGCAGCCTACAGGACCAGT...
donor DNA       G  V  V  T  V  T  Q  D  S  L  Q  D  G
```

MULTIPLEX PRODUCTION AND BARCODING OF GENETICALLY ENGINEERED CELLS

CROSS-REFERENCE TO RELATED APPLICATIONS

This application is a National Stage Application pursuant to 35 U.S.C. § 371, of United States International Application No. PCT/US2018/051240, filed Sep. 14, 2018, which claims priority to, and the benefit under 35 U.S.C. § 119 (e) of U.S. provisional application No. 62/559,493, filed on Sep. 15, 2017, the entire contents of which are incorporated herein by reference in their entirety.

REFERENCE TO A SEQUENCE LISTING

The instant application contains a Sequence Listing, which has been submitted in ASCII format via EFS-Web and is hereby incorporated by reference in its entirety. Said ASCII copy, created on or about Jan. 15, 2019, is name 041243-526001WO_Sequence_Listing_ST25.txt and is 4,465 bytes in size.

STATEMENT REGARDING FEDERALLY SPONSORED RESEARCH OR DEVELOPMENT

This invention was made with government support under contract HG000205 awarded by the National Institutes of Health and contract 70NANB15H268 awarded by the National Institute of Standards and Technology. The government has certain rights in the invention.

TECHNICAL FIELD

The present disclosure pertains generally to the field of genome engineering using RNA-guided nucleases. In particular, the disclosure relates to compositions and methods for multiplex high-throughput production and validation of genetically engineered cells using RNA-guided nucleases and barcoding.

BACKGROUND

The advent of programmable genome editing via the CRISPR/Cas9 system is enabling rapid advances in synthetic biology and genetic engineering. The *Streptococcus pyogenes* bacterial type II clustered regularly-interspaced short palindromic repeats (CRISPR)-associated protein 9 (Cas9) was the first RNA-guided nuclease (RGN) demonstrated to cut nearly any genomic location using a guide RNA (gRNA) with homology to the target region[2]. Utilizing conserved homologous recombination-based DNA repair pathways present in the host cells, donor DNA with homology flanking the cut site can be used to repair that break and introduce a genetic change of interest. The short specificity-determining region of the gRNA (generally 20 nucleotides (nt) in length) and donor DNA lengths (~100-150 nt) are compatible with highly parallel array-based oligonucleotide library synthesis, allowing facile creation of gRNA-donor libraries directed against thousands of targets[1,3-8]. To date, however, production of variant libraries has been restricted to pools, which greatly limits the options for characterizing the phenotype of individual variants. For example, microscopy, metabolomics, and many enzymatic assay reporters are not amenable to a pooled format.

CRISPR editing is particularly efficient in yeast because of its strong preference for using homologous recombination (HR) to repair double-strand breaks in the presence of donor DNA, eliminating the need for selectable markers when making edits to the genome[9-11]. In contrast to the near 100% Cas9 editing efficiency reported in yeast[12-14], gene editing in metazoan cells is hindered by the preference for non-homologous end joining (NHEJ) over HR, and editing by HR in human cells has only reached a maximal efficiency of about 10-60%[15,16]. Thus, in addition to extending the well-established utility of yeast as a model system for eukaryotic biology, the Cas9 system magnifies the value of yeast as a host for engineering heterologous proteins and pathways.

Thus, there remains a need for more efficient and flexible methods of genome editing that enhance repair of RGN-mediated double-strand breaks through the HR mechanism to allow genomes to be modified with precise genetic changes as desired and improved methods for high-throughput production of variant libraries.

SUMMARY

The present disclosure relates to multiplex production and validation of genetically engineered cells using RNA-guided nucleases and barcoding. In particular, high-throughput multiplex genome editing is achieved utilizing a system that facilitates precise genome editing at desired target chromosomal loci by homology directed repair. Integration of guide RNA and donor DNA sequences as a genomic barcode at a chromosomal locus separate from the target loci being edited allows ready identification, isolation, and massively-parallel validation of individual variants from a pool of transformants. Strains can be arrayed according to their precise genetic modifications, as specified by donor DNA incorporation in heterologous or native genes. The present disclosure further relates to a method of editing codons outside of canonical guide RNA recognition regions, which enables complete saturation mutagenesis of protein-coding genes, a marker-based internal cloning method, which removes background due to oligonucleotide synthesis errors and incomplete vector backbone cleavage, and a method of enhancing homology directed repair by active donor recruitment.

Provided herein is a method for multiplex production of genetically engineered cells, the method including: (a) transfecting a plurality of cells with plurality of different recombinant polynucleotides, each recombinant polynucleotide including a genome editing cassette including a first nucleic acid sequence encoding a first guide RNA (gRNA) capable of hybridizing at a genomic target locus to be modified and a donor polynucleotide thereby forming a gRNA-donor polynucleotide combination, where each recombinant polynucleotide includes a different genome editing cassette including a different gRNA-donor polynucleotide combination, and allowing each of the cells to express the first nucleic acid sequence thereby forming the gRNA; and (b) introducing an RNA-guided nuclease into each of the plurality of cells, where the RNA-guided nuclease in each cell forms a complex with the gRNA thereby forming a gRNA-RNA-guided nuclease complex, and allowing the gRNA-RNA-guided nuclease complex to modify the genomic target locus by integrating the donor polynucleotide into the genomic target locus, thereby producing a plurality of genetically engineered cells.

In another aspect is provided a method for multiplex production of genetically engineered cells, the method including: (a) transfecting a plurality of cells with plurality of different recombinant polynucleotides, each recombinant polynucleotide including a unique polynucleotide barcode and a genome editing cassette including a first nucleic acid sequence encoding a first guide RNA (gRNA) capable of hybridizing at a genomic target locus to be modified and a donor polynucleotide thereby forming a gRNA-donor polynucleotide combination, where each recombinant polynucleotide includes a different genome editing cassette including a different gRNA-donor polynucleotide combination, and allowing each of the cells to express the first nucleic acid sequence thereby forming the gRNA; and (b) introducing an RNA-guided nuclease into each of the plurality of cells, where the RNA-guided nuclease in each cell forms a complex with the gRNA thereby forming a gRNA-RNA-guided nuclease complex, and allowing the gRNA-RNA-guided nuclease complex to modify the genomic target locus by integrating the donor polynucleotide into the genomic target locus, thereby producing a plurality of genetically engineered cells.

In embodiments, the method further includes sequence verification and arraying of the plurality of genetically modified cells, the method including: (c) plating the plurality of genetically modified cells in an ordered array on media suitable for growth of the genetically modified cells; (d) culturing the plurality of genetically modified cells under conditions whereby each genetically modified cell produces a colony of clones in the ordered array; (e) introducing a genome editing cassette from a colony in the ordered array into a barcoder cell, where the barcoder cell includes a nucleic acid including a recombination target site for a site-specific recombinase and a barcode sequence that identifies the position of the colony in the ordered array to which the genome editing cassette corresponds; (f) translocating the genome editing cassette to a position adjacent to the barcode sequence of the barcoder cell using a site-specific recombinase system, where site-specific recombination with the recombination target site of the barcoder cell generates a nucleic acid including the barcode sequence linked to the genome editing cassette; (g) sequencing the nucleic acid including the barcode sequence of the barcoder cell linked to the genome editing cassette to identify the sequences of the guide RNA and the donor polynucleotide of the genome editing cassette from the colony, where the barcode sequence of the barcoder cell is used to identify the position of the colony in the ordered array from which the genome editing cassette originated; and (h) picking a clone including the genome editing cassette from the colony in the ordered array identified by the barcode of the barcoder cell.

In another aspect is provided a method for localizing a donor polynucleotide to a genomic target locus in a cell, the method including: (a) transfecting a cell with a recombinant polynucleotide, the recombinant polynucleotide including a genome editing cassette including a donor polynucleotide and a DNA binding sequence known to bind a DNA binding domain; (b) introducing a nuclease into the cell, where the nuclease recognizes and causes a double-strand DNA break at the genomic target locus; (c) introducing a donor recruitment protein into the cell, the donor recruitment protein including the DNA binding domain and a DNA break site localizing domain and allowing the donor recruitment protein to selectively recruit the double-strand DNA break, thereby localizing the donor polynucleotide to the genomic target locus.

In another aspect is provided a library of gene editing vectors, each gene editing vector including a genome editing cassette including (i) a barcode, (ii) a first nucleic acid sequence encoding a first guide RNA (gRNA) capable of hybridizing at a genomic target locus to be modified, and (iii) a donor polynucleotide, thereby forming a barcode-gRNA-donor polynucleotide combination; where each recombinant polynucleotide includes a different genome editing cassette including a different barcode-gRNA-donor polynucleotide combination.

In another aspect is provided a gene editing vector including a donor polynucleotide and a first nucleic acid sequence encoding a first guide RNA (guide X) capable of hybridizing with the vector at a target site such that when the guide X is expressed by a cell, the guide X hybridizes to the vector and creates a double-strand DNA break at the target site.

In another aspect is provided a kit including: (a) a gene editing vector as described herein including embodiments thereof; and (b) a nuclease or a polynucleotide encoding a nuclease.

In another aspect is provided a kit including: (a) a gene editing vector as described herein including embodiments thereof; and (b) a reagent for genetically modifying a cell.

In another aspect is provided a library of gene editing vectors, each gene editing vector comprising a genome editing cassette comprising (i) a first nucleic acid sequence encoding a first guide RNA (gRNA) capable of hybridizing at a genomic target locus to be modified, and (ii) a donor polynucleotide, thereby forming a gRNA-donor polynucleotide combination; wherein each recombinant polynucleotide comprises a different genome editing cassette comprising a different gRNA-donor polynucleotide combination.

In embodiments, each recombinant polynucleotide further comprises a second nucleic acid sequence encoding the RNA-guided nuclease.

In one aspect, the present disclosure includes a method for multiplex genetic modification and barcoding of cells, the method comprising: a) providing a plurality of recombinant polynucleotides, wherein each recombinant polynucleotide comprises a genome editing cassette comprising a polynucleotide encoding a guide RNA (gRNA) capable of hybridizing at a genomic target locus to be modified and a donor polynucleotide comprising a 5' homology arm that hybridizes to a 5' genomic target sequence and a 3' homology arm that hybridizes to a 3' genomic target sequence flanking a nucleotide sequence comprising an intended edit to be integrated into the genomic target locus, wherein each recombinant polynucleotide comprises a different genome editing cassette comprising a different guide RNA-donor polynucleotide combination, such that the plurality of recombinant polynucleotides is capable of producing a plurality of different intended edits at one or more genomic target loci; and b) transfecting the cells with the plurality of recombinant polynucleotides; c) culturing the transfected cells under conditions suitable for transcription, wherein guide RNAs are produced from each genome editing cassette; d) introducing an RNA-guided nuclease into the cells, wherein the RNA-guided nuclease forms complexes with the guide RNAs produced in the cells, said guide RNAs directing the complexes to the one or more genomic target loci, wherein the RNA-guided nuclease creates double-stranded breaks in the genomic DNA of the cells at the one or more genomic target loci, and the donor polynucleotide present in each cell is integrated at the genomic target locus recognized by its 5' homology arm and 3' homology arm by homology directed repair (HDR) such that a plurality of genetically modified cells are produced; and e) barcoding the plurality of genetically modified cells by integrating the genome editing cassette present in each genetically modified cell at a chromosomal barcode locus. In certain embodiments, the method further comprises performing additional rounds of genetic modification and genomic barcoding on the genetically modified cells by repeating steps (a)-(e) using different genome editing cassettes.

In certain embodiments, each recombinant polynucleotide is provided by a vector. The vector can be, for example, a plasmid or viral vector. In certain embodiments, the vector is a high copy number vector.

In certain embodiments, each recombinant polynucleotide is provided as linear DNA. For example, the method may further comprise amplifying a recombinant polynucleotide comprising a genome editing cassette, which is provided as a PCR product.

In certain embodiments, the RNA-guided nuclease is also provided by a vector. In certain embodiments, the genome editing cassette and the RNA-guided nuclease are provided by a single vector or separate vectors. In another embodiment, a recombinant polynucleotide encoding the RNA-guided nuclease is integrated into the genome of the host cells.

Transcription of a guide RNA will generally depend on the presence of a promoter, which may be included in the genome editing cassette, or in a vector or at a chromosomal locus (e.g., the chromosomal barcode locus) in which the genome editing cassette is inserted. The promoter may be a constitutive or an inducible promoter. In certain embodiments, each genome editing cassette comprises a promoter operably linked to the polynucleotide encoding the guide RNA. In other embodiments, the chromosomal barcode locus comprises a promoter that becomes operably linked to the polynucleotide encoding the guide RNA of any genome editing cassette that integrates at the chromosomal barcode locus. In another embodiment, each recombinant polynucleotide is provided by a vector, wherein the vector comprises a promoter that is operably linked to the polynucleotide encoding the guide RNA.

In certain embodiments, the plurality of recombinant polynucleotides is capable of producing mutations at multiple sites within a single gene. In other embodiments, the plurality of recombinant polynucleotides is capable of producing mutations at multiple sites in different genes or anywhere in the genome. For example, each donor polynucleotide may introduce a different mutation into a gene, such as an insertion, deletion, or substitution. In another embodiment, at least one donor polynucleotide introduces a mutation that inactivates a gene. In another embodiment, at least one donor polynucleotide removes a mutation from a gene. In another embodiment, at least one donor polynucleotide inserts a precise genetic change into the genomic DNA.

In certain embodiments, integration of the genome editing cassette present in a genetically modified cell at the chromosomal barcode locus is performed using HDR. Each recombinant polynucleotide may further comprise a pair of universal homology arms flanking the genome editing cassette that are capable of hybridizing to complementary sequences at the chromosomal barcode locus to allow said integration of the genome editing cassette at the chromosomal barcode locus by the HDR. In addition, each recombinant polynucleotide may further comprise a second guide RNA capable of hybridizing at the chromosomal barcode locus, wherein the RNA-guided nuclease further forms a complex with the second guide RNA, said second guide RNA directing said complex to the chromosomal barcode locus, wherein the RNA-guided nuclease creates a double-stranded break at the chromosomal barcode locus, and the genome editing cassette is integrated into the chromosomal barcode locus by the HDR.

In other embodiments, integration of the genome editing cassette present in a genetically modified cell at the chromosomal barcode locus is performed using a site-specific recombinase system. Exemplary site-specific recombinase systems include a Cre-loxP site-specific recombinase system, a Flp-FRT site-specific recombinase system, a PhiC31-att site-specific recombinase system, and a Dre-rox site-specific recombinase system. In certain embodiments, the chromosomal barcode locus further comprises a first recombination target site for a site-specific recombinase and the recombinant polynucleotide further comprises a second recombination target site for the site-specific recombinase, and site-specific recombination between the first recombination target site and the second site-specific recombination site results in said integrating of the genome editing cassette at the chromosomal barcode locus.

In certain embodiments, the method further comprises using a selectable marker that selects for clones that have undergone successful integration of the donor polynucleotide at the genomic target locus or successful integration of the genome editing cassette at the chromosomal barcode locus.

In certain embodiments, the cells to be genetically modified are eukaryotic or prokaryotic. In some embodiments, the cells are yeast cells, which can be haploid or diploid yeast cells.

In certain embodiments, each recombinant polynucleotide further comprises a pair of restriction sites flanking the genome editing cassette. In some embodiments, the restriction sites are recognized by a meganuclease (e.g., SceI) that generates a DNA double-strand break. The expression of the meganuclease may be controlled by an inducible promoter.

In another embodiment, the genome editing cassette further comprises a tRNA sequence at the 5' end of the nucleotide sequence encoding the guide RNA.

In another embodiment, the genome editing cassette further comprises a nucleotide sequence encoding a hepatitis delta virus (HDV) ribozyme at the 5' end of the nucleotide sequence encoding the guide RNA.

In another embodiment, the RNA-guided nuclease is a Cas nuclease (e.g., Cas9 or Cpf1) or an engineered RNA-guided FokI-nuclease.

In another embodiment, the genome editing cassette is flanked by restriction sites recognized by a meganuclease.

In certain embodiments, each genome editing cassette further comprises a unique barcode sequence for identifying the guide RNA and the donor polynucleotide encoded by each genome editing cassette. The unique barcode can be sequenced in place of the guide RNA and the donor polynucleotide to identify a genetic modification to a cell. In another embodiment, the method further comprises deleting the polynucleotide encoding the guide RNA and the donor polynucleotide integrated at the chromosomal barcode locus while retaining the unique barcode at said chromosomal barcode locus that represents the deleted sequences. In another embodiment, the method further comprises sequencing the barcode at the chromosomal barcode locus of at least one genetically modified cell to identify the genome editing cassette used in genetically modifying said cell.

In certain embodiments, the method further comprises sequencing each genome editing cassette. Sequencing of a genome editing cassette to link a barcode to a particular gRNA-donor polynucleotide combination may be performed, for example, at an intermediate cloning step prior to ligation of a genome editing cassette into a vector or prior to transfecting cells. Alternatively or additionally, sequencing of a genome editing cassette that has been integrated at the chromosomal barcode locus may be used to determine genome edits performed on a genetically modified cell.

In certain embodiments, the method further comprises sequence verification and arraying of the plurality of genetically modified cells, the method comprising: a) plating the plurality of genetically modified cells in an ordered array on media suitable for growth of the genetically modified cells; b) culturing the plurality of genetically modified cells under conditions whereby each genetically modified cell produces a colony of clones in the ordered array; c) introducing a genome editing cassette from a colony in the ordered array into a barcoder cell, wherein the barcoder cell comprises a nucleic acid comprising a recombination target site for a site-specific recombinase and a barcode sequence that identifies the position of the colony in the ordered array to which the genome editing cassette corresponds; d) translocating the genome editing cassette to a position adjacent to the barcode sequence of the barcoder cell using a site-specific recombinase system, wherein site-specific recombination with the recombination target site of the barcoder cell generates a nucleic acid comprising the barcode sequence linked to the genome editing cassette; e) sequencing the nucleic acid comprising the barcode sequence of the barcoder cell linked to the genome editing cassette to identify the sequences of the guide RNA and the donor polynucleotide of the genome editing cassette from the colony, wherein the barcode sequence of the barcoder cell is used to identify the position of the colony in the ordered array from which the genome editing cassette originated; and f) picking a clone comprising the genome editing cassette from the colony in the ordered array identified by the barcode of the barcoder cell.

For example, the genetically modified cells may be haploid yeast cells and the barcoder cells may be haploid yeast cells capable of mating with the genetically modified cells, wherein introducing a genome editing cassette from a genetically modified haploid yeast colony in the ordered array into a barcoder haploid yeast cell comprises mating the haploid yeast clone from the colony with the barcoder haploid yeast cell to produce a diploid yeast cell. Subsequent site-specific recombination, as described herein, generates a nucleic acid comprising the barcode sequence linked to the genome editing cassette in the diploid yeast cell. The genetically modified cells may be strain MATα and the barcoder yeast cells may be strain MATa. Alternatively, the genetically modified cells may be strain MATa and the barcoder yeast cells may be strain MATα.

In certain embodiments, the recombinase system in the barcoder cell is a Cre-loxP site-specific recombinase system, a Flp-FRT site-specific recombinase system, a PhiC31-att site-specific recombinase system, or a Dre-rox site-specific recombinase system. In one embodiment, the recombination target site of the barcoder cell comprises a loxP recombination site.

In another embodiment, the recombinase system in the barcoder cell uses a meganuclease to generate a DNA double-strand break. In another embodiment, the meganuclease in the barcoder cell is a galactose inducible SceI meganuclease. In another embodiment, the genome editing cassette is flanked by restriction sites recognized by the meganuclease.

In another embodiment, the method further comprises using a selectable marker that selects for clones that have undergone successful site-specific recombination.

In certain embodiments, the method further comprises inhibiting non-homologous end joining (NHEJ). For example, NHEJ may be inhibited by contacting cells with a small molecule inhibitor selected from the group consisting of wortmannin and Scr7. Alternatively, RNA interference or CRISPR-interference can be used to inhibit expression of a protein component of the NHEJ pathway.

In other embodiments, the method further comprises using an HDR enhancer or active donor recruitment to increase the frequency of HDR in the cells.

In another embodiment, the method further comprises using a selectable marker that selects for clones that have undergone successful integration of the donor polynucleotides at the one or more genomic target loci by HDR.

In another embodiment, the method further comprises phenotyping at least one clone in the ordered array.

In another embodiment, the method further comprises sequencing an entire genome of at least one clone in the ordered array.

In another embodiment, the method further comprises repeating steps (a)-(e) with all the colonies in the ordered array to identify the sequences of the guide RNAs and the donor polynucleotides of the genome editing cassettes for every colony in the ordered array.

In another aspect, the present disclosure includes an ordered array of colonies comprising clones of the genetically modified cells produced by the methods described herein, wherein the colonies are indexed according to the verified sequences of their guide RNAs and donor polynucleotides.

In another aspect, the present disclosure includes a kit for multiplex genetic modification and barcoding of cells, the kit comprising: a) a plurality of recombinant polynucleotides, wherein each recombinant polynucleotide comprises a genome editing cassette comprising a polynucleotide encoding a guide RNA (gRNA) capable of hybridizing at a genomic target locus to be modified and a donor polynucleotide comprising a 5' homology arm that hybridizes to a 5' genomic target sequence and a 3' homology arm that hybridizes to a 3' genomic target sequence flanking a nucleotide sequence comprising an intended edit to be integrated into the genomic target locus, wherein each recombinant polynucleotide comprises a different genome editing cassette comprising a different guide RNA-donor polynucleotide combination, such that the plurality of recombinant polynucleotides is capable of producing a plurality of different intended edits at one or more genomic target loci; and b) an RNA-guided nuclease; and c) cells comprising a chromosomal barcode locus, wherein the barcode locus comprises a site for integration of the genome editing cassette of at least one recombinant polynucleotide. The kit may further comprise other reagents and instructions for performing genome editing and barcoding as described herein.

In certain embodiments, each recombinant polynucleotide in the kit further comprises a pair of universal homology arms flanking the genome editing cassette that are capable of hybridizing to complementary sequences at the site for integration at the chromosomal barcode locus to allow said integration of the genome editing cassette at the chromosomal barcode locus by homology directed repair (HDR).

In another embodiment, each recombinant polynucleotide further comprises a second guide RNA capable of hybridizing at the chromosomal barcode locus.

In certain embodiments, the kit further comprises a site-specific recombinase system (e.g., a Cre-loxP site-specific recombinase system, a Flp-FRT site-specific recombinase system, a PhiC31-att site-specific recombinase system, or a Dre-rox site-specific recombinase system). In another embodiment, the chromosomal barcode locus further comprises a first recombination target site for a site-specific recombinase and the recombinant polynucleotide further comprises a second recombination target site for the site-specific recombinase, such that site-specific recombination can occur between the first recombination target site and the second site-specific recombination site to allow said integration of the genome editing cassette at the chromosomal barcode locus.

In another embodiment, the RNA-guided nuclease in the kit is a Cas nuclease (e.g., Cas9 or Cpf1) or an engineered RNA-guided FokI-nuclease.

In certain embodiments, the kit further comprises a fusion protein designed to carry out donor recruitment as described herein. Such a fusion protein comprises a polypeptide comprising a nucleic acid binding domain connected to a protein that selectively binds to a DNA break generated by the RNA-guided nuclease. In another embodiment, the donor polynucleotide further comprises a nucleotide sequence sufficiently complementary to hybridize to a sequence adjacent to the DNA break, and a nucleotide sequence comprising a binding site recognized by the nucleic acid binding domain of the fusion protein. In certain embodiments, the nucleic acid binding domain is a LexA DNA binding domain and the binding site is a LexA binding site or the nucleic acid binding domain is a forkhead homolog 1 (FKH1) DNA binding domain and the binding site is a FKH1 binding site. In some embodiments, the polypeptide comprising the nucleic acid binding domain further comprises a forkhead-associated (FHA) phosphothreonine-binding domain. In another embodiment, the polypeptide comprising the nucleic acid binding domain comprises a LexA DNA binding domain linked to a FHA phosphothreonine-binding domain.

In another aspect, the present disclosure includes a method of promoting homology directed repair (HDR) by active donor recruitment to a DNA break, the method comprising: a) introducing into a cell a donor recruitment protein comprising a polypeptide that selectively binds to the DNA break connected to a polypeptide comprising a nucleic acid binding domain; and b) introducing into the cell a donor polynucleotide comprising i) a nucleotide sequence sufficiently complementary to hybridize to a sequence adjacent to the DNA break, and ii) a nucleotide sequence comprising a binding site recognized by the nucleic acid binding domain of the fusion protein, wherein the nucleic acid binding domain selectively binds to the binding site on the donor polynucleotide to produce a complex between the donor polynucleotide and the fusion protein, thereby recruiting the donor polynucleotide to the DNA break and promoting HDR. In an embodiment, the donor recruitment protein is a fusion protein.

In certain embodiments, the protein that is recruited to the DNA break is an RNA-guided nuclease, such as a Cas nuclease (e.g., Cas9 or Cpf1 nuclease) or an engineered RNA-guided FokI-nuclease.

In certain embodiments, the DNA break is a single-stranded or double-stranded DNA break. If the DNA break is a single-stranded DNA break, the fusion protein comprises a protein that selectively binds to the single-stranded DNA break. If the DNA break is a double-stranded DNA break, the fusion protein comprises a protein that selectively binds to the double-stranded DNA break.

In certain embodiments, the donor polynucleotide is single-stranded or double-stranded.

In another embodiment, the nucleic acid binding domain is an RNA-binding domain and the binding site comprises an RNA sequence recognized by the RNA binding domain.

In another embodiment, the nucleic acid binding domain of the donor recruitment protein is a DNA-binding domain and the binding site comprises a DNA sequence recognized by the DNA binding domain. In one embodiment, the DNA binding domain is a LexA DNA binding domain, and the binding site is a LexA binding site. In another embodiment, the DNA binding domain is a forkhead homolog 1 (FKH1) DNA binding domain, and the binding site is a FKH1 binding site.

In another embodiment, the polypeptide comprising the nucleic acid binding domain (donor recruitment protein) further comprises a forkhead-associated (FHA) phosphothreonine-binding domain, wherein the donor polynucleotide is selectively recruited to a DNA break having a protein comprising a phosphorylated threonine residue located sufficiently close to the DNA break for the FHA phosphothreonine-binding domain to bind to the phosphorylated threonine residue. In a further embodiment, the polypeptide comprising the nucleic acid binding domain comprises a LexA DNA binding domain linked to a FHA phosphothreonine-binding domain.

In another embodiment, the donor polynucleotide is provided by a recombinant polynucleotide comprising a promoter operably linked to the donor polynucleotide. In another embodiment, the fusion protein is provided by a recombinant polynucleotide comprising a promoter operably linked to a polynucleotide encoding the fusion protein. In certain embodiments, the donor polynucleotide and the fusion protein are provided by a single vector or separate vectors. In another embodiment, at least one vector is a viral vector or a plasmid.

In certain embodiments, the donor polynucleotide is RNA or DNA. In another embodiment, the method further comprises reverse transcribing a donor polynucleotide comprising RNA with reverse transcriptase to produce a donor polynucleotide comprising DNA.

In certain embodiments, the DNA break is created by a site-specific nuclease, such as, but not limited to, a Cas nuclease (e.g., Cas9 or Cpf1), an engineered RNA-guided FokI-nuclease, a meganuclease, a zinc finger nuclease (ZFN), and a transcription activator-like effector-based nuclease (TALEN).

These and other embodiments of the subject disclosure will readily occur to those of skill in the art in view of the disclosure herein.

BRIEF DESCRIPTION OF THE FIGURES

FIG. 1A shows guide RNA (gRNA)-donor DNA sequences cloned into a high-copy vector, with the tRNA-HDV ribozyme promoter driving gRNA expression. The guide-donor plasmids were then transformed into cells with Cas9 pre-expressed from a strong constitutive promoter. FIG. 1B shows target locus editing. Cas9-gRNA-induced dsDNA breaks are resolved through either donor DNA directed HR, NHEJ, or cell death. FIG. 1C shows REDI locus barcoding. Induction of SceI with galactose enables replacement of counter-selectable FCY1 with the guide RNA-donor DNA segment, allowing for (1) PCR-based phenotyping of competitively grown pools, and (2) REDI-based identification of individual variants.

FIGS. 2A-2C show proof-of-concept for high-efficiency Cas9 editing and SceI-mediated barcoding. FIG. 2A shows a gRNA targeting ADE2 cloned into the high copy vector backbone shown in FIG. 1 without (left column) or with (right column) donor DNA. The gRNA vectors were transformed into cells with pre-expressed Cas9 (top row), or with PTEF1-Cas9 encoded on the gRNA vector (not pre-expressed; bottom row). FIG. 2B shows the ADE2 locus in select clones. Sequencing confirmed the desired loss-of-function edit. FIG. 2C shows results for pooled cells from the plate, which were either shifted to galactose or glucose media. Individual colonies were isolated and screened for the integration of the guide-donor cassette at the REDI locus, which was confirmed by Sanger sequencing.

FIG. 4A shows a two plasmid-based system for high-throughput editing in the absence of donor recruitment. FIG. 4B shows that random diffusion of donor DNA results in inefficient homologous recombination repair, and the majority of transformants with effective gRNAs undergo cell death. FIG. 4C shows a modified two plasmid-based system with LexA binding sites on the guide-donor plasmid and a LexA DNA-binding domain (DBD) fused to the Fkh1 protein for ultra-high efficiency high-throughput editing. FIG. 4D shows dsDNA breaks trigger the phosphorylation of threonine residues on endogenous cellular proteins in the vicinity of the break. This results in the recruitment of Fkh1 via its forkhead-associated (FHA) phosphothreonine-binding domain, resulting in a high local concentration of donor DNA to facilitate the search for homologous DNA during DNA repair. This leads to precision editing being the predominant outcome over cell death. FIG. 4E shows a LexA DNA binding domain fused to Cas9 instead of Fkh1. FIG. 4F shows that the Cas9-LexA DBD enables pre-recruitment of the guide-donor plasmid to the gRNA target site, facilitating HDR after DNA cleavage by Cas9.

FIG. 5A shows cells pre-expressing Cas9 (upper left panel, as in FIG. 4A) or Cas9 and LexA DBD-Fkh1 (upper right panel, as in FIG. 4C) were transformed with a plasmid pool harboring 85% sequence-verified guide-donor targeting a null mutation in ADE2, and 15% of the same plasmid with a mutated ADE2 guide RNA. FIG. 5B shows cells pre-expressing Cas9, transformed with the sequence-perfect guide-donor (lower left panel). Cells pre-expressing the high-copy guide-donor plasmid were transformed with the Cas9 plasmid (lower right panel).

FIG. 6A shows steps 1-4 of the process. Step 1: a complex library of plasmids harboring guide RNA (gRNA) and donor DNA sequences is transformed into recipient strains modified to contain a barcode locus with a counter-selectable marker (FCY1) flanked by sites for the mega-nuclease SceI. Transformed cells are plated onto -HIS to select for plasmids containing the correct internal cloning event, and colonies pooled and grown to mid-log phase in rich medium containing G418 to maintain selection for the guide-donor plasmids. The cells are then transformed with the Cas9/SceI plasmid and plated onto -LEU-HIS Step 2: The chromosomal target will be cut with the Cas9-gRNA and repaired using homologous recombination (HR) with the donor DNA encoded on the plasmid. The colonies are recovered and grown for several generations in rich medium with galactose to induce SceI. dsDNA breaks at the chromosomal barcode locus promote integration of the guide-HIS3-donor cassette, and linearize the plasmids. Step 3: Successful integration of guide-donor barcodes and loss of plasmids is selected for by plating on synthetic medium containing 5-fluoro-cytosine (5-FC). Transformants are arrayed on agar plates at a density of 1536, to allow subsequent mating to barcoder strains. At this stage, it is possible that transformants contain successful intended edits, unintended mutations due to oligo synthesis-derived errors, or no edit. Step 4: The arrayed strain variants are mated to barcoder strains, which contain a LoxP site, followed by a unique positional barcode that specifies the colony coordinates on the plate, and the rest of the URA3 gene. Induction of Cre results in LoxP-mediated reconstitution of the split URA3, which physically links the guide-donor sequence with the positional barcode for high-throughput paired-end sequencing (HTS) of the guide-donor-barcode combinations (Step 5). Two different P5 primers allow linkage of the guide and donor sequence to the specific colony coordinates by virtue of the shared positional barcode. FIG. 6B shows schematics of the Mat a variant chromosome and the Mat α barcoded chromosome and the results of Step 4 and Step 5.

FIG. 7A shows clones isolated from multiplexed precision editing experiments can contain successfully edited target loci (dark gray), an unintended mutation at the target locus due to a synthesis-derived error or error during homologous recombination (HR) (light gray), or an unsuccessful edit due to an ineffective guide RNA (light gray). FIG. 7B shows independent clones for each designed variant (as indicated by light gray, dark gray, and medium gray). Step 1: These replicates are re-arrayed onto separate plates such that each plate contains mutations targeted within a designated chromosomal window or gene, and only one colony is present per designed variant per plate. Colonies are pooled and genomic DNA extracted for each plate. Step 2: PCR of the targeted chromosomal locus and deep amplicon sequencing are performed. Successfully edited variants are expected to be present at a frequency of 1/1536. FIG. 7C depicts rearraying of desired clones for pooled (top) or spatially-separated phenotyping assays.

FIGS. 10A and 10B show a synonymous codon spreading strategy to enable amino acid mutations outside of a guide recognition region. Saturation mutagenesis of open reading frames is enabled through engineering synonymous codon mutations (dark gray) between the nonsynonymous variant (light gray) and the protospacer-adjacent motif (PAM, box, NGG in this depiction). A pseudo-WT control is established by including only the synonymous variants (dark gray). Also shown are donor DNA and guide RNA sequences to engineer a nonsynonymous variant falling within (FIG. 10A) or outside of (FIG. 10B) the guide recognition sequence.

FIG. 14A: A Cpf1 guide-donor plasmid (the guide has the Cpf1 scaffold) targeting the ADE2 gene was transformed into cells pre-expressing Cpf1. The donor DNA encodes a frameshift-causing deletion. FIG. 14B: The Cpf1 guide-donor was mixed with a non-editing plasmid at a ratio of 17:3 and transformed into cells expressing Cpf1 without (left) or with (right) LexA-FHA. The ratio of red:white colonies is shown on the y-axis.

DETAILED DESCRIPTION

Figure 1A:
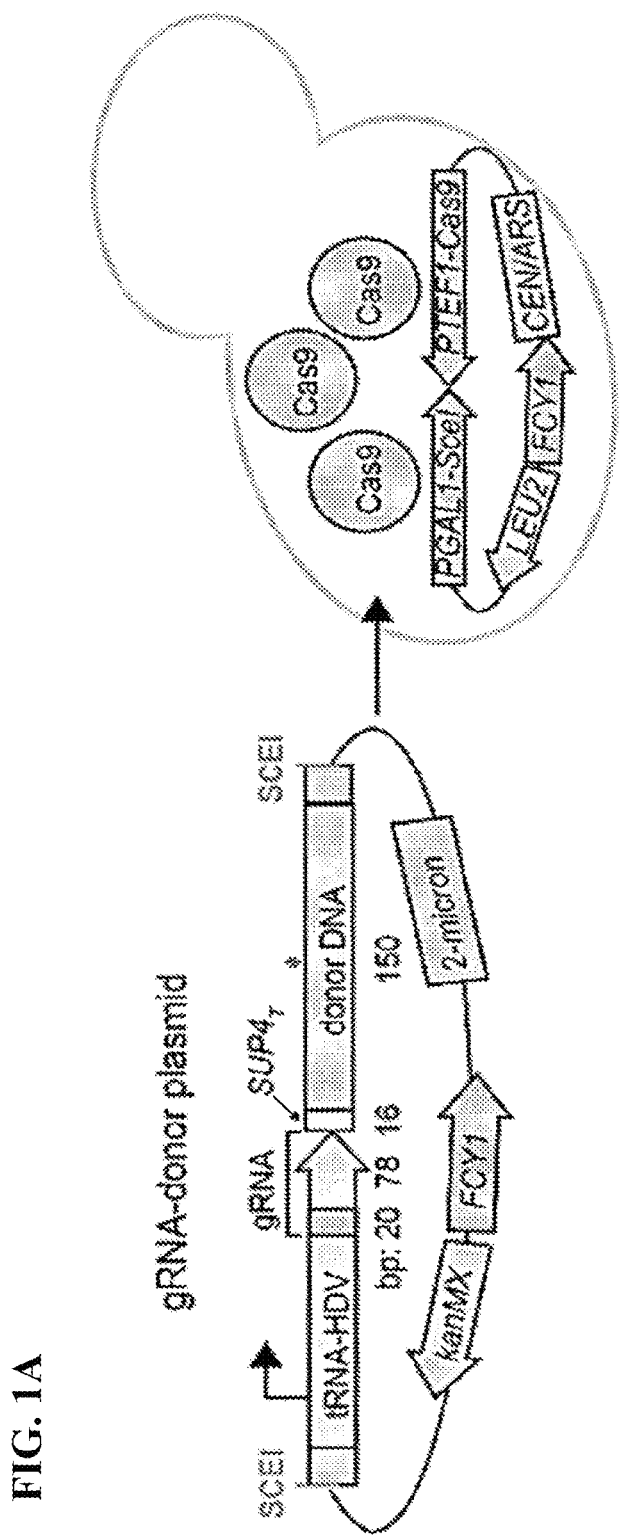
FIGS. 1A-1C show a dual CRISPR/Cas9 editing and barcoding system.

The practice of the present disclosure will employ, unless otherwise indicated, conventional methods of genome editing, biochemistry, chemistry, immunology, molecular biology and recombinant DNA techniques within the skill of the art. Such techniques are explained fully in the literature. See, e.g., *Targeted Genome Editing Using Site-Specific Nucleases: ZFNs, TALENs, and the CRISPR/Cas9 System* (T. Yamamoto ed., Springer, 2015); *Genome Editing: The Next Step in Gene Therapy* (Advances in Experimental Medicine and Biology, T. Cathomen, M. Hirsch, and M. Porteus eds., Springer, 2016); Aachen Press *Genome Editing* (CreateSpace Independent Publishing Platform, 2015); *Handbook of Experimental Immunology*, Vols. I-IV (D. M. Weir and C. C. Blackwell eds., Blackwell Scientific Publications); A. L. Lehninger, *Biochemistry* (Worth Publishers, Inc., current addition); Sambrook, et al., *Molecular Cloning: A Laboratory Manual* (3$^{rd}$ Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

I. DEFINITIONS

In describing the present disclosure, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a cell" includes a mixture of two or more cells, and the like.

The term "about," particularly in reference to a given quantity, is meant to encompass deviations of plus or minus five percent.

A "barcode" refers to one or more nucleotide sequences that are used to identify a nucleic acid or cell with which the barcode is associated. Barcodes can be 3-1000 or more nucleotides in length, preferably 10-250 nucleotides in length, and more preferably 10-30 nucleotides in length, including any length within these ranges, such as 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 200, 300, 400, 500, 600, 700, 800, 900, or 1000 nucleotides in length. Barcodes may be used, for example, to identify a single cell, subpopulation of cells, colony, or sample from which a nucleic acid originated. Barcodes may also be used to identify the position (i.e., positional barcode) of a cell, colony, or sample from which a nucleic acid originated, such as the position of a colony in a cellular array, the position of a well in a multi-well plate, or the position of a tube, flask, or other container in a rack. In particular, a barcode may be used to identify a genetically modified cell from which a nucleic acid originated. In some embodiments, a barcode is used to identify a particular type of genome edit. For example, a guide RNA-donor polynucleotide cassette itself can be used as a barcode to identify a genetically modified cell from which a nucleic acid originated. Alternatively, a unique barcode may be used to identify each guide-RNA-donor polynucleotide cassette used in multiplex genome editing. Furthermore, multiple barcodes can be used in combination to identify different features of a nucleic acid. For example, positional barcoding (e.g., to identify the position of a cell, colony, culture, or sample in an array, multi-well plate, or rack) can be combined with barcodes identifying guide-RNA-donor polynucleotide cassettes used in genome editing. In some embodiments, barcodes are inserted into a nucleic acid (e.g., at a "barcode locus") at each round of genome editing to identify the guide-RNAs and/or donor polynucleotides used in genetic modification of a cell.

The term "barcoder cell" refers to a cell comprising a nucleic acid comprising a barcode sequence. In one embodiment, the barcode identifies the position of a colony comprising the barcoder cells.

The terms "polypeptide" and "protein" refer to a polymer of amino acid residues and are not limited to a minimum length. Thus, peptides, oligopeptides, dimers, multimers, and the like, are included within the definition. Both full length proteins and fragments thereof are encompassed by the definition. The terms also include post expression modifications of the polypeptide, for example, glycosylation, acetylation, phosphorylation, hydroxylation, and the like. Furthermore, for purposes of the present disclosure, a "polypeptide" refers to a protein which includes modifications, such as deletions, additions and substitutions to the native sequence, so long as the protein maintains the desired activity. These modifications may be deliberate, as through site directed mutagenesis, or may be accidental, such as through mutations of hosts which produce the proteins or errors due to PCR amplification.

The term "Cas9" as used herein encompasses type II clustered regularly interspaced short palindromic repeats (CRISPR) system Cas9 endonucleases from any species, and also includes biologically active fragments, variants, analogs, and derivatives thereof that retain Cas9 endonuclease activity (i.e., catalyze site-directed cleavage of DNA to generate double-strand breaks). A Cas9 endonuclease binds to and cleaves DNA at a site comprising a sequence complementary to its bound guide RNA (gRNA).

A Cas9 polynucleotide, nucleic acid, oligonucleotide, protein, polypeptide, or peptide refers to a molecule derived from any source. The molecule need not be physically derived from an organism, but may be synthetically or recombinantly produced. Cas9 sequences from a number of bacterial species are well known in the art and listed in the National Center for Biotechnology Information (NCBI) database. See, for example, NCBI entries for Cas9 from: *Streptococcus pyogenes* (WP_002989955, WP_038434062, WP_011528583); *Campylobacter jejuni* (WP_022552435, YP_002344900), *Campylobacter coli* (WP_060786116); *Campylobacter fetus* (WP_059434633); *Corynebacterium ulcerans* (NC_015683, NC_017317); *Corynebacterium diphtheria* (NC_016782, NC_016786); *Enterococcus faecalis* (WP_033919308); *Spiroplasma syrphidicola* (NC_021284); *Prevotella intermedia* (NC_017861); *Spiroplasma taiwanense* (NC_021846); *Streptococcus iniae* (NC_021314); *Belliella baltica* (NC_018010); *Psychroflexus torquisI* (NC_018721); *Streptococcus thermophilus* (YP_820832), *Streptococcus mutans* (WP_061046374, WP_024786433); *Listeria innocua* (NP_472073); *Listeria monocytogenes* (WP_061665472); *Legionella pneumophila* (WP_062726656); *Staphylococcus aureus* (WP_001573634); *Francisella tularensis* (WP_032729892, WP_014548420), *Enterococcus faecalis* (WP_033919308); *Lactobacillus rhamnosus* (WP_048482595, WP_032965177); and *Neisseria meningitidis* (WP_061704949, YP_002342100); all of which sequences (as entered by the date of filing of this application) are herein incorporated by reference. Any of these sequences or a variant thereof comprising a sequence having at least about 70-100% sequence identity thereto, including any percent identity within this range, such as 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity thereto, can be used for genome editing, as described herein, wherein the variant retains biological activity, such as Cas9 site-directed endonuclease activity. See also Fonfara et al. (2014) Nucleic Acids Res. 42(4):2577-90; Kapitonov et al. (2015) J. Bacteriol. 198(5):797-807, Shmakov et al. (2015) Mol. Cell. 60(3):385-397, and Chylinski et al. (2014) Nucleic Acids Res. 42(10):6091-6105); for sequence comparisons and a discussion of genetic diversity and phylogenetic analysis of Cas9.

By "derivative" is intended any suitable modification of the native polypeptide of interest, of a fragment of the native polypeptide, or of their respective analogs, such as glycosylation, phosphorylation, polymer conjugation (such as with polyethylene glycol), or other addition of foreign moieties, as long as the desired biological activity of the native polypeptide is retained. Methods for making polypeptide fragments, analogs, and derivatives are generally available in the art.

By "fragment" is intended a molecule consisting of only a part of the intact full-length sequence and structure. The fragment can include a C-terminal deletion an N-terminal deletion, and/or an internal deletion of the polypeptide. Active fragments of a particular protein or polypeptide will generally include at least about 5-10 contiguous amino acid residues of the full length molecule, preferably at least about 15-25 contiguous amino acid residues of the full length molecule, and most preferably at least about 20-50 or more contiguous amino acid residues of the full length molecule, or any integer between 5 amino acids and the full length sequence, provided that the fragment in question retains biological activity, such as Cas9 site-directed endonuclease activity.

"Substantially purified" generally refers to isolation of a substance (compound, polynucleotide, nucleic acid, protein, polypeptide, polypeptide composition) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

As used herein, the phrase "heterogeneous population of cells" refers to a mixture of at least two types of cells, one type being the cells of interest (e.g., having a genomic modification of interest). The heterogeneous population of cells may be derived from any organism.

The terms "isolating" and "isolation," as used herein in the context of selecting a cell or population of cells having a genomic modification of interest, refer to separating a cell or population of cells having the genomic modification of interest from a heterogeneous population of cells, such as by positive or negative selection.

The term "selection marker" refers to a marker which can be used for identification or enrichment of a cell population from a heterogeneous population of cells, either by positive selection (selecting cells expressing the marker) or by negative selection (excluding cells expressing the marker).

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, microRNA, DNA:RNA hybrids, and hybrids between PNAs and DNA or RNA, and also include known types of modifications, for example, labels which are known in the art, methylation, "caps," substitution of one or more of the naturally occurring nucleotides with an analog (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. The term also includes locked nucleic acids (e.g., comprising a ribonucleotide that has a methylene bridge between the 2'-oxygen atom and the 4'-carbon atom). See, for example, Kurreck et al. (2002) Nucleic Acids Res. 30: 1911-1918; Elayadi et al. (2001) Curr. Opinion Invest. Drugs 2: 558-561; Orum et al. (2001) Curr. Opinion Mol. Ther. 3: 239-243; Koshkin et al. (1998) Tetrahedron 54: 3607-3630; Obika et al. (1998) Tetrahedron Lett. 39: 5401-5404.

The terms "hybridize" and "hybridization" refer to the formation of complexes between nucleotide sequences which are sufficiently complementary to form complexes via Watson-Crick base pairing.

The term "homologous region" refers to a region of a nucleic acid with homology to another nucleic acid region. Thus, whether a "homologous region" is present in a nucleic acid molecule is determined with reference to another nucleic acid region in the same or a different molecule.

Further, since a nucleic acid is often double-stranded, the term "homologous, region," as used herein, refers to the ability of nucleic acid molecules to hybridize to each other. For example, a single-stranded nucleic acid molecule can have two homologous regions which are capable of hybridizing to each other. Thus, the term "homologous region" includes nucleic acid segments with complementary sequences. Homologous regions may vary in length, but will typically be between 4 and 500 nucleotides (e.g., from about 4 to about 40, from about 40 to about 80, from about 80 to about 120, from about 120 to about 160, from about 160 to about 200, from about 200 to about 240, from about 240 to about 280, from about 280 to about 320, from about 320 to about 360, from about 360 to about 400, from about 400 to about 440, etc.).

As used herein, the terms "complementary" or "complementarity" refers to polynucleotides that are able to form base pairs with one another. Base pairs are typically formed by hydrogen bonds between nucleotide units in an anti-parallel orientation between polynucleotide strands. Complementary polynucleotide strands can base pair in a Watson-Crick manner (e.g., A to T, A to U, C to G), or in any other manner that allows for the formation of duplexes. As persons skilled in the art are aware, when using RNA as opposed to DNA, uracil (U) rather than thymine (T) is the base that is considered to be complementary to adenosine. However, when a uracil is denoted in the context of the present disclosure, the ability to substitute a thymine is implied, unless otherwise stated. "Complementarity" may exist between two RNA strands, two DNA strands, or between a RNA strand and a DNA strand. It is generally understood that two or more polynucleotides may be "complementary" and able to form a duplex despite having less than perfect or less than 100% complementarity. Two sequences are "perfectly complementary" or "100% complementary" if at least a contiguous portion of each polynucleotide sequence, comprising a region of complementarity, perfectly base pairs with the other polynucleotide without any mismatches or interruptions within such region. Two or more sequences are considered "perfectly complementary" or "100% complementary" even if either or both polynucleotides contain additional non-complementary sequences as long as the contiguous region of complementarity within each polynucleotide is able to perfectly hybridize with the other. "Less than perfect" complementarity refers to situations where less than all of the contiguous nucleotides within such region of complementarity are able to base pair with each other. Determining the percentage of complementarity between two polynucleotide sequences is a matter of ordinary skill in the art. For purposes of Cas9 targeting, a gRNA may comprise a sequence "complementary" to a target sequence (e.g., major or minor allele), capable of sufficient base-pairing to form a duplex (i.e., the gRNA hybridizes with the target sequence). Additionally, the gRNA may comprise a sequence complementary to a PAM sequence, wherein the gRNA also hybridizes with the PAM sequence in a target DNA.

A "target site" or "target sequence" is the nucleic acid sequence recognized (i.e., sufficiently complementary for hybridization) by a guide RNA (gRNA) or a homology arm of a donor polynucleotide. The target site may be allele-specific (e.g., a major or minor allele).

The term "donor polynucleotide" refers to a polynucleotide that provides a sequence of an intended edit to be integrated into the genome at a target locus by HDR.

By "homology arm" is meant a portion of a donor polynucleotide that is responsible for targeting the donor polynucleotide to the genomic sequence to be edited in a cell. The donor polynucleotide typically comprises a 5' homology arm that hybridizes to a 5' genomic target sequence and a 3' homology arm that hybridizes to a 3' genomic target sequence flanking a nucleotide sequence comprising the intended edit to the genomic DNA. The homology arms are referred to herein as 5' and 3' (i.e., upstream and downstream) homology arms, which relates to the relative position of the homology arms to the nucleotide sequence comprising the intended edit within the donor polynucleotide. The 5' and 3' homology arms hybridize to regions within the target locus in the genomic DNA to be modified, which are referred to herein as the "5' target sequence" and "3' target sequence," respectively. The nucleotide sequence comprising the intended edit is integrated into the genomic DNA by HDR at the genomic target locus recognized (i.e., sufficiently complementary for hybridization) by the 5' and 3' homology arms.

"Administering" a nucleic acid, such as a donor polynucleotide, guide RNA, or Cas9 expression system to a cell comprises transducing, transfecting, electroporating, translocating, fusing, phagocytosing, shooting or ballistic methods, etc., i.e., any means by which a nucleic acid can be transported across a cell membrane.

By "selectively binds" with reference to a guide RNA is meant that the guide RNA binds preferentially to a target sequence of interest or binds with greater affinity to the target sequence than to other genomic sequences. For example, a gRNA will bind to a substantially complementary sequence and not to unrelated sequences. A gRNA that "selectively binds" to a particular allele, such as a particular mutant allele (e.g., allele comprising a substitution, insertion, or deletion), denotes a gRNA that binds preferentially to the particular target allele, but to a lesser extent to a wild-type allele or other sequences. A gRNA that selectively binds to a particular target DNA sequence will selectively direct binding of an RNA-guided nuclease (e.g., Cas9) to a substantially complementary sequence at the target site and not to unrelated sequences.

As used herein, the term "recombination target site" denotes a region of a nucleic acid molecule comprising a binding site or sequence-specific motif recognized by a site-specific recombinase that binds at the target site and catalyzes recombination of specific sequences of DNA at the target site. Site-specific recombinases catalyze recombination between two such target sites. The relative orientation of the target sites determines the outcome of recombination. For example, translocation occurs if the recombination target sites are on separate DNA molecules.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, semiconductor nanoparticles, dyes, metal ions, metal sols, ligands (e.g., biotin, streptavidin or haptens) and the like. The term "fluorescer" refers to a substance or a portion thereof which is capable of exhibiting fluorescence in the detectable range. Particular examples of labels which may be used in the practice of the present disclosure include, but are not limited to, SYBR green, SYBR gold, a CAL Fluor dye such as CAL Fluor Gold 540, CAL Fluor Orange 560, CAL Fluor Red 590, CAL Fluor Red 610, and CAL Fluor Red 635, a Quasar dye such as Quasar 570, Quasar 670, and Quasar 705, an Alexa Fluor such as Alexa Fluor 350, Alexa Fluor 488, Alexa Fluor 546, Alexa Fluor 555, Alexa Fluor 594, Alexa Fluor 647,and Alexa Fluor 784, a cyanine dye such as Cy 3, Cy3.5, Cy5, Cy5.5, and Cy7, fluorescein, 2',4',5',7'-tetrachloro-4-7-dichlorofluorescein (TET), carboxyfluorescein (FAM), 6-carboxy-4',5'-dichloro-2',7'-dimethoxyfluorescein (JOE), hexachlorofluorescein (HEX), rhodamine, carboxy-X-rhodamine (ROX), tetramethyl rhodamine (TAMRA), FITC, dansyl, umbelliferone, dimethyl acridinium ester (DMAE), Texas red, luminol, NADPH, horseradish peroxidase (HRP), and α-β-galactosidase.

"Homology" refers to the percent identity between two polynucleotide or two polypeptide moieties. Two nucleic acid, or two polypeptide sequences are "substantially homologous" to each other when the sequences exhibit at least about 50% sequence identity, preferably at least about 75% sequence identity, more preferably at least about 80% 85% sequence identity, more preferably at least about 90% sequence identity, and most preferably at least about 95% 98% sequence identity over a defined length of the molecules. As used herein, substantially homologous also refers to sequences showing complete identity to the specified sequence.

In general, "identity" refers to an exact nucleotide to nucleotide or amino acid to amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353 358, National biomedical Research Foundation, Washington, DC, which adapts the local homology algorithm of Smith and Waterman Advances in Appl. Math. 2:482 489, 1981 for peptide analysis. Programs for determining nucleotide sequence identity are available in the Wisconsin Sequence Analysis Package, Version 8 (available from Genetics Computer Group, Madison, WI) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, CA). From this suite of packages, the Smith Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single stranded specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Recombinant host cells", "host cells", "cells", "cell lines," "cell cultures," and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence can be determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. Within certain embodiments of the present disclosure, the expression cassette described herein may be contained within a plasmid or viral vector construct (e.g., a vector for genome modification comprising a genome editing cassette comprising a promoter operably linked to a polynucleotide encoding a guide RNA and a donor polynucleotide). In addition to the components of the expression cassette, the construct may also include, one or more selectable markers, a signal which allows the construct to exist as single stranded DNA (e.g., a M13 origin of replication), at least one multiple cloning site, and a "mammalian" origin of replication (e.g., a SV40 or adenovirus origin of replication).

"Purified polynucleotide" refers to a polynucleotide of interest or fragment thereof which is essentially free, e.g., contains less than about 50%, preferably less than about 70%, and more preferably less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52:456, Sambrook et al. (2001) Molecular Cloning, a laboratory manual, 3rd edition, Cold Spring Harbor Laboratories, New York, Davis et al. (1995) Basic Methods in Molecular Biology, 2nd edition, McGraw-Hill, and Chu et al. (1981) Gene 13:197. Such techniques can be used to introduce one or more exogenous DNA moieties into suitable host cells. The term refers to both stable and transient uptake of the genetic material, and includes uptake of peptide- or antibody-linked DNAs.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as plasmid and viral vectors.

The terms "variant," "analog" and "mutein" refer to biologically active derivatives of the reference molecule that retain desired activity, such as site-directed Cas9 endonuclease activity. In general, the terms "variant" and "analog" refer to compounds having a native polypeptide sequence and structure with one or more amino acid additions, substitutions (generally conservative in nature) and/or deletions, relative to the native molecule, so long as the modifications do not destroy biological activity and which are "substantially homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein. The term "mutein" further includes polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301; Nguyen et al., Chem. Biol. (2000) 7:463-473; and Simon et al., Proc. Natl. Acad. Sci. USA (1992) 89:9367-9371 for descriptions of peptoids). Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, and tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, adenoviruses, retroviruses, alphaviruses, pox viruses, and vaccinia viruses.

The term "derived from" is used herein to identify the original source of a molecule but is not meant to limit the method by which the molecule is made which can be, for example, by chemical synthesis or recombinant means.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

The term "subject" includes both vertebrates and invertebrates, including, without limitation, mammals, including human and non-human mammals such as non-human primates, including chimpanzees and other apes and monkey species; laboratory animals such as mice, rats, rabbits, hamsters, guinea pigs, and chinchillas; domestic animals such as dogs and cats; farm animals such as sheep, goats, pigs, horses and cows; and birds such as domestic, wild and game birds, including chickens, turkeys and other gallinaceous birds, ducks, geese, and the like. In some cases, the methods of the present disclosure find use in experimental animals, in veterinary application, and in the development of animal models for disease, including, but not limited to, rodents including mice, rats, and hamsters; primates, and transgenic animals.

II. MODES OF CARRYING OUT THE INVENTION

Before describing the present disclosure in detail, it is to be understood that this disclosure is not limited to particular formulations or process parameters as such may, of course, vary. It is also to be understood that the terminology used herein is for the purpose of describing particular embodiments of the disclosure only, and is not intended to be limiting.

Although a number of methods and materials similar or equivalent to those described herein can be used in the practice of the present disclosure, the preferred materials and methods are described herein.

The present disclosure is based on the development of methods for massively parallel production of genetically engineered clones using RNA-guided nucleases and genomic barcoding. In particular, high-throughput multiplex genome editing is achieved utilizing a system that facilitates precise genome editing at desired target chromosomal loci by homology directed repair. Integration of guide RNA and donor DNA sequences as a genomic barcode at a separate chromosomal locus allows identification, isolation, and massively-parallel validation of individual variants from a pool of transformants. Strains can be arrayed according to their precise genetic modifications, as specified by donor DNA incorporation in heterologous or native genes. The inventors have demonstrated that their system provides high editing efficiency in yeast cells and enables simultaneous editing at more than one genomic location (Example 1). The inventors have further developed a method of editing codons outside of canonical guide RNA recognition regions, which enables complete saturation mutagenesis of protein-coding genes, and a marker-based internal cloning method, which removes background due to oligonucleotide synthesis errors and incomplete vector backbone cleavage. In addition, homology directed repair (HDR) in metazoan cells may be enhanced by using CRISPR-interference (CRISPRi), RNA interference (RNAi), or chemical-based inhibition of non-homologous end joining (NHEJ) in combination with active donor recruitment. Genome-modified strain collections produced by the methods described herein may be arrayed according to their precise genetic modifications, as specified by barcoded donor DNA incorporation in heterologous or native genes.

In order to further an understanding of the present disclosure, a more detailed discussion is provided below regarding multiplex genome editing with barcoding and strain validation using these methods.

A. Multiplex Genome Editing

As explained above, the methods of the present disclosure provide multiplex genome editing with barcoding of guide RNA-donor DNA expression cassettes used in genome modification of cells to facilitate validation of individual variants from a pool of transformants. Multiplex editing is accomplished by transfecting cells with a plurality of recombinant polynucleotides, each comprising a genome editing cassette comprising a polynucleotide encoding a guide RNA capable of hybridizing at a genomic target locus to be modified and a donor polynucleotide comprising an intended edit sequence to be integrated into the genomic target locus by homology directed repair (HDR). Each genome editing cassette comprises a different guide RNA-donor polynucleotide combination, such that the plurality of recombinant polynucleotides containing them is capable of producing a plurality of different intended edits at one or more genomic target loci. After transfecting the cells with the recombinant polynucleotides, the cells are cultured under conditions suitable for transcription of the guide RNAs from each genome editing cassette. An RNA-guided nuclease is introduced into the cells that is capable of forming complexes with the transcribed guide RNAs, wherein the guide RNAs direct the complexes to one or more genomic target loci in the cells, where the RNA-guided nuclease creates double-stranded breaks in the genomic DNA resulting in integration of the donor polynucleotides at the genomic target loci by HDR to produce a plurality of genetically modified cells. In certain embodiments, the method further comprises performing additional rounds of genome editing on the genetically modified cells by repeating the steps using different genome editing cassettes. The genetically modified cells can be plated in an ordered array on media suitable for their growth to produce arrayed colonies of clones.

A set of genome editing cassettes can be designed to produce mutations at multiple sites within a single gene or at multiple sites in different genes, or anywhere in the genome, including non-coding regions. Such mutations may include insertions, deletions, or substitutions. Each donor polynucleotide contains a sequence comprising a different intended edit to the genome, which can be used to modify a particular target locus in a cell, wherein the donor polynucleotide is integrated into the genome at the target locus by site-directed homologous recombination. A donor polynucleotide can be used, for example, to introduce an intended edit into the genome for the purpose of repairing, modifying, replacing, deleting, attenuating, or inactivating a target gene.

In a donor polynucleotide, the sequence comprising the intended edit is flanked by a pair of homology arms responsible for targeting the donor polynucleotide to the target locus to be edited in a cell. The donor polynucleotide typically comprises a 5' homology arm that hybridizes to a 5' genomic target sequence and a 3' homology arm that hybridizes to a 3' genomic target sequence. The homology arms are referred to herein as 5' and 3' (i.e., upstream and downstream) homology arms, which relates to the relative position of the homology arms to the nucleotide sequence comprising the intended edit within the donor polynucleotide. The 5' and 3' homology arms hybridize to regions within the target locus in the genomic DNA to be modified, which are referred to herein as the "5' target sequence" and "3' target sequence," respectively.

The homology arm must be sufficiently complementary for hybridization to the target sequence to mediate homologous recombination between the donor polynucleotide and genomic DNA at the target locus. For example, a homology arm may comprise a nucleotide sequence having at least about 80-100% sequence identity to the corresponding genomic target sequence, including any percent identity within this range, such as at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity thereto, wherein the nucleotide sequence comprising the intended edit is integrated into the genomic DNA by HDR at the genomic target locus recognized (i.e., sufficiently complementary for hybridization) by the 5' and 3' homology arms.

In certain embodiments, the corresponding homologous nucleotide sequences in the genomic target sequence (i.e., the "5' target sequence" and "3' target sequence") flank a specific site for cleavage and/or a specific site for introducing the intended edit. The distance between the specific cleavage site and the homologous nucleotide sequences (e.g., each homology arm) can be several hundred nucleotides. In some embodiments, the distance between a homology arm and the cleavage site is 200 nucleotides or less (e.g., 0, 10, 20, 30, 50, 75, 100, 125, 150, 175, and 200 nucleotides). In most cases, a smaller distance may give rise to a higher gene targeting rate. In a preferred embodiment, the donor polynucleotide is substantially identical to the target genomic sequence, across its entire length except for the sequence changes to be introduced to a portion of the genome that encompasses both the specific cleavage site and the portions of the genomic target sequence to be altered.

A homology arm can be of any length, e.g. 10 nucleotides or more, 50 nucleotides or more, 100 nucleotides or more, 250 nucleotides or more, 300 nucleotides or more, 350 nucleotides or more, 400 nucleotides or more, 450 nucleotides or more, 500 nucleotides or more, 1000 nucleotides (1 kb) or more, 5000 nucleotides (5 kb) or more, 10000 nucleotides (10 kb) or more, etc. In some instances, the 5' and 3' homology arms are substantially equal in length to one another, e.g. one may be 30% shorter or less than the other homology arm, 20% shorter or less than the other homology arm, 10% shorter or less than the other homology arm, 5% shorter or less than the other homology arm, 2% shorter or less than the other homology arm, or only a few nucleotides less than the other homology arm. In other instances, the 5' and 3' homology arms are substantially different in length from one another, e.g. one may be 40% shorter or more, 50% shorter or more, sometimes 60% shorter or more, 70% shorter or more, 80% shorter or more, 90% shorter or more, or 95% shorter or more than the other homology arm.

In certain embodiments, cells containing modified genomes are identified in vitro or in vivo by including a selection marker expression cassette in the vectors. Selection markers confer an identifiable change to a cell permitting positive selection of genetically modified cells having the donor polynucleotide integrated into the genome. For example, nutritional markers (i.e., genes that confer the ability to grow in a nutrient deficient medium), such as cytosine deaminase (Fcy1), which in *Saccharomyces cerevisiae* confers the ability to grow on media containing cytosine as the sole nitrogen source (5-fluorocytosine is toxic to cytosine deaminase-producing cells and can be used for counter-selection), imidazoleglycerol-phosphate dehydratase (HIS3), which in *Saccharomyces cerevisiae* confers the ability to grow on medium lacking histidine, phosphoribosyl-anthranilate isomerase (TRP1), which in *Saccharomyces cerevisiae* confers the ability to grow on medium lacking tryptophan (5-fluoroanthranilic acid is toxic to phosphoribosyl-anthranilate isomerase-producing cells and can be used for counter-selection), and orotidine 5'-phosphate decarboxylase (URA3) which in *Saccharomyces cerevisiae* confers the ability to grow on media lacking uracil or uridine (5-fluoroorotic acid is toxic to orotidine 5'-phosphate decarboxylase-producing cells and can be used for counter-selection); fluorescent or bioluminescent markers (e.g., mCherry, Dronpa, mOrange, mPlum, Venus, YPet, green fluorescent protein (GFP), enhanced green fluorescent protein (EGFP), phycoerythrin, or luciferase); cell surface markers; expression of a reporter gene (e.g., GFP, dsRed, GUS, lacZ, CAT); or drug selection markers such as genes that confer resistance to neomycin, puromycin, hygromycin, DHFR, GPT, zeocin, or histidinol may be used to identify cells. Alternatively, enzymes such as herpes simplex virus thymidine kinase (tk) or chloramphenicol acetyltransferase (CAT) may be employed. Any selectable marker may be used as long as it is capable of being expressed after integration of the donor polynucleotide by HDR to allow identification of genetically modified cells. Further examples of selectable markers are well known to one of skill in the art.

In certain embodiments, the selection marker expression cassette encodes two or more selection markers. Selection markers may be used in combination, for example, a nutritional marker or cell surface marker may be used with a fluorescent marker, or a drug resistance gene may be used with a suicide gene. In certain embodiments, the donor polynucleotide is provided by a multicistronic vector to allow expression of multiple selection markers in combination. The multicistronic vector may include an IRES or viral 2A peptide to allow expression of more than one selection marker from a single vector as described further below.

In diploid cells, genome editing, as described herein, may result in either one allele or two alleles being modified in the genomic DNA. In certain embodiments, at least one of the selection markers used for positive selection is a fluorescent marker, wherein florescence intensity can be measured to determine if the genetically modified cell comprises a monoallelic edit or a bi-allelic edit.

In other embodiments, a negative selection marker is used to identify cells not having a selection marker expression cassette (i.e. having sequences encoding positive selection markers disrupted or deleted). For example, integration of a genome editing cassette into a vector may be detected by the disruption of a selection marker gene. A suicide marker may be included as a negative selection marker to facilitate negative selection of cells. Suicide genes can be used to selectively kill cells by inducing apoptosis or converting a nontoxic drug to a toxic compound in genetically modified cells. Examples include suicide genes encoding thymidine kinases, cytosine deaminases, intracellular antibodies, telomeraseses, caspases, and DNases. In certain embodiments, a suicide gene is used in combination with one or more other selection markers, such as those described above for use in positive selection of cells. In addition, a suicide gene may be used in genetically modified cells, for example, to improve their safety by allowing their destruction at will. See, e.g., Jones et al. (2014) Front. Pharmacol. 5:254, Mitsui et al. (2017) Mol. Ther. Methods Clin. Dev. 5:51-58, Greco et al. (2015) Front. Pharmacol. 6:95; herein incorporated by reference.

Genome editing may be performed on a single cell or a population of cells of interest and can be performed on any type of cell, including any cell from a prokaryotic, eukaryotic, or archaeon organism, including bacteria, archaea, fungi, protists, plants, and animals. Cells from tissues, organs, and biopsies, as well as recombinant cells, genetically modified cells, cells from cell lines cultured in vitro, and artificial cells (e.g., nanoparticles, liposomes, polymersomes, or microcapsules encapsulating nucleic acids) may all be used in the practice of the present disclosure. The methods of the disclosure are also applicable to editing of nucleic acids in cellular fragments, cell components, or organelles comprising nucleic acids (e.g., mitochondria in animal and plant cells, plastids (e.g., chloroplasts) in plant cells and algae). Cells may be cultured or expanded prior to or after performing genome editing as described herein. In one embodiment, the cells are yeast cells.

An RNA-guided nuclease can be targeted to a particular genomic sequence (i.e., genomic target sequence to be modified) by altering its guide RNA sequence. A target-specific guide RNA comprises a nucleotide sequence that is complementary to a genomic target sequence, and thereby mediates binding of the nuclease-gRNA complex by hybridization at the target site. For example, the gRNA can be designed with a sequence complementary to the sequence of a minor allele to target the nuclease-gRNA complex to the site of a mutation. The mutation may comprise an insertion, a deletion, or a substitution. For example, the mutation may include a single nucleotide variation, gene fusion, translocation, inversion, duplication, frameshift, missense, nonsense, or other mutation associated with a phenotype or disease of interest. The targeted minor allele may be a common genetic variant or a rare genetic variant. In certain embodiments, the gRNA is designed to selectively bind to a minor allele with single base-pair discrimination, for example, to allow binding of the nuclease-gRNA complex to a single nucleotide polymorphism (SNP). In particular, the gRNA may be designed to target disease-relevant mutations of interest for the purpose of genome editing to remove the mutation from a gene. Alternatively, the gRNA can be designed with a sequence complementary to the sequence of a major or wild-type allele to target the nuclease-gRNA complex to the allele for the purpose of genome editing to introduces a mutation into a gene in the genomic DNA of the cell, such as an insertion, deletion, or substitution. Such genetically modified cells can be used, for example, to alter phenotype, confer new properties, or produce disease models for drug screening.

In certain embodiments, the RNA-guided nuclease used for genome modification is a clustered regularly interspersed short palindromic repeats (CRISPR) system Cas nuclease. Any RNA-guided Cas nuclease capable of catalyzing site-directed cleavage of DNA to allow integration of donor polynucleotides by the HDR mechanism can be used in genome editing, including CRISPR system type I, type II, or type III Cas nucleases. Examples of Cas proteins include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cul966, and homologs or modified versions thereof.

In certain embodiments, a type II CRISPR system Cas9 endonuclease is used. Cas9 nucleases from any species, or biologically active fragments, variants, analogs, or derivatives thereof that retain Cas9 endonuclease activity (i.e., catalyze site-directed cleavage of DNA to generate double-strand breaks) may be used to perform genome modification as described herein. The Cas9 need not be physically derived from an organism, but may be synthetically or recombinantly produced. Cas9 sequences from a number of bacterial species are well known in the art and listed in the National Center for Biotechnology Information (NCBI) database. See, for example, NCBI entries for Cas9 from: *Streptococcus pyogenes* (WP_002989955, WP_038434062, WP_011528583); *Campylobacter jejuni* (WP_022552435, YP_002344900), *Campylobacter coli* (WP_060786116); *Campylobacter fetus* (WP_059434633); *Corynebacterium ulcerans* (NC_015683, NC_017317); *Corynebacterium diphtheria* (NC_016782, NC_016786); *Enterococcus faecalis* (WP_033919308); *Spiroplasma syrphidicola* (NC_021284); *Prevotella intermedia* (NC_017861); *Spiroplasma taiwanense* (NC_021846); *Streptococcus iniae* (NC_021314); *Belliella baltica* (NC_018010); *Psychroflexus torquisI* (NC_018721); *Streptococcus thermophilus* (YP_820832), *Streptococcus mutans* (WP_061046374, WP_024786433); *Listeria innocua* (NP_472073); *Listeria monocytogenes* (WP_061665472); *Legionella pneumophila* (WP_062726656); *Staphylococcus aureus* (WP_001573634); *Francisella tularensis* (WP_032729892, WP_014548420), *Enterococcus faecalis* (WP_033919308); *Lactobacillus rhamnosus* (WP_048482595, WP_032965177); and *Neisseria meningitidis* (WP_061704949, YP_002342100); all of which sequences (as entered by the date of filing of this application) are herein incorporated by reference. Any of these sequences or a variant thereof comprising a sequence having at least about 70-100% sequence identity thereto, including any percent identity within this range, such as 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity thereto, can be used for genome editing, as described herein. See also Fonfara et al. (2014) Nucleic Acids Res. 42(4):2577-90; Kapitonov et al. (2015) J. Bacteriol. 198(5):797-807, Shmakov et al. (2015) Mol. Cell. 60(3):385-397, and Chylinski et al. (2014) Nucleic Acids Res. 42(10):6091-6105); for sequence comparisons and a discussion of genetic diversity and phylogenetic analysis of Cas9.

The CRISPR-Cas system naturally occurs in bacteria and archaea where it plays a role in RNA-mediated adaptive immunity against foreign DNA. The bacterial type II CRISPR system uses the endonuclease, Cas9, which forms a complex with a guide RNA (gRNA) that specifically hybridizes to a complementary genomic target sequence, where the Cas9 endonuclease catalyzes cleavage to produce a double-stranded break. Targeting of Cas9 typically further relies on the presence of a 5' protospacer-adjacent motif (PAM) in the DNA at or near the gRNA-binding site.

The genomic target site will typically comprise a nucleotide sequence that is complementary to the gRNA, and may further comprise a protospacer adjacent motif (PAM). In certain embodiments, the target site comprises 20-30 base pairs in addition to a 3 base pair PAM. Typically, the first nucleotide of a PAM can be any nucleotide, while the two other nucleotides will depend on the specific Cas9 protein that is chosen. Exemplary PAM sequences are known to those of skill in the art and include, without limitation, NNG, NGN, NAG, and NGG, wherein N represents any nucleotide. In certain embodiments, the allele targeted by a gRNA comprises a mutation that creates a PAM within the allele, wherein the PAM promotes binding of the Cas9-gRNA complex to the allele.

In certain embodiments, the gRNA is 5-50 nucleotides, 10-30 nucleotides, 15-25 nucleotides, 18-22 nucleotides, or 19-21 nucleotides in length, or any length between the stated ranges, including, for example, 10, 11, 12, 13, 14, 15, 16, 17, 18, 19, 20, 21, 22, 23, 24, 25, 26, 27, 28, 29, 30, 31, 32, 33, 34, or 35 nucleotides in length. The guide RNA may be a single guide RNA comprising crRNA and tracrRNA sequences in a single RNA molecule, or the guide RNA may comprise two RNA molecules with crRNA and tracrRNA sequences residing in separate RNA molecules.

In another embodiment, the CRISPR nuclease from *Prevotella* and *Francisella* 1 (Cpf1) may be used. Cpf1 is another class II CRISPR/Cas system RNA-guided nuclease with similarities to Cas9 and may be used analogously. Unlike Cas9, Cpf1 does not require a tracrRNA and only depends on a crRNA in its guide RNA, which provides the advantage that shorter guide RNAs can be used with Cpf1 for targeting than Cas9. Cpf1 is capable of cleaving either DNA or RNA. The PAM sites recognized by Cpf1 have the sequences 5'-YTN-3' (where "Y" is a pyrimidine and "N" is any nucleobase) or 5'-TTN-3', in contrast to the G-rich PAM site recognized by Cas9. Cpf1 cleavage of DNA produces double-stranded breaks with a sticky-ends having a 4 or 5 nucleotide overhang. For a discussion of Cpf1, see, e.g., Ledford et al. (2015) Nature. 526 (7571):17-17, Zetsche et al. (2015) Cell. 163 (3):759-771, Murovec et al. (2017) Plant Biotechnol. J. 15(8):917-926, Zhang et al. (2017) Front. Plant Sci. 8:177, Fernandes et al. (2016) Postepy Biochem. 62(3):315-326; herein incorporated by reference.

C2c1 is another class II CRISPR/Cas system RNA-guided nuclease that may be used. C2c1, similarly to Cas9, depends on both a crRNA and tracrRNA for guidance to target sites. For a description of C2c1, see, e.g., Shmakov et al. (2015) Mol Cell. 60(3):385-397, Zhang et al. (2017) Front Plant Sci. 8:177; herein incorporated by reference.

In yet another embodiment, an engineered RNA-guided FokI nuclease may be used. RNA-guided FokI nucleases comprise fusions of inactive Cas9 (dCas9) and the FokI endonuclease (FokI-dCas9), wherein the dCas9 portion confers guide RNA-dependent targeting on FokI. For a description of engineered RNA-guided FokI nucleases, see, e.g., Havlicek et al. (2017) Mol. Ther. 25(2):342-355, Pan et al. (2016) Sci Rep. 6:35794, Tsai et al. (2014) Nat Biotechnol. 32(6):569-576; herein incorporated by reference.

The RNA-guided nuclease can be provided in the form of a protein, such as the nuclease complexed with a gRNA, or provided by a nucleic acid encoding the RNA-guided nuclease, such as an RNA (e.g., messenger RNA) or DNA (expression vector). Codon usage may be optimized to improve production of an RNA-guided nuclease in a particular cell or organism. For example, a nucleic acid encoding an RNA-guided nuclease can be modified to substitute codons having a higher frequency of usage in a yeast cell, a bacterial cell, a human cell, a non-human cell, a mammalian cell, a rodent cell, a mouse cell, a rat cell, or any other host cell of interest, as compared to the naturally occurring polynucleotide sequence. When a nucleic acid encoding the RNA-guided nuclease is introduced into cells, the protein can be transiently, conditionally, or constitutively expressed in the cell.

Donor polynucleotides and gRNAs are readily synthesized by standard techniques, e.g., solid phase synthesis via phosphoramidite chemistry, as disclosed in U.S. Pat. Nos. 4,458,066 and 4,415,732, incorporated herein by reference; Beaucage et al., *Tetrahedron* (1992) 48:2223-2311; and Applied Biosystems User Bulletin No. 13 (1 Apr. 1987). Other chemical synthesis methods include, for example, the phosphotriester method described by Narang et al., *Meth. Enzymol.* (1979) 68:90 and the phosphodiester method disclosed by Brown et al., *Meth. Enzymol.* (1979) 68:109. In view of the short lengths of gRNAs (typically about 20 nucleotides in length) and donor polynucleotides (typically about 100-150 nucleotides), gRNA-donor polynucleotide cassettes can be produced by standard oligonucleotide synthesis techniques and subsequently ligated into vectors. Moreover, libraries of gRNA-donor polynucleotide cassettes directed against thousands of genomic targets can be readily created using highly parallel array-based oligonucleotide library synthesis methods (see, e.g., Cleary et al. (2004) Nature Methods 1:241-248, Svensen et al. (2011) PLoS One 6(9):e24906).

In addition, adapter sequences can be added to oligonucleotides to facilitate high-throughput amplification or sequencing. For example, a pair of adapter sequences can be added at the 5' and 3' ends of an oligonucleotide to allow amplification or sequencing of multiple oligonucleotides simultaneously by the same set of primers. Additionally, restriction sites can be incorporated into oligonucleotides to facilitate cloning of oligonucleotides into vectors. For example, oligonucleotides comprising gRNA-donor polynucleotide cassettes can be designed with a common 5' restriction site and a common 3' restriction site to facilitate ligation into the genome modification vectors. A restriction digest that selectively cleaves each oligonucleotide at the common 5' restriction site and the common 3' restriction site is performed to produce restriction fragments that can be cloned into vectors (e.g., plasmids or viral vectors), followed by transformation of cells with the vectors comprising the gRNA-donor polynucleotide cassettes.

Amplification of polynucleotides encoding gRNA-donor polynucleotide cassettes may be performed, for example, before ligation into genome modification vectors or before sequencing after barcoding. Any method for amplifying oligonucleotides may be used, including, but not limited to polymerase chain reaction (PCR), isothermal amplification, nucleic acid sequence-based amplification (NASBA), transcription mediated amplification (TMA), strand displacement amplification (SDA), and ligase chain reaction (LCR). In one embodiment, the genome editing cassettes comprise common 5' and 3' priming sites to allow amplification of the gRNA-donor polynucleotide sequences in parallel with a set of universal primers. In another embodiment, a set of selective primers is used to selectively amplify a subset of the gRNA-donor polynucleotides from a pooled mixture.

Cells that are transformed with recombinant polynucleotides comprising the genome editing cassettes may be prokaryotic cells or eukaryotic cells, and are preferably designed for high-efficiency incorporation of gRNA-donor polynucleotide libraries by transformation. Methods of introducing nucleic acids into a host cell are well known in the art. Commonly used methods of transformation include chemically induced transformation, typically using divalent cations (e.g., $CaCl_2$), and electroporation. See, e.g., Sambrook et al. (2001) Molecular Cloning, a laboratory manual, $3^{rd}$ edition, Cold Spring Harbor Laboratories, New York, Davis et al. (1995) Basic Methods in Molecular Biology, $2^{nd}$ edition, McGraw-Hill, and Chu et al. (1981) Gene 13:197; herein incorporated by reference in their entireties.

Normally random diffusion of donor DNA to a DNA break is rate-limiting for homologous repair. Active donor recruitment may be used to increase the frequency of cells genetically modified by HDR. The method for active donor recruitment comprises: a) introducing into a cell a fusion protein comprising a protein that selectively binds to the DNA break connected to a polypeptide comprising a nucleic acid binding domain; and b) introducing into the cell a donor polynucleotide comprising i) a nucleotide sequence sufficiently complementary to hybridize to a sequence adjacent to the DNA break, and ii) a nucleotide sequence comprising a binding site recognized by the nucleic acid binding domain of the fusion protein, wherein the nucleic acid binding domain selectively binds to the binding site on the donor polynucleotide to produce a complex between the donor polynucleotide and the fusion protein, thereby recruiting the donor polynucleotide to the DNA break and promoting HDR.

The DNA break may be created by a site-specific nuclease, such as, but not limited to, a Cas nuclease (e.g., Cas9, Cpf1, or C2c1), an engineered RNA-guided FokI nuclease, a zinc finger nuclease (ZFN), a transcription activator-like effector-based nuclease (TALEN), a restriction endonuclease, a meganuclease, a homing endonuclease, and the like. Any site-specific nuclease that selectively cleaves a sequence at the target integration site for the donor polynucleotide may be used.

The DNA break may be a single-stranded (nick) or double-stranded DNA break. If the DNA break is a single-stranded DNA break, the fusion protein used comprises a protein that selectively binds to the single-stranded DNA break, whereas if the DNA break is a double-stranded DNA break, the fusion protein used comprises a protein that selectively binds to the double-stranded DNA break.

In the fusion, the protein that selectively binds to the DNA break can be, for example, an RNA-guided nuclease, such as a Cas nuclease (e.g., Cas9 or Cpf1) or an engineered RNA-guided FokI nuclease.

Donor polynucleotides may be single-stranded or double-stranded, and may be composed of RNA or DNA. A donor polynucleotide comprising DNA can be produced from a donor polynucleotide comprising RNA, if desired, by reverse transcription using reverse transcriptase. Depending on the type of nucleic acid binding domain in the fusion protein, the donor polynucleotide may comprise, for example, a corresponding binding site comprising an RNA sequence recognized by an RNA binding domain or a DNA sequence recognized by a DNA binding domain. For example, the fusion protein can be constructed with a LexA DNA binding domain to be matched with a corresponding LexA binding site in the donor polynucleotide. In another example, the fusion protein can be constructed with a FKH1 DNA binding domain to be matched with a corresponding FKH1 binding site in the donor polynucleotide.

The DNA binding domain may be any protein or domain from a protein that binds a known DNA sequence. Nonlimiting examples include LexA, Gal4, Zinc Finger protein, TALE, or a transcription factor. Additionally, a streptavidin-biotin complex may be used, such that the DNA binding domain is streptavidin or a portion thereof that binds biotin, and the donor DNA has biotin conjugated thereto. Examples of each of these proteins, including their sequences, are well known in the art.

In another embodiment, the fusion protein may further comprise a FHA phosphothreonine-binding domain, wherein the donor polynucleotide is selectively recruited to a DNA break having a protein comprising a phosphorylated threonine residue located sufficiently close to the DNA break for the FHA phosphothreonine-binding domain to bind to the phosphorylated threonine residue. The FHA phosphothreonine-binding domain may be combined with any DNA binding domain (e.g., fusion with FHK1-LexA) for donor recruitment.

Without being bound by theory, it is contemplated that the donor recruitment protein may comprise a polypeptide domain from any protein that is recruited to a DNA break, e.g., a double-stranded DNA break. Non-limiting examples include proteins that bind to areas of DNA damage and/or DNA repair proteins. Phospho-Ser/Thr-binding domains have emerged as crucial regulators of cell cycle progression and DNA damage signaling. Such domains include 14-3-3 proteins, WW domains, Polo-box domains (in PLK1), WD40 repeats (including those in the E3 ligase $SCF^{\beta TrCP}$), BRCT domains (including those in BRCA1) and FHA domains (such as in CHK2 and MDC1). These domains all have the potential to be used in donor recruitment systems. FHA domains are conserved as far back as bacteria and thus would also have utility in bacteria as well as eukaryotes for donor recruitment. Examples of proteins or genes encoding such proteins are provided, without limitation, in Tables 1-5. Additional genes/proteins are known in the art and can be found, for example, by searching public gene or protein databases for genes or proteins known to have a role in DNA repair or binding of DNA damage (e.g., gene ontology term analysis). It is contemplated that proteins from any species can be used (e.g., eukaryotic proteins, proteins from yeast, mammalian cells, including human proteins, and/or from fungus). In embodiments, the donor recruitment protein comprises a polypeptide sequence from a DNA break-recruiting protein from the same kingdom, phylum or division, class, order, family, genus, and/or species as the cell to be genetically modified.

TABLE 1

Human Proteins for Recruitment to DNA Break

| KU70 | RAD9 | PARP1 | BLM | PolV |
|---|---|---|---|---|
| KU80 | HUS1 | PARP2 | WRN | RECQL5 |
| DNA PK | RAD1 | ATRIP | EXO1 | FANCJ |
| DNA LIG IV | RAD18 | RAD50 | 53BP1 | FANCM |
| RPA | TOPBP1 | NBS1 | BRCA1 | RNF8 |
| RAD51 | ATM | MRE11 | RIF1 | RINN1 |
| RAD52 | ATR | CtIP | PTIP | RINN2 |
| BRCA2 | H2AX | DNA2 | PARI | RINN3 |

TABLE 2

Mammalian FOX Genes

Foxa1
Foxa2
Foxa3
Foxb1
Foxb2
Foxc1
Foxc2
Foxd1
Foxd2
Foxd3
Foxd4
Foxe1
Foxe3
Foxf1
Foxf2

TABLE 2-continued

| Mammalian FOX Genes |
|---|
| Foxg1 |
| Foxg2 |
| Foxg1 |
| Foxh1 |
| Foxi1 |
| Foxi2 |
| Foxi3 |
| Foxj1 |
| Foxj2 |
| Foxj3 |
| Foxk1 |
| Foxk2 |
| Foxl1 |
| Foxl2 |
| Foxm1 |
| Foxn1 |
| Foxn2 |
| Foxn3 |
| Foxn4 |
| Foxo1 |
| Foxo3 |
| Foxo4 |
| Foxo6 |
| Foxp1 |
| Foxp2 |
| Foxp3 |
| Foxp4 |
| Foxq1 |
| Foxr1 |
| Foxr2 |
| Foxs1 |

TABLE 3

Human DNA Damage-Binding Genes

| | | | | | | | |
|---|---|---|---|---|---|---|---|
| MUTYH | MSH3 | ERCC4 | PCNA | XRCC6 | REV1 | HMGB2 | RAD1 |
| APEX1 | saga human | ERCC2 | DDB1 | BRCA1 | NBN | DCLRE1B | ERCC3 |
| RPA1 | ddb1-ddb2_human | XRCC5 | BLM | TDG | POLK | POLB | FANCG |
| POT1 | tftc_human | WRN | NEIL1 | XRCC1 | GTF2H3 | RBBP8 | RPA4 |
| CREBBP | msh2-msh6_human | EP300 | POLQ | DCLRE1A | XPA | H2AFX | AUNIP |
| OGG1 | RPS3 | RAD18 | MSH6 | RPA3 | APTX | CUL4B | ERCC1 |
| Q6ZNB5 | UNG | MSH5 | RPA2 | DDB2 | TP53BP1 | RAD23A | RAD23B |
| FEN1 | POLD1 | M0R2N6 | MPG | CRY2 | HMGB1 | POLI | PNKP |
| NEIL3 | MSH2 | POLH | E9PQ18 | RECQL4 | NEIL2 | MSH4 | DCLRE1C |
| XPC | | | | | | | |

TABLE 4

Human DNA Repair

| | | | | | | | |
|---|---|---|---|---|---|---|---|
| FAN1 | MCMDC2 | RRM2B | UHRF1 | UBE2V2 | FOXM1 | RAD51 | ESCO2 |
| KDM2A | UBE2L6 | REV3L | TERF2IP | CDK1 | TNKS1BP1 | TIGAR | PRKDC |
| ZBTB1 | TP53BP1 | PRKCG | MMS19 | HIST3H2A | FTO | SMARCAD1 | SHLD2 |
| USP10 | FIGNL2 | HMGN1 | PNKP | SIX6OS1 | PIF1 | BIVM-ERCC5 | KIF22 |
| RECQL4 | HMGB1 | USP7 | FANCA | DTX3L | PPIE | RAD21L1 | MSH3 |
| NCOA6 | SLF1 | RAD23A | TP73 | TTC5 | INO80B | FANCF | POLR2J |
| SMC1A | MUS81 | POLR2C | ETAA1 | UVSSA | PRMT6 | MCM8 | POLR2H |
| MDC1 | ZRANB3 | CDK9 | RAD51B | EID3 | EME1 | UBE2U | DMAP1 |
| TRIP12 | POLE2 | POLI | GADD45A | CDC5L | NEIL1 | HMGA2 | ZFYVE26 |
| TONSL | NEIL2 | REC8 | TRIM28 | RAD52 | UVRAG | EME2 | URS0000170CF4_9606 |
| ASCC2 | BACH1 | UBR5 | BABAM2 | PARP9 | CDCA5 | EGFR | SHPRH |
| RNF169 | PSMD14 | TRIM25 | INO80C | PARK7 | DDX11 | ZSWIM7 | ube2n-ube2v2_human |
| REV1 | RNF168 | ATR | PPP4R2 | XRCC5 | PTTG1 | RAD51AP1 | inip-ints3-nabp2_human |
| ASF1A | UFD1 | RECQL5 | DCLRE1C | EMSY | POLG2 | ABL1 | ercc1-xpf_human |
| MORF4L1 | COPS6 | MEIOB | XPC | MGMT | HUS1B | RFC1 | eme1-mus81_human |
| POLR2G | UBE2B | CDKN2D | ERCC8 | SFPQ | MCRS1 | RFC2 | msh2-msh3_human |
| SAMHD1 | USP3 | RPS3 | SMC6 | FANCC | SPATA22 | RFC4 | btr_human |
| MAD2L2 | EYA3 | BRCC3 | A0A1W2PQ90 | ASTE1 | MLH3 | RPA3 | rrm1-rrm2b_human |
| OTUB1 | SHLD1 | POLN | SYCP1 | MUM1 | CDC45 | DDB2 | ku70_80_human |
| TDP2 | HMGB2 | UBC | PPP5C | USP43 | POLQ | MC1R | nua4_human |
| MSH5 | DCLRE1B | HSF1 | POLR2I | USP45 | RAD51C | WDR70 | ddb1-ddb2_human |
| LOC107984078 | FANCM | UNG | KAT5 | USP51 | MSH6 | POLE | pp4_human-2b |
| UBE2W | NSD2 | GTF2H2 | COPS5 | ERCC5 | EPC2 | PAGR1 | eme2-mus81_human |
| RFC3 | ACTL6A | APLF | UPF1 | SWI5 | RBM17 | INO80D | inip-ints3-nabp1_human |

TABLE 4-continued

| Human DNA Repair | | | | | | | |
|---|---|---|---|---|---|---|---|
| RFC5 | CHEK2 | TP53 | MEIOC | VCP | POLH | FANCE | RNASEH2A |
| M0R2N6 | NONO | TOPBP1 | MRNIP | CHRNA4 | POLR2B | MUTYH | POLK |
| NABP1 | hCG_2039718 | PARG | FANCD2 | TIMELESS | RUVBL1 | APEX1 | GINS2 |
| TMEM189-UBE2V1 | FAAP20 | GTF2H5 | TEX12 | WDR33 | COPS7A | RPA1 | RUVBL2 |
| AXIN2 | PALB2 | MAGEF1 | TEX15 | YY1 | ALKBH5 | SPRTN | Q6ZNB5 |
| TENT4A | CHD1L | CLSPN | PAXIP1 | CDK7 | APEX2 | RHNO1 | RNF111 |
| INO80E | CIB1 | DDX1 | POLA1 | WRN | PCNA | RCHY1 | FEN1 |
| DMC1 | ZNF365 | SWSAP1 | PARP1 | GTF2H2C | DDB1 | TDP1 | WDHD1 |
| TAOK3 | TERF2 | GINS4 | ERCC6L2 | SPIDR | XRCC3 | RBM14 | RBX1 |
| NFRKB | RNF138 | ACTR5 | SLX4 | KIN | XRCC2 | NHEJ1 | POLR2L |
| BOD1L1 | POLB | DHX9 | GTF2H4 | EP300 | BLM | COPS7B | NUDT16 |
| RPA2 | PMS2P5 | RMI1 | SMC5 | DEK | UBE2A | AP5S1 | RMI2 |
| SSRP1 | ATP23 | NUDT16L1 | SFR1 | RAD18 | NUCKS1 | USP1 | POLG |
| EYA4 | NPAS2 | GEN1 | HELQ | RPS27A | AUNIP | POLD4 | HIST1H4A |
| HMGA1 | MNAT1 | ACTR8 | TNP1 | COPS8 | HINFP | MEN1 | FBH1 |
| AP5Z1 | CCNH | SEM1 | E9PQ18 | RNF8 | POLR2E | XAB2 | PARP3 |
| GTF2H3 | NSMCE1 | COPS3 | GPS1 | ATRIP | TREX1 | RAD54L | UCHL5 |
| CENPS | RBBP8 | ERCC3 | XRCC6 | SMUG1 | ERCC1 | NUDT1 | SPO11 |
| POLR2K | ORAOV1 | MGME1 | PRPF19 | SUPT16H | EXO1 | APBB1 | PSME4 |
| MARF1 | SLF2 | SMC3 | FANCL | RECQL | CEP164 | NPM1 | FIGN |
| PIAS4 | BRCA2 | PDS5A | FANCI | CHEK1 | FBXO6 | CEBPG | POLD2 |
| TICRR | H2AFX | XRCC4 | EXD2 | COPS4 | SHLD3 | TCEA1 | SIRT1 |
| SETX | DNA2 | NOP53 | RIF1 | BARD1 | ZNF830 | IGHMBP2 | UBA52 |
| FAM168A | POLD3 | UBE2V1 | ALKBH3 | BRCA1 | TREX2 | ASCC3 | HELB |
| PMS2P1 | MORF4L2 | PMS2P3 | CDC14B | TWIST1 | RAD23B | EEPD1 | POLL |
| XPA | PCLAF | DTL | INTS3 | TRIP13 | PML | OGG1 | PARP2 |
| CBX8 | UBB | SMARCAL1 | XRCC1 | SETMAR | NABP2 | FGF10 | PPP4C |
| SUMO1 | EYA2 | POLR2F | RTEL1 | TDG | RFWD3 | POLR2D | TFPT |
| APTX | CETN2 | COPS2 | CYREN | USP47 | EXO5 | RADX | CENPX |
| TAOK1 | SLC3OA9 | MSH4 | DCLRE1A | GTF2H1 | INIP | WRAP53 | RAD54B |
| ASCC1 | WDR48 | FIGNL1 | SIRT6 | ISY1 | HERC2 | POLM | ALKBH2 |
| RTEL1-TNFRSF6B | ERCC6 | MTA1 | HUWE1 | FZR1 | PMS2P2 | ATRX | FANCB |
| PARPBP | RPAIN | ATM | BRIP1 | CSNK1E | HIST3H3 | UBE2N | MBD4 |
| TMEM161A | CDK2 | CINP | CCDC155 | INO80 | PMS2 | NIPBL | MLH1 |
| BABAM1 | LIG1 | PAXX | POLD1 | PDS5B | PMS1 | UBE2D3 | LIG3 |
| JMY | ALKBH1 | FANCG | EYA1 | NSMCE3 | ATXN3 | NBN | ANKLE1 |
| WRNIP1 | POLR2A | UIMC1 | MSH2 | NSMCE2 | PARP4 | HUS1 | |
| SMCHD1 | PMS2P11 | TFIP11 | RAD50 | MRE11 | RAD51D | USP28 | |
| ENDOV | CUL4B | RPA4 | ERCC4 | LIG4 | MPG | NPLOC4 | |
| MCM9 | CUL4A | CHAF1B | ERCC2 | KLHL15 | STUB1 | NEIL3 | |
| NSMCE4A | SETD2 | CHAF1A | CDC7 | KDM1A | RAD21 | GGN | |
| KDM4D | UBE2T | MMS22L | FAAP100 | PRIMPOL | SLX1A | NTHL1 | |
| BCCIP | ISG15 | FAAP24 | ABRAXAS1 | AQR | UBE2NL | BTG2 | |

TABLE 5

| Yeast DNA Repair | | | | | | | |
|---|---|---|---|---|---|---|---|
| SGS1 | RTT101 | SIR3 | MRE11 | DPB2 | IRC7 | MHF1 | LYS20 |
| SMC5 | IRC4 | SEN1 | RAD14 | MMS1 | RSC8 | TFB5 | CDC9 |
| SIN3 | LCD1 | CDC73 | RFC1 | CTF4 | ECO1 | MSH3 | NUP133 |
| DDR48 | CDC45 | EAF6 | ULS1 | RPT4 | SOH1 | DNA2 | MSH5 |
| MLH1 | MLH2 | RFC2 | TEL1 | HNT3 | NUP84 | RAD18 | RPO21 |
| TPP1 | RAD5 | RAD7 | MCM2 | ESA1 | NSE4 | POL4 | MPH1 |
| PSO2 | RAD2 | TAH11 | APN2 | XRS2 | POL3 | RTT107 | RAD51 |
| YKU80 | SLD5 | POL32 | TFB4 | ESC2 | SUB2 | WSS1 | RRD1 |
| RFA2 | TFB3 | BDF1 | NHP6A | EAF1 | BRE1 | MSH1 | MCM10 |
| MCK1 | ADA2 | CST9 | EAF3 | HIM1 | BDF2 | TRA1 | SSL2 |
| RFC3 | ECM11 | SMC6 | MCM4 | RAD34 | DOA1 | YNG2 | REV7 |
| TOF1 | DOT1 | PSY3 | REC8 | TFB1 | RAD59 | MRC1 | TPA1 |
| CTF18 | LRS4 | RSC2 | ELG1 | SPT4 | SIT4 | SEM1 | YEN1 |
| PDS5 | RAD30 | RAD26 | ARP8 | RSC1 | SIR2 | RSC30 | KRE29 |
| POL2 | MUS81 | SFH1 | LEO1 | SWC4 | RPN4 | RRM3 | CSM2 |
| CSM3 | YRA1 | MMS22 | HTA2 | HRQ1 | CDC7 | SLD3 | MET18 |
| SUB1 | RAD10 | HRR25 | RFA1 | NSE3 | SLX5 | PAN2 | STH1 |
| HED1 | POB3 | DDC1 | NUP60 | RTF1 | MCD1 | NUP145 | MHF2 |
| RAD50 | PIF1 | EXO1 | SAW1 | DIN7 | NHP10 | LIF1 | RAD23 |
| VPS75 | OGG1 | HST3 | FUN30 | SIR4 | NHP6B | MMS2 | MCM3 |
| MGS1 | NSE1 | AHC1 | NTG1 | HTA1 | APN1 | RPB9 | HUG1 |
| IES2 | SSL1 | DNL4 | ELC1 | HTB1 | RAD27 | RAD6 | MMS21 |
| PSY2 | PRP19 | PSF3 | RAD1 | RAD9 | ABF1 | UBC13 | EAF5 |
| POL31 | RTT109 | CTR9 | CHL1 | SPT16 | SLD2 | RPT6 | SNF5 |
| RFA3 | MGM101 | HHT2 | HAT1 | MCM6 | YNK1 | SHU2 | SNF6 |

TABLE 5-continued

Yeast DNA Repair

| | | | | | | | |
|---|---|---|---|---|---|---|---|
| MEC3 | THO2 | REV3 | PHR1 | SAE2 | NUP120 | RAD55 | SPO11 |
| MCM5 | EAF7 | MLH3 | EXO5 | RAD54 | DEF1 | PPH3 | PAF1 |
| NEJ1 | FYV6 | RAD53 | CDC28 | HST4 | PRI2 | RAD28 | DPB3 |
| IRC20 | YAF9 | TFB2 | MEC1 | RVB1 | SHU1 | PSF1 | RIF1 |
| SPT10 | POL1 | MEI5 | RAD16 | CDC1 | IXR1 | MSH4 | HSM3 |
| SRS2 | MKT1 | HRT1 | MMS4 | INO80 | DMC1 | RAD57 | SLX1 |
| DPB11 | PMS1 | PAP2 | RAD17 | SCC2 | PAN3 | BLM10 | TDP1 |
| ARP4 | RAD52 | HMI1 | HHT1 | SAC3 | RAD24 | SMC1 | MCM7 |
| SMC3 | RNH201 | RFC4 | REV1 | HPR1 | RAD3 | BUD27 | RPS3 |
| PSF2 | NSE5 | MSH2 | PDR10 | DPB4 | RAD4 | EPL1 | RVB2 |
| DLS1 | UNG1 | THP1 | SNF2 | PDS1 | SCC4 | ACT1 | |
| PCD1 | RAD33 | YKU70 | POL30 | MSH6 | MAG1 | MLP1 | |
| SLX4 | SPT5 | NTG2 | RDH54 | SAE3 | SLX8 | MGT1 | |

In embodiments, the donor recruitment protein comprises a polypeptide sequence derived from a protein that is recruited to a DNA break, e.g., a double-stranded DNA break. In embodiments, the polypeptide sequence is a portion of the protein that is recruited to a DNA break, in particular the portion of the protein that is responsible for recruitment to the DNA break. In embodiments, the donor recruitment protein comprises a phospho-Ser/Thr-binding domain. In embodiments, the phospho-Ser/Thr-binding domain is a 14-3-3 domain, WW domain, Polo-box domain (in PLK1), WD40 repeat (including those in the E3 ligase SCF$^{\beta TrCP}$), BRCT domain (including those in BRCA1) or FHA domain (such as in CHK2 and MDC1). In embodiments, the donor recruitment protein comprises a polypeptide sequence derived from a protein listed in any of Tables 1-5.

In certain embodiments, an inhibitor of the non-homologous end joining (NHEJ) pathway is used to further increase the frequency of cells genetically modified by HDR. Examples of inhibitors of the NHEJ pathway include any compound (agent) that inhibits or blocks either expression or activity of any protein component in the NHEJ pathway. Protein components of the NHEJ pathway include, but are not limited to, Ku70, Ku86, DNA protein kinase (DNA-PK), Rad50, MRE11, NBS1, DNA ligase IV, and XRCC4. An exemplary inhibitor is wortmannin which inhibits at least one protein component (e.g., DNA-PK) of the NHEJ pathway. Another exemplary inhibitor is Scr7 (5,6-bis((E)-benzylideneamino)-2-mercaptopyrimidin-4-ol), which inhibits joining of DSBs (Maruyama et al. (2015) Nat. Biotechnol. 33(5):538-542, Lin et al. (2016) Sci. Rep. 6:34531). RNA interference or CRISPR-interference may also be used to block expression of a protein component of the NHEJ pathway (e.g., DNA-PK or DNA ligase IV). For example, small interfering RNAs (siRNAs), hairpin RNAs, and other RNA or RNA:DNA species which can be cleaved or dissociated in vivo to form siRNAs may be used to inhibit the NHEJ pathway by RNA interference. Alternatively, deactivated Cas9 (dCas9) together with single guide RNAs (sgRNAs) complementary to the promoter or exonic sequences of genes of the NHEJ pathway can be used in transcriptional repression by CRISPR-interference. Alternatively, an HDR enhancer such as RS-1 may be used to increase the frequency of HDR in cells (Song et al. (2016) Nat. Commun. 7:10548).

Barcoding is accomplished by integrating the genome editing cassette in each transfected cell at a separate chromosomal locus (i.e., the chromosomal barcode locus) from the target locus being edited. The genome editing cassette itself may serve as a barcode to identify genome edits to the cell. Integration at a chromosomal barcode locus avoids problems associated with plasmid instability in retaining the barcode.

In certain embodiments, integration of the genome editing cassette at the chromosomal barcode locus is performed using HDR. A recombinant polynucleotide can be designed with a pair of universal homology arms flanking the genome editing cassette, which are capable of hybridizing to complementary sequences at the chromosomal barcode locus. In addition, each recombinant polynucleotide further comprises a second guide RNA capable of hybridizing at the chromosomal barcode locus. Formation of a complex between this second guide RNA and an RNA-guided nuclease directs the RNA-guided nuclease to the chromosomal barcode locus, wherein the RNA-guided nuclease creates a double-stranded break at the chromosomal barcode locus, and the genome editing cassette is integrated into the chromosomal barcode locus by HDR.

In other embodiments, integration of a genome editing cassette at the chromosomal barcode locus is performed using a site-specific recombinase system. Exemplary site-specific recombinase systems that can be used for this purpose include a Cre-loxP site-specific recombinase system, a Flp-FRT site-specific recombinase system, a PhiC31-att site-specific recombinase system, and a Dre-rox site-specific recombinase system. For a description of these and other site-specific recombinase systems that can be used in the practice of the present disclosure, see, e.g., Wirth et al. (2007) Curr. Opin. Biotechnol. 18(5):411-419; Branda et al. (2004) Dev. Cell 6(1):7-28; Birling et al. (2009) Methods Mol. Biol. 561:245-263; Bucholtz et al. (2008) J. Vis. Exp. May 29 (15) pii: 718; Nern et al. (2011) Proc. Natl. Acad. Sci. U.S.A. 108(34):14198-14203; Smith et al. (2010) Biochem. Soc. Trans. 38(2):388-394; Turan et al. (2011) FASEB J. 25(12):4088-4107; Garcia-Otin et al. (2006) Front. Biosci. 11:1108-1136; Gaj et al. (2014) Biotechnol Bioeng. 111(1):1-15; Krappmann (2014) Appl. Microbiol. Biotechnol. 98(5):1971-1982; Kolb et al. (2002) Cloning Stem Cells 4(1):65-80; and Lopatniuk et al. (2015) J. Appl. Genet. 56(4):547-550; herein incorporated by reference in their entireties.

A recombination target site for a site-specific recombinase is added to the chromosomal barcode locus to allow integration by site-specific recombination. In addition, the recombinant polynucleotide is designed with a matching recombination target site for the site-specific recombinase such that site-specific recombination between the recombination target site on the recombinant polynucleotide and the recombination target site at the chromosomal barcode locus results in integration of the genome editing cassette at the chromosomal barcode locus.

Alternatively or additionally, a unique barcode may be used to identify each guide-RNA-donor polynucleotide pair used in multiplex genome editing. Such barcodes may be inserted into the chromosomal barcode locus at each round of genome editing to identify the number of rounds of genome editing and the guide-RNAs and/or donor polynucleotides used in genetic modification of a cell.

Barcodes may comprise one or more nucleotide sequences that are used to identify a nucleic acid or cell with which the barcode is associated. Barcodes can be 3-1000 or more nucleotides in length, preferably 10-250 nucleotides in length, and more preferably 10-30 nucleotides in length, including any length within these ranges, such as 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 200, 300, 400, 500, 600, 700, 800, 900, or 1000 nucleotides in length.

In some embodiments, barcodes are also used to identify the position (i.e., positional barcode) of a cell, colony, or sample from which a nucleic acid originated, such as the position of a colony in a cellular array or the position of a well in a multi-well plate. In particular, a barcode may be used to identify the position of a genetically modified cell in a cellular array.

In certain embodiments, barcoder cells are used for high-throughput positional barcoding of genetically modified cells, wherein the barcode sequences are used to identify the colonies from which each gRNA and donor polynucleotide originated. The use of such barcodes allows gRNAs and donor polynucleotides from different cells to be pooled in a single reaction mixture for sequencing while still being able to trace back a particular gRNA-donor polynucleotide combination to the colony from which it originated. Exemplary yeast barcoder cells are described in Smith et al. (2017) Mol. Syst. Biol. 13(2):913, herein incorporated by reference in its entirety.

In certain embodiments, genetically modified cells comprising a gRNA-donor polynucleotide cassette library are initially plated at separate locations in an ordered array. Barcoder cells are plated in a matching array, and gRNA-donor polynucleotide cassettes from each genetically modified cell are introduced into each corresponding barcoder cell. This can be accomplished for example, by mating genetically modified cells with the barcoder cells.

Example 1 describes using the yeast, *Saccharomyces cerevisiae*, for this purpose. *Saccharomyces cerevisiae* exists in both diploid and haploid forms. Mating only occurs between haploid forms of yeast of different mating types, which can be either the a or α mating type. The allele at the MAT locus (either MATa or MATα) determines mating type. Diploid cells result from the mating of MATa and MATα yeast strains. Thus, a haploid genetically modified yeast cell comprising a gRNA-donor polynucleotide cassette can be mated with a haploid barcoder yeast cell to produce a diploid yeast cell comprising both the gRNA-donor polynucleotide cassette and the barcode sequence on separate nucleic acids. For example, genetically modified yeast cells of strain MATα can be mated with barcoder yeast cells of strain MATa. Alternatively, genetically modified yeast cells of strain MATa can be mated with barcoder yeast cells of strain MATα.

Translocation of the gRNA-donor polynucleotide cassette to a position adjacent to a barcode sequence in order to tag the cassette with the barcode may be accomplished with any suitable site-specific recombinase system. Site-specific recombinases catalyze DNA exchange reactions between two recombination target sites. A "recombination target site" is a region of a nucleic acid molecule, typically 30-50 nucleotides in length, comprising a binding site or sequence-specific motif recognized by the site-specific recombinase. Upon binding to the target site, the site-specific recombinase catalyzes recombination of specific sequences of DNA at the target site. The relative orientation of the target sites determines the outcome of recombination, which can result in excision, insertion, inversion, translocation or cassette exchange. Translocation occurs if the recombination target sites are on separate DNA molecules. Site-specific recombinase systems often include tyrosine recombinases or serine recombinases, but other types of site-specific recombinases may also be used along with their specific recombination target sites. Exemplary site-specific recombinase systems include Cre-loxP, Flp-FRT, PhiC31-att, and Dre-rox site-specific recombinase systems.

A recombination target site for a site-specific recombinase can be added to a gRNA-donor polynucleotide cassette in a number of ways. For example, a polynucleotide comprising the gRNA-donor cassette can be amplified with a primer comprising a recombination target site capable of undergoing recombination with the recombination target site of a barcoder cell. Alternatively, a gRNA-donor polynucleotide cassette can be integrated into the genome or a plasmid of a host cell at a locus adjacent to a recombination target site capable of undergoing recombination with the recombination target site of a barcoder cell to produce a barcode-gRNA-donor polynucleotide fusion sequence. In addition, a selectable marker may be used that selects for clones that have undergone successful site-specific recombination.

In some instances, a population of cells may be enriched for those comprising a genetic modification by separating the genetically modified cells from the remaining population. Separation of genetically modified cells typically relies upon the expression of a selectable marker co-integrated with the intended edit at the target locus. After integration of a donor polynucleotide by HDR, positive selection is performed to isolate cells from a population, e.g. to create an enriched population of cells comprising the genetic modification.

Cell separation may be accomplished by any convenient separation technique appropriate for the selection marker used, including, but not limited to flow cytometry, fluorescence activated cell sorting (FACS), magnetic-activated cell sorting (MACS), elutriation, immunopurification, and affinity chromatography. For example, if a fluorescent marker is used, cells may be separated by fluorescence activated cell sorting (FACS), whereas if a cell surface marker is used, cells may be separated from the heterogeneous population by affinity separation techniques, e.g. MACS, affinity chromatography, "panning" with an affinity reagent attached to a solid matrix, immunopurification with an antibody specific for the cell surface marker, or other convenient technique.

In certain embodiments, positive or negative selection of genetically modified cells is performed using a binding agent that specifically binds to a selection marker on a cell (e.g., such as produced from a selection marker expression cassette included in a donor polynucleotide). Examples of binding agents include, without limitation, antibodies, antibody fragments, antibody mimetics, and aptamers. In some embodiments, the binding agent binds to the selection marker with high affinity. The binding agent may be immobilized on a solid support to facilitate isolation of genetically modified cells from a liquid culture. Exemplary solid supports include a magnetic bead, a non-magnetic bead, a slide, a gel, a membrane, and a microtiter plate well.

In certain embodiments, the binding agent comprises an antibody that specifically binds to the selection marker on a cell. Any type of antibody may be used, including polyclonal and monoclonal antibodies, hybrid antibodies, altered antibodies, chimeric antibodies and, humanized antibodies, as well as: hybrid (chimeric) antibody molecules (see, for example, Winter et al. (1991) *Nature* 349:293-299; and U.S. Pat. No. 4,816,567); F(ab')$_2$ and F(ab) fragments; F$_v$ molecules (noncovalent heterodimers, see, for example, Inbar et al. (1972) *Proc Natl Acad Sci USA* 69:2659-2662; and Ehrlich et al. (1980) *Biochem* 19:4091-4096); single-chain Fv molecules (sFv) (see, e.g., Huston et al. (1988) *Proc Natl Acad Sci USA* 85:5879-5883); nanobodies or single-domain antibodies (sdAb) (see, e.g., Wang et al. (2016) *Int J Nanomedicine* 11:3287-3303, Vincke et al. (2012) *Methods Mol Biol* 911:15-26; dimeric and trimeric antibody fragment constructs; minibodies (see, e.g., Pack et al. (1992) *Biochem* 31:1579-1584; Cumber et al. (1992) *J Immunology* 149B: 120-126); humanized antibody molecules (see, e.g., Riechmann et al. (1988) *Nature* 332:323-327; Verhoeyan et al. (1988) *Science* 239:1534-1536; and U.K. Patent Publication No. GB 2,276,169, published 21 Sep. 1994); and, any functional fragments obtained from such molecules, wherein such fragments retain specific-binding properties of the parent antibody molecule (i.e., specifically binds to a selection marker on a cell).

In other embodiments, the binding agent comprises an aptamer that specifically binds to the selection marker on a cell. Any type of aptamer may be used, including a DNA, RNA, xeno-nucleic acid (XNA), or peptide aptamer that specifically binds to the target antibody isotype. Such aptamers can be identified, for example, by screening a combinatorial library. Nucleic acid aptamers (e.g., DNA or RNA aptamers) that bind selectively to a target antibody isotype can be produced by carrying out repeated rounds of in vitro selection or systematic evolution of ligands by exponential enrichment (SELEX). Peptide aptamers that bind to a selection marker on a cell may be isolated from a combinatorial library and improved by directed mutation or repeated rounds of mutagenesis and selection. For a description of methods of producing aptamers, see, e.g., *Aptamers: Tools for Nanotherapy and Molecular Imaging* (R. N. Veedu ed., Pan Stanford, 2016), *Nucleic Acid and Peptide Aptamers: Methods and Protocols* (Methods in Molecular Biology, G. Mayer ed., Humana Press, 2009), *Nucleic Acid Aptamers: Selection, Characterization, and Application* (Methods in Molecular Biology, G. Mayer ed., Humana Press, 2016), *Aptamers Selected by Cell-SELEX for Theranostics* (W. Tan, X. Fang eds., Springer, 2015), Cox et al. (2001) Bioorg. Med. Chem. 9(10):2525-2531; Cox et al. (2002) Nucleic Acids Res. 30(20): e108, Kenan et al. (1999) Methods Mol Biol. 118:217-231; Platella et al. (2016) Biochim. Biophys. Acta November 16 pii: S0304-4165(16)30447-0, and Lyu et al. (2016) Theranostics 6(9):1440-1452; herein incorporated by reference in their entireties.

In yet other embodiments, the binding agent comprises an antibody mimetic. Any type of antibody mimetic may be used, including, but not limited to, affibody molecules (Nygren (2008) FEBS J. 275 (11):2668-2676), affilins (Ebersbach et al. (2007) J. Mol. Biol. 372 (1):172-185), affimers (Johnson et al. (2012) Anal. Chem. 84 (15):6553-6560), affitins (Krehenbrink et al. (2008) J. Mol. Biol. 383 (5): 1058-1068), alphabodies (Desmet et al. (2014) Nature Communications 5:5237), anticalins (Skerra (2008) FEBS J. 275 (11):2677-2683), avimers (Silverman et al. (2005) Nat. Biotechnol. 23 (12):1556-1561), darpins (Stumpp et al. (2008) Drug Discov. Today 13 (15-16):695-701), fynomers (Grabulovski et al. (2007) J. Biol. Chem. 282 (5):3196-3204), and monobodies (Koide et al. (2007) Methods Mol. Biol. 352:95-109).

In positive selection, cells carrying a selection marker are collected, whereas in negative selection, cells carrying a selection marker are removed from a cell population. For example, in positive selection, a binding agent specific for a surface marker can be immobilized on a solid support (e.g., column or magnetic bead) and used to collect cells of interest on the solid support. Cells that are not of interest do not bind to the solid support (e.g., flow through the column or do not attach to the magnetic beads). In negative selection, the binding agent is used to deplete a cell population of cells that are not of interest. The cells of interest are those that do not bind to the binding agent (e.g., flow through the column or remain after the magnetic beads are removed).

Dead cells may be selected against by employing dyes that preferentially stain dead cells (e.g. propidium iodide). Any technique may be employed which is not unduly detrimental to the viability of the genetically modified cells.

Compositions that are highly enriched for cells having a desired genetic modification can be produced in this manner. By "highly enriched" is meant that the genetically modified cells are 70% or more, 75% or more, 80% or more, 85% or more, 90% or more, or 95% or more, or 98% or more of the cell composition. In other words, the composition may be a substantially pure composition of genetically modified cells.

Genetically modified cells produced by the methods described herein may be used immediately. Alternatively, the cells may be frozen at liquid nitrogen temperatures and stored for long periods of time before being thawed and used. In such cases, cells may be frozen in 10% DMSO, 50% serum, 40% buffered medium, or some other such solution as is commonly used in the art to preserve cells at such freezing temperatures, and thawed in a manner as commonly known in the art for thawing frozen cultured cells.

The method steps using an RNA-guided nuclease, genome modification vectors comprising expression cassettes encoding guide RNAs and donor polynucleotides, and barcoding with barcoder cells, as described herein, can be repeated to provide any desired number of DNA modifications with barcoding.

Provided herein is a method for multiplex production of genetically engineered cells, the method including: (a) transfecting a plurality of cells with plurality of different recombinant polynucleotides, each recombinant polynucleotide including a genome editing cassette including a first nucleic acid sequence encoding a first guide RNA (gRNA) capable of hybridizing at a genomic target locus to be modified and a donor polynucleotide thereby forming a gRNA-donor polynucleotide combination, where each recombinant polynucleotide includes a different genome editing cassette including a different gRNA-donor polynucleotide combination, and allowing each of the cells to express the first nucleic acid sequence thereby forming the gRNA; and (b) introducing an RNA-guided nuclease into each of the plurality of cells, where the RNA-guided nuclease in each cell forms a complex with the gRNA thereby forming a gRNA-RNA-guided nuclease complex, and allowing the gRNA-RNA-guided nuclease complex to modify the genomic target locus by integrating the donor polynucleotide into the genomic target locus, thereby producing a plurality of genetically engineered cells.

In another aspect is provided a method for multiplex production of genetically engineered cells, the method including: (a) transfecting a plurality of cells with plurality of different recombinant polynucleotides, each recombinant polynucleotide including a unique polynucleotide barcode and a genome editing cassette including a first nucleic acid sequence encoding a first guide RNA (gRNA) capable of hybridizing at a genomic target locus to be modified and a donor polynucleotide thereby forming a gRNA-donor polynucleotide combination, where each recombinant polynucleotide includes a different genome editing cassette including a different gRNA-donor polynucleotide combination, and allowing each of the cells to express the first nucleic acid sequence thereby forming the gRNA; and (b) introducing an RNA-guided nuclease into each of the plurality of cells, where the RNA-guided nuclease in each cell forms a complex with the gRNA thereby forming a gRNA-RNA-guided nuclease complex, and allowing the gRNA-RNA-guided nuclease complex to modify the genomic target locus by integrating the donor polynucleotide into the genomic target locus, thereby producing a plurality of genetically engineered cells.

In embodiments, the method further includes sequence verification and arraying of the plurality of genetically modified cells, the method including: (c) plating the plurality of genetically modified cells in an ordered array on media suitable for growth of the genetically modified cells; (d) culturing the plurality of genetically modified cells under conditions whereby each genetically modified cell produces a colony of clones in the ordered array; (e) introducing a genome editing cassette from a colony in the ordered array into a barcoder cell, where the barcoder cell includes a nucleic acid including a recombination target site for a site-specific recombinase and a barcode sequence that identifies the position of the colony in the ordered array to which the genome editing cassette corresponds; (f) translocating the genome editing cassette to a position adjacent to the barcode sequence of the barcoder cell using a site-specific recombinase system, where site-specific recombination with the recombination target site of the barcoder cell generates a nucleic acid including the barcode sequence linked to the genome editing cassette; (g) sequencing the nucleic acid including the barcode sequence of the barcoder cell linked to the genome editing cassette to identify the sequences of the guide RNA and the donor polynucleotide of the genome editing cassette from the colony, where the barcode sequence of the barcoder cell is used to identify the position of the colony in the ordered array from which the genome editing cassette originated; and (h) picking a clone including the genome editing cassette from the colony in the ordered array identified by the barcode of the barcoder cell. In embodiments, the method further includes repeating (e) through (h) with all the colonies in the ordered array to identify the sequences of the guide RNAs and the donor polynucleotides of the genome editing cassettes for every colony in the ordered array.

In embodiments, each recombinant polynucleotide further comprises a second nucleic acid sequence encoding the RNA-guided nuclease. In embodiments, the RNA-guided nuclease is provided by a vector or a second nucleic acid sequence integrated into the genome of the cells. In embodiments, the genome editing cassette and the RNA-guided nuclease are provided by a single vector or separate vectors.

In embodiments, the method further includes identifying the presence of the donor polynucleotide in at least one of the plurality of genetically engineered cells. In embodiments, identifying the presence of the donor polynucleotide includes identifying the barcode.

In embodiments, the barcodes are inserted into the genomes of the plurality of genetically engineered cells at a chromosomal barcode locus.

In embodiments, the RNA-guided nuclease is provided by a second nucleic acid sequence integrated into a chromosomal barcode locus, and further wherein the insertion of the barcodes at the chromosomal barcode locus removes the second nucleic acid sequence from the chromosomal barcode locus.

In embodiments, the chromosomal barcode locus further comprises a promoter that becomes operably linked to the first nucleic acid sequence of any genome editing cassette that integrates at the chromosomal barcode locus.

In embodiments, each recombinant polynucleotide is provided by a vector. In embodiments, the vector comprises a promoter that is operably linked to the polynucleotide encoding the gRNA. In embodiments, the promoter is a constitutive or inducible promoter. In embodiments, the vector is a plasmid or viral vector. In embodiments, the vector is a high copy number vector.

In embodiments, the RNA-guided nuclease is a Cas nuclease or an engineered RNA-guided FokI-nuclease. In embodiments, the Cas nuclease is Cas9 or Cpf1.

In embodiments, each recombinant polynucleotide further comprises a second nucleic acid sequence encoding a second guide RNA (guide X) capable of hybridizing with the recombinant polynucleotide, wherein the guide X forms a complex with a nuclease in each cell such that the guide X-nuclease complex cleaves the recombinant polynucleotide. In embodiments, the recombinant polynucleotide is a plasmid vector and the guide X-nuclease complex linearizes the plasmid vector. In embodiments, the guide X-nuclease complex integrates at least a portion of the recombinant polynucleotide into the chromosomal barcode locus. In embodiments, the nuclease is the RNA-guided nuclease. In embodiments, the nuclease is a second RNA-guided nuclease that is introduced into the cell. In embodiments, the second RNA-guided nuclease is a Cas nuclease or an engineered RNA-guided FokI-nuclease. In embodiments, wherein the nuclease is selected from a meganuclease, a FokI-nuclease, a CRISPR-associated nuclease, a zinc finger nuclease (ZFN), and a transcription activator-like effector-based nuclease (TALEN).

In embodiments, wherein the donor polynucleotide is a donor DNA.

In embodiments, each recombinant polynucleotide further comprises a DNA binding sequence known to bind a DNA binding domain.

In embodiments, the method further includes introducing into the cells a donor recruitment protein comprising the DNA binding domain and a DNA break site localizing domain that selectively recruits the donor recruitment protein to a DNA break.

In embodiments, the chromosomal barcode locus comprises a polynucleotide encoding the RNA-guided nuclease, the nuclease, and/or the donor recruitment protein; and further wherein the insertion of the barcode at the chromosomal barcode locus removes the polynucleotide encoding the RNA-guided nuclease, the nuclease, and/or the donor recruitment protein from the chromosomal barcode locus.

In embodiments, each donor polynucleotide introduces a different mutation into the genomic DNA. In embodiments, the mutation is selected from the group consisting of an insertion, deletion, and substitution.

In embodiments, at least one donor polynucleotide introduces a mutation that inactivates a gene in the genomic DNA.

In embodiments, at least one donor polynucleotide removes a mutation from a gene in the genomic DNA.

In embodiments, the plurality of recombinant polynucleotides is capable of producing mutations at multiple sites within a single gene or non-coding region. In embodiments, the plurality of recombinant polynucleotides is capable of producing mutations at multiple sites in different genes or non-coding regions.

In embodiments, the method further includes using a selectable marker that selects for clones that have undergone successful integration of the donor polynucleotide at the genomic target locus or successful integration of the genome editing cassette at the chromosomal barcode locus.

In embodiments, the cells are yeast cells. In embodiments, the yeast cells are haploid yeast cells. In embodiments, the yeast cells are diploid yeast cells.

In embodiments, the method further includes inhibiting non-homologous end joining (NHEJ).

In embodiments, the genetically modified cells are haploid yeast cells and the barcoder cells are haploid yeast cells capable of mating with the genetically modified cells.

In embodiments, introducing a genome editing cassette from a colony in the ordered array into a barcoder cell comprises mating the clone from the colony with the barcoder cell to produce a diploid yeast cell. In embodiments, the genetically modified cells are of strain MATα and the barcoder yeast cells are of strain MATa. In embodiments, the genetically modified cells are of strain MATa and the barcoder yeast cells are of strain MATα.

In embodiments, the genome editing cassette is flanked by restriction sites recognized by a meganuclease. In embodiments, the recombinase system in the barcoder cell uses the meganuclease to generate a DNA double-strand break.

In embodiments, the recombinase system in the barcoder cell is a Cre-loxP site-specific recombinase system, a Flp-FRT site-specific recombinase system, a PhiC31-att site-specific recombinase system, or a Dre-rox site-specific recombinase system.

In another aspect is provided an ordered array of colonies comprising clones of the genetically modified cells produced by the method described herein, wherein the colonies are indexed according to the verified sequences of their guide RNAs and donor polynucleotides.

In another aspect is provided a method for localizing a donor polynucleotide to a genomic target locus in a cell, the method including: (a) transfecting a cell with a recombinant polynucleotide, the recombinant polynucleotide including a genome editing cassette including a donor polynucleotide and a DNA binding sequence known to bind a DNA binding domain; (b) introducing a nuclease into the cell, where the nuclease recognizes and causes a DNA break at the genomic target locus; (c) introducing a donor recruitment protein into the cell, the donor recruitment protein including the DNA binding domain and a DNA break site localizing domain and allowing the donor recruitment protein to selectively recruit the DNA break, thereby localizing the donor polynucleotide to the genomic target locus. In embodiments, the DNA break is a double-strand break.

In embodiments, the donor polynucleotide is localized to the genomic target locus by loading of DNA repair enzymes onto the donor DNA. In embodiments, the donor polynucleotide is localized to the genomic target locus by interaction of the donor recruitment protein with one or more agents (e.g., DNA repair enzymes, DNA break binding proteins, and/or agents that are produced at or recuited to a DNA break) at the genomic target locus.

In embodiments, the donor recruitment protein is a fusion protein.

In embodiments, the DNA binding domain comprises a polypeptide sequence from a DNA binding protein. In embodiments, the DNA binding protein is selected from LexA, Gal4 DBD, Zinc Finger protein, TALE, and a transcription factor. In embodiments, the DNA binding protein is streptavidin, and wherein biotin is conjugated to the donor polynucleotide. The DNA binding protein may include any protein known to bind DNA at a known DNA sequence.

In embodiments, the DNA break site localizing domain comprises a polypeptide sequence from a protein that binds to a DNA break site, e.g., double-strand DNA break site, or a region near a DNA break site as a result of the DNA break. In embodiments, the protein that binds to a DNA break site or a region near a DNA break site as a result of the DNA break is a protein that is involved in DNA repair. In embodiments, the protein that is involved in DNA repair is selected from a DNA break binding protein, a FOX transcription factor, and a protein from Table 1, Table 2, Table 3, Table 4, or Table 5.

In embodiments, the nuclease is selected from a meganuclease, a FokI-nuclease, a CRISPR-associated nuclease, a zinc finger nuclease (ZFN), and a transcription activator-like effector-based nuclease (TALEN).

In embodiments, the nuclease is a RNA-guided nuclease.

In embodiments, the nuclease modifies the genomic target locus by integrating the donor polynucleotide into the genomic target locus, thereby producing a genetically engineered cell.

In embodiments, the genetically engineered cell is a genetically engineered therapeutic cell. In embodiments, the genetically engineered therapeutic cell is a genetically engineered immune cell. In embodiments, the genetically engineered immune cell is a T cell or a natural killer cell that targets a cancer.

In another aspect is provided a gene editing vector, including a genome editing cassette including (i) a barcode, (ii) a first nucleic acid sequence encoding a first guide RNA (gRNA) capable of hybridizing at a genomic target locus to be modified, and (iii) a donor polynucleotide, thereby forming a barcode-gRNA-donor polynucleotide combination.

In another aspect is provided a gene editing vector, including a genome editing cassette including (i) a first nucleic acid sequence encoding a first guide RNA (gRNA) capable of hybridizing at a genomic target locus to be modified, and (ii) a donor polynucleotide, thereby forming a gRNA-donor polynucleotide combination.

In another aspect is provided a library of gene editing vectors, each gene editing vector including a genome editing cassette including (i) a barcode, (ii) a first nucleic acid sequence encoding a first guide RNA (gRNA) capable of hybridizing at a genomic target locus to be modified, and (iii) a donor polynucleotide, thereby forming a barcode-gRNA-donor polynucleotide combination; where each recombinant polynucleotide includes a different genome editing cassette including a different barcode-gRNA-donor polynucleotide combination.

In another aspect is provided a library of gene editing vectors, each gene editing vector including a genome editing cassette including (i) a first nucleic acid sequence encoding a first guide RNA (gRNA) capable of hybridizing at a genomic target locus to be modified, and (ii) a donor polynucleotide, thereby forming a gRNA-donor polynucleotide combination; where each recombinant polynucleotide includes a different genome editing cassette including a different gRNA-donor polynucleotide combination.

In embodiments, each vector further includes a polynucleotide encoding a second guide RNA (guide X) capable of hybridizing with the vector. In embodiments, the guide X is capable of hybridizing with the chromosomal barcode locus.

In embodiments, each vector further includes a DNA binding sequence known to bind a DNA binding moiety.

In embodiments, each vector further includes a polynucleotide encoding a RNA-guided nuclease.

In another aspect is provided a gene editing vector including a donor polynucleotide and a first nucleic acid sequence encoding a first guide RNA (guide X) capable of hybridizing with the vector at a target site such that when the guide X is expressed by a cell, the guide X hybridizes to the vector and creates a DNA break at the target site. In embodiments, the vector includes a second nucleic acid sequence encoding a second guide RNA (gRNA) capable of hybridizing at a genomic target locus to be modified. In embodiments, the vector includes a DNA binding sequence known to bind a DNA binding domain. In embodiments, the vector includes a polynucleotide encoding a nuclease. In embodiments, the nuclease is selected from a meganuclease, a FokI-nuclease, a CRISPR-associated nuclease, a zinc finger nuclease (ZFN), and a transcription activator-like effector-based nuclease (TALEN).

In another aspect is provided a kit including: (a) a gene editing vector as described herein including embodiments thereof; and (b) a nuclease or a polynucleotide encoding a nuclease.

In another aspect is provided a kit including: (a) a gene editing vector as described herein including embodiments thereof; and (b) a reagent for genetically modifying a cell.

In embodiments, each recombinant polynucleotide further comprises a second nucleic acid sequence encoding the RNA-guided nuclease.

In another aspect is provided a composition comprising a target cell, a nuclease, and a gene editing vector as described herein. In embodiments, the composition includes a donor recruitment protein, the donor recruitment protein comprising a DNA binding moiety and a DNA break site localizing moiety that selectively recruits the donor recruitment protein to a DNA break site. In embodiments, the target cell is a cell from a subject. In embodiments, the subject has cancer.

In embodiments, the target cell is an immune cell. In embodiments, the immune cell is a T cell.

In embodiments, the donor polynucleotide encodes a therapeutic agent. In embodiments, the therapeutic agent is a chimeric antigen receptor or a T cell receptor.

In embodiments, the subject has a disease that can be treated by incorporating the donor DNA into the genome of the cell.

In embodiments, the cell is a human cell. In embodiments, the subject is human.

B. Nucleic Acids Encoding Donor Polynucleotides, Guide RNAs, and RNA-Guided Nucleases In certain embodiments, the gRNA-donor polynucleotide cassettes and/or RNA-guided nucleases are expressed in vivo from a vector. A "vector" is a composition of matter which can be used to deliver a nucleic acid of interest to the interior of a cell. The gRNA-donor polynucleotide cassettes and the RNA-guided nuclease can be introduced into a cell with a single vector or in separate vectors. The ability of constructs to produce the donor polynucleotides, guide RNAs, and the RNA-guided nuclease (e.g., Cas9) and genetically modify cells can be empirically determined (e.g., see Example 1 describing the use nutritional markers such as FCY1 and HIS3 for detection of genetically modified yeast cells).

Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, lentiviral vectors, and the like. An expression construct can be replicated in a living cell, or it can be made synthetically. For purposes of this application, the terms "expression construct," "expression vector," and "vector," are used interchangeably to demonstrate the application of the present disclosure in a general, illustrative sense, and are not intended to limit the disclosure.

In certain embodiments, the nucleic acid encoding a polynucleotide of interest is under transcriptional control of a promoter. A "promoter" refers to a DNA sequence recognized by the synthetic machinery of the cell, or introduced synthetic machinery, required to initiate the specific transcription of a gene. The term promoter will be used here to refer to a group of transcriptional control modules that are clustered around the initiation site for RNA polymerase I, II, or III. Typical promoters for mammalian cell expression include the SV40 early promoter, a CMV promoter such as the CMV immediate early promoter (see, U.S. Pat. Nos. 5,168,062 and 5,385,839, incorporated herein by reference in their entireties), the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. These and other promoters can be obtained from commercially available plasmids, using techniques well known in the art. See, e.g., Sambrook et al., supra. Enhancer elements may be used in association with the promoter to increase expression levels of the constructs. Examples include the SV40 early gene enhancer, as described in Dijkema et al., *EMBO J.* (1985) 4:761, the enhancer/promoter derived from the long terminal repeat (LTR) of the Rous Sarcoma Virus, as described in Gorman et al., *Proc. Natl. Acad. Sci. USA* (1982b) 79:6777 and elements derived from human CMV, as described in Boshart et al., *Cell* (1985) 41:521, such as elements included in the CMV intron A sequence.

In one embodiment, an expression vector for expressing a donor polynucleotide, gRNA, or an RNA-guided nuclease (e.g., Cas9) comprises a promoter "operably linked" to a polynucleotide encoding the donor polynucleotide, gRNA, or RNA-guided nuclease. The phrase "operably linked" or "under transcriptional control" as used herein means that the promoter is in the correct location and orientation in relation to a polynucleotide to control the initiation of transcription by RNA polymerase and expression of the donor polynucleotide, gRNA, or RNA-guided nuclease.

Typically, transcription terminator/polyadenylation signals will also be present in the expression construct. Examples of such sequences include, but are not limited to, those derived from SV40, as described in Sambrook et al., supra, as well as a bovine growth hormone terminator sequence (see, e.g., U.S. Pat. No. 5,122,458). Additionally, 5'-UTR sequences can be placed adjacent to the coding sequence in order to enhance expression of the same. Such sequences may include UTRs comprising an internal ribosome entry site (IRES).

Inclusion of an IRES permits the translation of one or more open reading frames from a vector. The IRES element attracts a eukaryotic ribosomal translation initiation complex and promotes translation initiation. See, e.g., Kaufman et al., *Nuc. Acids Res.* (1991) 19:4485-4490; Gurtu et al., Biochem. Biophys. Res. Comm. (1996) 229:295-298; Rees et al., BioTechniques (1996) 20:102-110; Kobayashi et al., BioTechniques (1996) 21:399-402; and Mosser et al., BioTechniques (1997 22 150-161. A multitude of IRES sequences are known and include sequences derived from a wide variety of viruses, such as from leader sequences of picornaviruses such as the encephalomyocarditis virus (EMCV) UTR (fang et al. J. Virol. (1989) 63:1651-1660), the polio leader sequence, the hepatitis A virus leader, the hepatitis C virus IRES, human rhinovirus type 2 IRES (Dobrikova et al., Proc. Natl. Acad. Sci. (2003) 100(25): 15125-15130), an IRES element from the foot and mouth disease virus (Ramesh et al., Nucl. Acid Res. (1996) 24:2697-2700), a giardiavirus IRES (Garlapati et al., J. Biol. Chem. (2004) 279(5):3389-3397), and the like. A variety of nonviral IRES sequences will also find use herein, including, but not limited to IRES sequences from yeast, as well as the human angiotensin II type 1 receptor IRES (Martin et al., Mol. Cell Endocrinol. (2003) 212:51-61), fibroblast growth factor IRESs (FGF-1 IRES and FGF-2 IRES, Martineau et al. (2004) Mol. Cell. Biol. 24(17):7622-7635), vascular endothelial growth factor IRES (Baranick et al. (2008) Proc. Natl. Acad. Sci. U.S.A. 105(12):4733-4738, Stein et al. (1998) Mol. Cell. Biol. 18(6):3112-3119, Bert et al. (2006) RNA 12(6):1074-1083), and insulin-like growth factor 2 IRES (Pedersen et al. (2002) Biochem. J. 363(Pt 1):37-44). These elements are readily commercially available in plasmids sold, e.g., by Clontech (Mountain View, CA), Invivogen (San Diego, CA), Addgene (Cambridge, MA) and GeneCopoeia (Rockville, MD). See also IRESite: The database of experimentally verified IRES structures (iresite.org). An IRES sequence may be included in a vector, for example, to express multiple selection markers or an RNA-guided nuclease (e.g., Cas9) in combination with one or more selection markers from an expression cassette.

Alternatively, a polynucleotide encoding a viral T2A peptide can be used to allow production of multiple protein products (e.g., Cas9, one or more selection markers) from a single vector. 2A linker peptides are inserted between the coding sequences in the multicistronic construct. The 2A peptide, which is self-cleaving, allows co-expressed proteins from the multicistronic construct to be produced at equimolar levels. 2A peptides from various viruses may be used, including, but not limited to 2A peptides derived from the foot-and-mouth disease virus, equine rhinitis A virus, Thosea asigna virus and porcine teschovirus-1. See, e.g., Kim et al. (2011) PLoS One 6(4):e18556, Trichas et al. (2008) BMC Biol. 6:40, Provost et al. (2007) Genesis 45(10):625-629, Furler et al. (2001) Gene Ther. 8(11):864-873; herein incorporated by reference in their entireties.

In certain embodiments, the expression construct comprises a plasmid suitable for transforming a yeast cell. Yeast expression plasmids typically contain a yeast-specific origin of replication (ORI) and nutritional selection markers (e.g., HIS3, URA3, LYS2, LEU2, TRP1, MET15, ura4+, leu1+, ade6+), antibiotic selection markers (e.g., kanamycin resistance), fluorescent markers (e.g., mCherry), or other markers for selection of transformed yeast cells. The yeast plasmid may further contain components to allow shuttling between a bacterial host (e.g., E. coli) and yeast cells. A number of different types of yeast plasmids are available including yeast integrating plasmids (YIp), which lack an ORI and are integrated into host chromosomes by homologous recombination; yeast replicating plasmids (YRp), which contain an autonomously replicating sequence (ARS) and can replicate independently; yeast centromere plasmids (YCp), which are low copy vectors containing a part of an ARS and part of a centromere sequence (CEN); and yeast episomal plasmids (YEp), which are high copy number plasmids comprising a fragment from a 2 micron circle (a natural yeast plasmid) that allows for 50 or more copies to be stably propagated per cell.

Alternatively, a bacterial plasmid vector may be used to transform a bacterial host. Numerous bacterial expression vectors are known to those of skill in the art, and the selection of an appropriate vector is a matter of choice. Bacterial expression vectors include, but are not limited to, pACYC177, pASK75, pBAD, pBADM, pBAT, pCal, pET, pETM, pGAT, pGEX, pHAT, pKK223, pMal, pProEx, pQE, and pZA31 vectors. See, e.g., Sambrook et al., supra.

In other embodiments, the expression construct comprises a virus or engineered construct derived from a viral genome. A number of viral based systems have been developed for gene transfer into mammalian cells. These include adenoviruses, retroviruses (γ-retroviruses and lentiviruses), poxviruses, adeno-associated viruses, baculoviruses, and herpes simplex viruses (see e.g., Warnock et al. (2011) Methods Mol. Biol. 737:1-25; Walther et al. (2000) Drugs 60(2):249-271; and Lundstrom (2003) Trends Biotechnol. 21(3):117-122; herein incorporated by reference in their entireties). The ability of certain viruses to enter cells via receptor-mediated endocytosis, to integrate into host cell genomes and express viral genes stably and efficiently have made them attractive candidates for the transfer of foreign genes into mammalian cells.

For example, retroviruses provide a convenient platform for gene delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; Boris-Lawrie and Temin (1993) Cur. Opin. Genet. Develop. 3:102-109; and Ferry et al. (2011) Curr. Pharm. Des. 17(24):2516-2527). Lentiviruses are a class of retroviruses that are particularly useful for delivering polynucleotides to mammalian cells because they are able to infect both dividing and nondividing cells (see e.g., Lois et al (2002) Science 295:868-872; Durand et al. (2011) Viruses 3(2):132-159; herein incorporated by reference).

A number of adenovirus vectors have also been described. Unlike retroviruses which integrate into the host genome, adenoviruses persist extrachromosomally thus minimizing the risks associated with insertional mutagenesis (Haj-Ahmad and Graham, J. Virol. (1986) 57:267-274; Bett et al., J. Virol. (1993) 67:5911-5921; Mittereder et al., Human Gene Therapy (1994) 5:717-729; Seth et al., J. Virol. (1994) 68:933-940; Barr et al., Gene Therapy (1994) 1:51-58; Berkner, K. L. BioTechniques (1988) 6:616-629; and Rich et al., Human Gene Therapy (1993) 4:461-476). Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., Molec. Cell. Biol. (1988) 8:3988-3996; Vincent et al., Vaccines 90 (1990) (Cold Spring Harbor Laboratory Press); Carter, B. J. Current Opinion in Biotechnology (1992) 3:533-539; Muzyczka, N. Current Topics in Microbiol. and Immunol. (1992) 158:97-129; Kotin, R. M. Human Gene Therapy (1994) 5:793-801; Shelling and Smith, Gene Therapy (1994) 1:165-169; and Zhou et al., J. Exp. Med. (1994) 179:1867-1875.

Another vector system useful for delivering the polynucleotides of the present disclosure is the enterically administered recombinant poxvirus vaccines described by Small, Jr., P. A., et al. (U.S. Pat. No. 5,676,950, issued Oct. 14, 1997, herein incorporated by reference).

Additional viral vectors which will find use for delivering the nucleic acid molecules of interest include those derived from the pox family of viruses, including vaccinia virus and avian poxvirus. By way of example, vaccinia virus recombinants expressing a nucleic acid molecule of interest (e.g., a donor polynucleotide, gRNA, or RNA-guided nuclease) can be constructed as follows. The DNA encoding the particular nucleic acid sequence is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the sequences of interest into the viral genome. The resulting TK-recombinant can be selected by culturing the cells in the presence of 5-bromodeoxyuridine and picking viral plaques resistant thereto.

Alternatively, avipoxviruses, such as the fowlpox and canarypox viruses, can also be used to deliver the nucleic acid molecules of interest. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al., J. Biol. Chem. (1993) 268:6866-6869 and Wagner et al., Proc. Natl. Acad. Sci. USA (1992) 89:6099-6103, can also be used for gene delivery.

Members of the alphavirus genus, such as, but not limited to, vectors derived from the Sindbis virus (SIN), Semliki Forest virus (SFV), and Venezuelan Equine Encephalitis virus (VEE), will also find use as viral vectors for delivering the polynucleotides of the present disclosure. For a description of Sindbis-virus derived vectors useful for the practice of the instant methods, see, Dubensky et al. (1996) J. Virol. 70:508-519; and International Publication Nos. WO 95/07995, WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998, both herein incorporated by reference. Particularly preferred are chimeric alphavirus vectors comprised of sequences derived from Sindbis virus and Venezuelan equine encephalitis virus. See, e.g., Perri et al. (2003) J. Virol. 77: 10394-10403 and International Publication Nos. WO 02/099035, WO 02/080982, WO 01/81609, and WO 00/61772; herein incorporated by reference in their entireties.

A vaccinia based infection/transfection system can be conveniently used to provide for inducible, transient expression of the polynucleotides of interest (e.g., gRNAs-donor polynucleotide cassettes, polynucleotides encoding RNA guided nucleases) in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA. The method provides for high level, transient, cytoplasmic production of large quantities of RNA. See, e.g., Elroy-Stein and Moss, Proc. Natl. Acad. Sci. USA (1990) 87:6743-6747; Fuerst et al., Proc. Natl. Acad. Sci. USA (1986) 83:8122-8126.

As an alternative approach to infection with vaccinia or avipox virus recombinants, or to the delivery of nucleic acids using other viral vectors, an amplification system can be used that will lead to high level expression following introduction into host cells. Specifically, a T7 RNA polymerase promoter preceding the coding region for T7 RNA polymerase can be engineered. Translation of RNA derived from this template will generate T7 RNA polymerase which in turn will transcribe more templates. Concomitantly, there will be a cDNA whose expression is under the control of the T7 promoter. Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the template(s) to prime the transcription reaction. The polymerase can be introduced as a protein or on a plasmid encoding the RNA polymerase. For a further discussion of T7 systems and their use for transforming cells, see, e.g., International Publication No. WO 94/26911; Studier and Moffatt, J. Mol. Biol. (1986) 189:113-130; Deng and Wolff, Gene (1994) 143:245-249; Gao et al., Biochem. Biophys. Res. Commun. (1994) 200:1201-1206; Gao and Huang, Nuc. Acids Res. (1993) 21:2867-2872; Chen et al., Nuc. Acids Res. (1994) 22:2114-2120; and U.S. Pat. No. 5,135, 855.

Insect cell expression systems, such as baculovirus systems, can also be used and are known to those of skill in the art and described in, e.g., *Baculovirus and Insect Cell Expression Protocols* (Methods in Molecular Biology, D. W. Murhammer ed., Humana Press, 2$^{nd}$ edition, 2007) and L. King *The Baculovirus Expression System: A laboratory guide* (Springer, 1992). Materials and methods for baculovirus/insect cell expression systems are commercially available in kit form from, inter alia, Thermo Fisher Scientific (Waltham, MA) and Clontech (Mountain View, CA).

Plant expression systems can also be used for transforming plant cells. Generally, such systems use virus-based vectors to transfect plant cells with heterologous genes. For a description of such systems see, e.g., Porta et al., *Mol. Biotech.* (1996) 5:209-221; and Hackland et al., *Arch. Virol.* (1994) 139:1-22.

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsulated in an infectious viral particle.

Several non-viral methods for the transfer of expression constructs into cultured mammalian cells also are contemplated by the present disclosure. These include the use of calcium phosphate precipitation, DEAE-dextran, electroporation, direct microinjection, DNA-loaded liposomes, lipofectamine-DNA complexes, cell sonication, gene bombardment using high velocity microprojectiles, and receptor-mediated transfection (see, e.g., Graham and Van Der Eb (1973) Virology 52:456-467; Chen and Okayama (1987) Mol. Cell Biol. 7:2745-2752; Rippe et al. (1990) Mol. Cell Biol. 10:689-695; Gopal (1985) Mol. Cell Biol. 5:1188-1190; Tur-Kaspa et al. (1986) Mol. Cell. Biol. 6:716-718; Potter et al. (1984) Proc. Natl. Acad. Sci. USA 81:7161-7165); Harland and Weintraub (1985) J. Cell Biol. 101: 1094-1099); Nicolau and Sene (1982) Biochim. Biophys. Acta 721:185-190; Fraley et al. (1979) Proc. Natl. Acad. Sci. USA 76:3348-3352; Fechheimer et al. (1987) Proc Natl. Acad. Sci. USA 84:8463-8467; Yang et al. (1990) Proc. Natl. Acad. Sci. USA 87:9568-9572; Wu and Wu (1987) J. Biol. Chem. 262:4429-4432; Wu and Wu (1988) Biochemistry 27:887-892; herein incorporated by reference). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the present disclosure, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (Proc. Natl. Acad. Sci. USA (1984) 81:7529-7533) successfully injected polyomavirus DNA in the form of calcium phosphate precipitates into liver and spleen of adult and newborn mice demonstrating active viral replication and acute infection. Benvenisty and Neshif (Proc. Natl. Acad. Sci. USA (1986) 83:9551-9555) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment, a naked DNA expression construct may be transferred into cells by particle bombardment. This method depends on the ability to accelerate DNA-coated microprojectiles to a high velocity allowing them to pierce cell membranes and enter cells without killing them (Klein et al. (1987) Nature 327:70-73). Several devices for accelerating small particles have been developed. One such device relies on a high voltage discharge to generate an electrical current, which in turn provides the motive force (Yang et al. (1990) Proc. Natl. Acad. Sci. USA 87:9568-9572). The microprojectiles may consist of biologically inert substances, such as tungsten or gold beads.

In a further embodiment, the expression construct may be delivered using liposomes. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat (1991) Liver Diseases, Targeted Diagnosis and Therapy Using Specific Receptors and Ligands, Wu et al. (Eds.), Marcel Dekker, NY, 87-104). Also contemplated is the use of lipofectamine-DNA complexes.

In certain embodiments of the present disclosure, the liposome may be complexed with a hemagglutinating virus (HVJ). This has been shown to facilitate fusion with the cell membrane and promote cell entry of liposome-encapsulated DNA (Kaneda et al. (1989) Science 243:375-378). In other embodiments, the liposome may be complexed or employed in conjunction with nuclear non-histone chromosomal proteins (HMG-I) (Kato et al. (1991) J. Biol. Chem. 266(6): 3361-3364). In yet further embodiments, the liposome may be complexed or employed in conjunction with both HVJ and HMG-I. In that such expression constructs have been successfully employed in transfer and expression of nucleic acid in vitro and in vivo, then they are applicable for the present disclosure. Where a bacterial promoter is employed in the DNA construct, it also will be desirable to include within the liposome an appropriate bacterial polymerase.

Other expression constructs which can be employed to deliver a nucleic acid into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu (1993) Adv. Drug Delivery Rev. 12:159-167).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) and transferrin (see, e.g., Wu and Wu (1987), supra; Wagner et al. (1990) Proc. Natl. Acad. Sci. USA 87(9):3410-3414). Recently, a synthetic neoglycoprotein, which recognizes the same receptor as ASOR, has been used as a gene delivery vehicle (Ferkol et al. (1993) FASEB J. 7:1081-1091; Perales et al. (1994) Proc. Natl. Acad. Sci. USA 91(9):4086-4090), and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (Methods Enzymol. (1987) 149:157-176) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell by any number of receptor-ligand systems with or without liposomes. Also, antibodies to surface antigens on cells can similarly be used as targeting moieties.

In a particular example, a recombinant polynucleotide encoding a gRNA-donor polynucleotide cassette or RNA-guided nuclease may be administered in combination with a cationic lipid. Examples of cationic lipids include, but are not limited to, lipofectin, DOTMA, DOPE, and DOTAP. The publication of WO/0071096, which is specifically incorporated by reference, describes different formulations, such as a DOTAP:cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects.

In certain embodiments, gene transfer may more easily be performed under ex vivo conditions. Ex vivo gene therapy refers to the isolation of cells from a subject, the delivery of a nucleic acid into cells in vitro, and then the return of the modified cells back into the subject. This may involve the collection of a biological sample comprising cells from the subject. For example, blood can be obtained by venipuncture, and solid tissue samples can be obtained by surgical techniques according to methods well known in the art.

Usually, but not always, the subject who receives the cells (i.e., the recipient) is also the subject from whom the cells are harvested or obtained, which provides the advantage that the donated cells are autologous. However, cells can be obtained from another subject (i.e., donor), a culture of cells from a donor, or from established cell culture lines. Cells may be obtained from the same or a different species than the subject to be treated, but preferably are of the same species, and more preferably of the same immunological profile as the subject. Such cells can be obtained, for example, from a biological sample comprising cells from a close relative or matched donor, then transfected with nucleic acids (e.g., encoding a donor polynucleotide, gRNA, or RNA-guided nuclease), and administered to a subject in need of genome modification, for example, for treatment of a disease or condition.

C. Sequencing of Barcoded gRNA-Donor Polynucleotide Cassettes

Any high-throughput technique for sequencing can be used in the practice of the present disclosure. DNA sequencing techniques include dideoxy sequencing reactions (Sanger method) using labeled terminators or primers and gel separation in slab or capillary, sequencing by synthesis using reversibly terminated labeled nucleotides, pyrosequencing, 454 sequencing, sequencing by synthesis using allele specific hybridization to a library of labeled clones followed by ligation, real time monitoring of the incorporation of labeled nucleotides during a polymerization step, polony sequencing, SOLID sequencing, and the like.

Certain high-throughput methods of sequencing comprise a step in which individual molecules are spatially isolated on a solid surface where they are sequenced in parallel. Such solid surfaces may include nonporous surfaces (such as in Solexa sequencing, e.g. Bentley et al, Nature, 456: 53-59 (2008) or Complete Genomics sequencing, e.g. Drmanac et al, Science, 327: 78-81 (2010)), arrays of wells, which may include bead- or particle-bound templates (such as with 454, e.g. Margulies et al, Nature, 437: 376-380 (2005) or Ion Torrent sequencing, U.S. patent publication 2010/0137143 or 2010/0304982), micromachined membranes (such as with SMRT sequencing, e.g. Eid et al, Science, 323: 133-138 (2009)), or bead arrays (as with SOLiD sequencing or polony sequencing, e.g. Kim et al, Science, 316: 1481-1414 (2007)). Such methods may comprise amplifying the isolated molecules either before or after they are spatially isolated on a solid surface. Prior amplification may comprise emulsion-based amplification, such as emulsion PCR, or rolling circle amplification.

Of particular interest is sequencing on the Illumina MiSeq, NextSeq, and HiSeq platforms, which use reversible-terminator sequencing by synthesis technology (see, e.g., Shen et al. (2012) BMC Bioinformatics 13:160; Junemann et al. (2013) Nat. Biotechnol. 31(4):294-296; Glenn (2011) Mol. Ecol. Resour. 11(5):759-769; Thudi et al. (2012) Brief Funct. Genomics 11(1):3-11; herein incorporated by reference).

These sequencing approaches can thus be used to sequence the barcoded gRNA-donor polynucleotide cassettes to associate their sequences with adjacent (shorter) barcodes, and to identify their corresponding colonies in an ordered array. Short DNA barcodes can also be used in multiplex sequencing of ordered array samples. Accordingly, a clone comprising any desired gRNA-donor polynucleotide cassette can then be picked out of an ordered array of cells (e.g., with an automated robotic device or manually).

D. Kits

The above-described reagents including recombinant polynucleotides encoding gRNA-donor polynucleotide cassettes, RNA-guided nucleases, barcoder cells, media suitable for growing cells, and site-specific recombinase systems can be provided in kits, with suitable instructions and other necessary reagents for genome modification and barcoding as described herein. The kit may also contain cells for genome modification, agents for positive and negative selection of cells, and transfection agents. The kit will normally contain in separate containers the gRNA-donor polynucleotide cassettes, RNA-guided nucleases, barcoder cells, media suitable for growing cells, and site-specific recombinase systems, and other reagents that are required. Instructions (e.g., written, CD-ROM, DVD, Blu-ray, flash drive, digital download, etc.) for carrying out genome editing and barcoding as described herein usually will be included in the kit. The kit can also contain, depending on the particular assay used, other packaged reagents and materials (i.e., wash buffers, and the like). Genome editing and barcoding such as described herein, can be conducted using these kits.

E. Applications

The genome editing and barcoding methods of the present disclosure will find numerous applications in basic research and development and regenerative medicine. The methods can be used to introduce a mutation (e.g., insertion, deletion, or substitution) into any gene in the genomic DNA of a cell. For example, the methods described herein can be used for inactivation of a gene in a cell to determine the effects of a gene knockout or to study the effects of a known disease-causing mutation. Such genetically modified cells may be useful as disease models for drug screening. Alternatively, the methods described herein can be used for removal of a mutation, such as a disease-causing mutation, from a gene in the genomic DNA of a cell. In particular, genome editing as described herein can be used for developing cell lines with desired characteristics, such as adding reporter genes to cells at desired sites, or improving efficacy, controllability safety, and/or survival.

In particular, the methods of the present disclosure are useful for creating arrayed strain collections with known genetic modifications for various purposes, including, but not limited to, protein engineering, DNA variant production, strain engineering, metabolic engineering, or drug screening. Strains with mutations can be ordered in an array according to their known gRNA and donor polynucleotide sequences with positioning dependent, for example, on the targeted chromosomal locus or gene that was modified. In addition, strains can be phenotyped to determine the effects of particular mutations. Arrayed strains can be grown on media plates or in liquid cultures. For example, strains can be parsed into an array comprising media plates or separate tubes containing media. Subsequently, any colony or combination of colonies with genetic modifications of interest from the arrayed strains can be selected to inoculate a liquid culture and grown in bulk. Subsequent rounds of genome modification may be performed to optimize a desired property, such as increasing biomass, improving growth under different conditions, or optimizing metabolic production of different compounds.

In certain embodiments, the methods described herein are used to create an arrayed collection of genetically modified yeast strains. Such arrayed collections of yeast strains can be used, for example, in optimizing production of bread, beer, wine, biofuel, animal-free production of antibodies, enzymes, and other proteins, and other yeast-based technology. Genetically modified yeast strains will also find use in drug screening, metabolic production of compounds, vaccine production, pathogen detection, and production of DNA and protein variants.

III. EXPERIMENTAL

Below are examples of specific embodiments for carrying out the present disclosure. The examples are offered for illustrative purposes only, and are not intended to limit the scope of the present disclosure in any way.

Efforts have been made to ensure accuracy with respect to numbers used (e.g., amounts, temperatures, etc.), but some experimental error and deviation should, of course, be allowed for.

Example 1

Scarless Genome Editing Through Two-Step Homology Directed Repair

Introduction

We have previously described a cost-effective method called Recombinase Directed Indexing (REDI), which involves integration of a complex library into yeast, site-specific recombination to index library DNA, and next-generation sequencing to identify desired clones. REDI was initially developed to produce high-quality DNA libraries, circumventing the high synthesis error rates, uneven representation, and lack of access to individual oligonucleotides associated with array-synthesized oligonucleotides. It was also used to rapidly create a CRISPRi collection for transcriptional repression of the essential yeast open reading frames (ORFs).

Here we extend this technology for massively parallel production of genetically engineered clones. Our method involves large-scale highly-efficient genome editing with a plasmid system that facilitates integration of the gRNA and donor sequence as a genomic barcode, allowing identification, isolation, and massively-parallel validation of individual variants from a pool of transformants. Importantly, we also outline key strategies to enhance HR in metazoan cells, including CRISPR-interference (CRISPRi), RNA interference (RNAi), or chemical-based inhibition of NHEJ in combination with active donor recruitment.

Results

We have previously described an inexpensive, high-throughput, yeast-based method for parsing verified sequences from complex mixtures, which we call Recombinase Directed Indexing, or REDI[7]. Building on the REDI system, we now describe a dual editing-barcoding system that involves CRISPR/Cas9-mediated editing of a target genomic locus with high-copy plasmid-borne donor DNA, followed by SceI-mediated capture of the guide-donor cassette into the REDI locus. The integrating gRNA and donor DNA sequences act as a barcode that enables both (1) strain isolation via REDI and (2) robust phenotyping following competitive growth. The high copy (2-micron) nature of the guide-donor plasmid enables efficient repair. Integration of the guide RNA-donor DNA cassette into the REDI locus results in precisely one barcode molecule per cell, thereby circumventing noise that could arise from copy number variation and plasmid loss which are characteristic of vector-based barcodes and which confound phenotyping accuracy.

To permit parallel production of many genetically engineered variants, we used gRNA/donor DNA pairs synthesized on the same oligonucleotide molecule. Therefore, an internal cloning step was used to maintain oligo lengths below the limits of array-based synthesis, and avoid the inclusion of DNA synthesis errors in the constant part of the guide RNA sequence (FIG. S1). The internal cloning step inserts this DNA as a sequence-perfect insert (see FIG. 9, Methods).

Figure 2A:
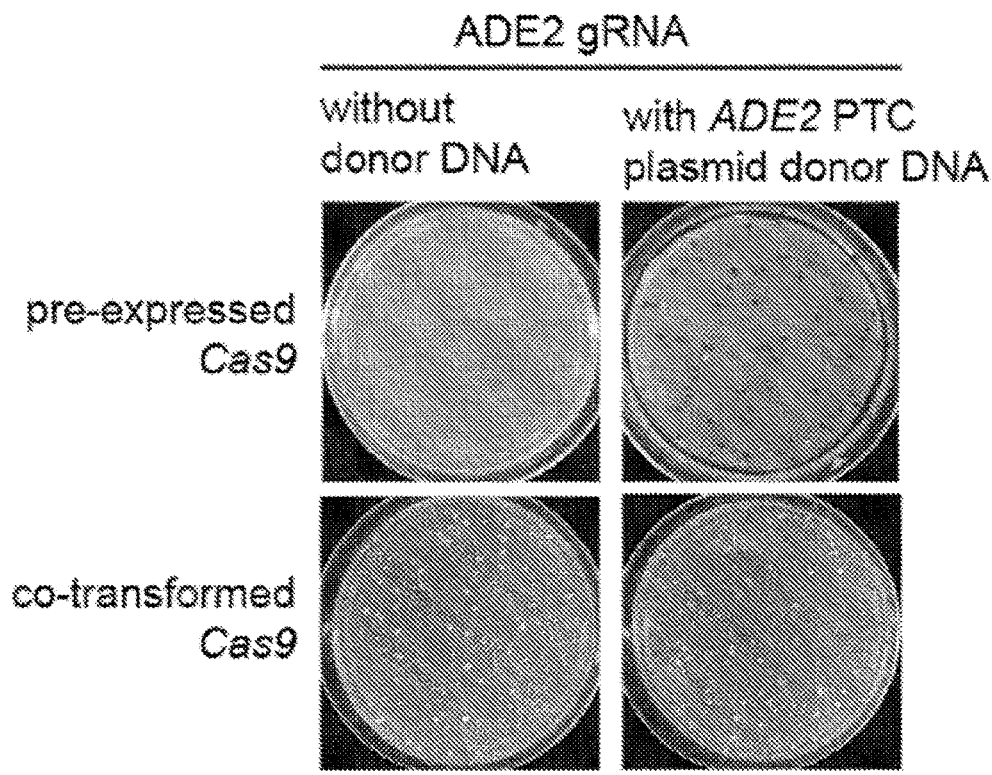

Effective isolation of edited clones following transformation with libraries encoding thousands to millions of genome modifications requires a system with optimal editing efficiencies. Therefore, numerous parameters of the CRISPR/Cas9 editing system in yeast, including promoters for Cas9 and guide RNA expression, were systematically assessed. A tRNA-HDV promoter for guide RNA expression was found to produce optimal editing efficiency. We also examined the importance of Cas9 expression level, as this parameter was found to be important in previous studies in yeast using linear donor DNA[13]. We created a construct targeting the yeast ADE2 locus, which produces yeast with a characteristic red color when mutated. Donor DNA was designed to incorporate a frame-shift mutation in the ADE2 locus and be resistant to recognition by its partner guide RNA (see Methods). This construct was co-transformed into yeast with a Cas9-expressing construct, or transformed into yeast pre-expressing Cas9. When transformed into yeast pre-expressing Cas9, nearly all clones incorporated the desired change encoded by the donor DNA, as illustrated by the dominance of red colonies (FIG. 2A, top right). Sequencing at the ADE2 locus further verified the desired change had been incorporated in six independent clones (FIG. 2B). Importantly, these experiments revealed that cell death occurs in the absence of donor DNA, rather than survival through the error-prone NHEJ pathway that predominates in most other systems (FIG. 2A, top left). Thus, the expression of Cas9 under a strong, constitutive promoter results in a strict dependence of cell survival on the plasmid-borne donor DNA, and the only clones surviving the transformation faithfully incorporated the donor DNA-directed changes.

We have demonstrated that transforming plasmids harboring Cas9 into cells pre-expressing guide RNA results in similarly high-levels of editing efficiency and survival rate. The enhanced survival may be due to providing guide-donor plasmids enough time to accumulate in high copy numbers, resulting in enhanced repair of DNA breaks. In addition, we tested an inducible promoter (Gal1 promoter) for Cas9 and found it to provide equally efficient editing.

Figure 2C:
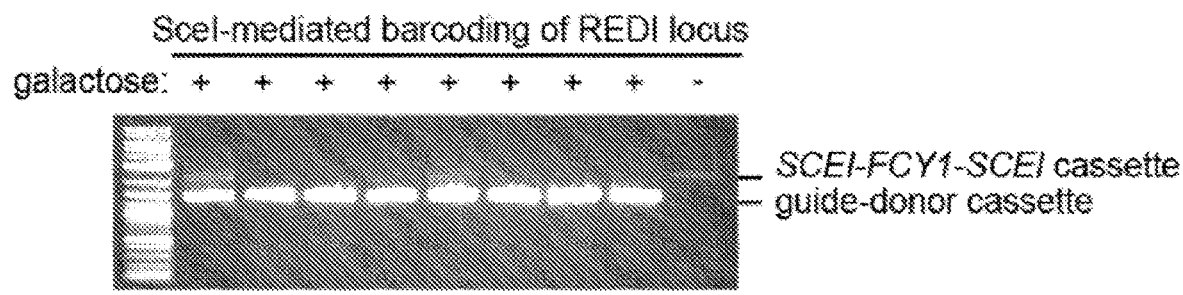

We next sought to demonstrate that genomic barcode integration at the REDI locus can be readily achieved after target editing. This was achieved in two different ways. ADE2-edited cells were shifted to galactose medium to induce expression of SceI and cutting of SceI sites flanking the FCY1 counter-selectable marker at the REDI locus. This method of high throughput genome integration is an extension of the method we previously described for integration of transforming oligonucleotides[17]. The guide RNA-donor DNA cassette from the plasmid was efficiently incorporated in all clones tested (FIG. 2C). Alternatively, we have used a gRNA that targets the SceI sites or the counter-selectable FCY1 gene and used CRISPR cutting at the same time as CRISPR was used to edit the genome to integrate the editing cassette into the REDI locus. Thus, mating of these clones to REDI barcoder strains followed by paired-end Illumina sequencing could be used to identify and isolate these clones from a highly complex pool of variants.

Figure 3:
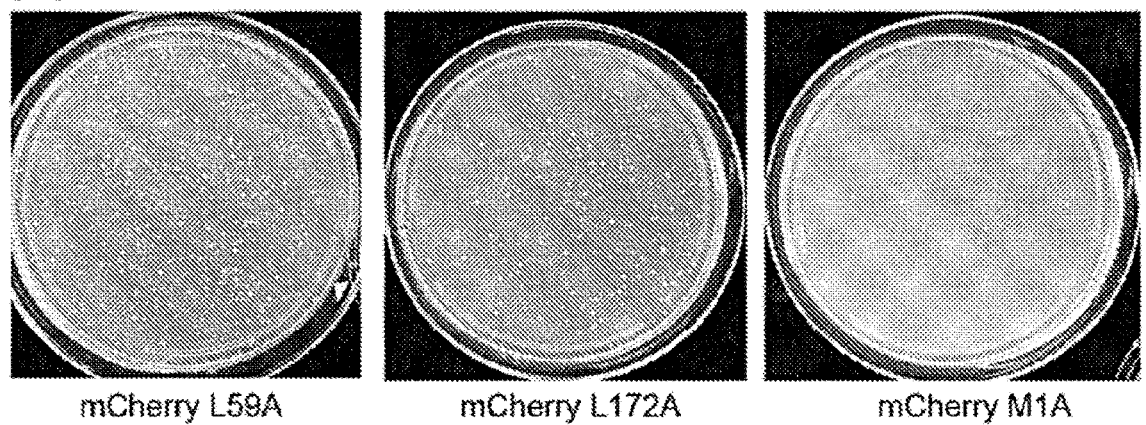
FIG. 3 shows selected guide-donor plasmids for editing a heterologous ORF (mCherry). A library of guide-donor oligonucleotides was purchased from Agilent Technologies, and cloned into the high-copy guide expression vector (FIG. 1). A few bacterial clones were sequenced for correct incorporation of the guide-donor insert, and subsequently transformed into yeast cells harboring pre-expressed Cas9 and the mCherry ORF. Shown are the transformation plates after 2 days of growth.
Figure 3:
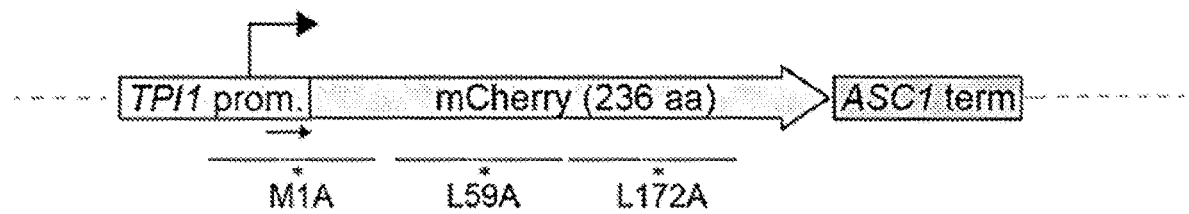
Figure 4A:
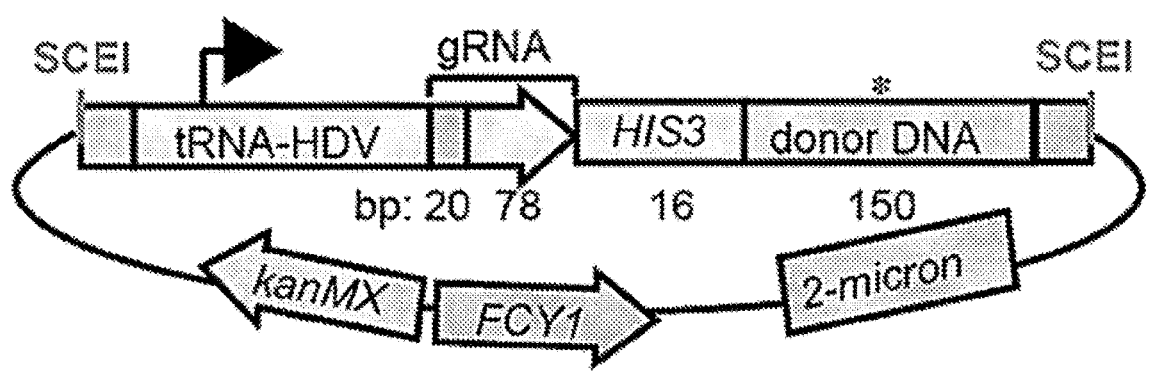
FIGS. 4A-4F show that active donor recruitment enables high frequencies of donor directed repair.
Figure 4A:
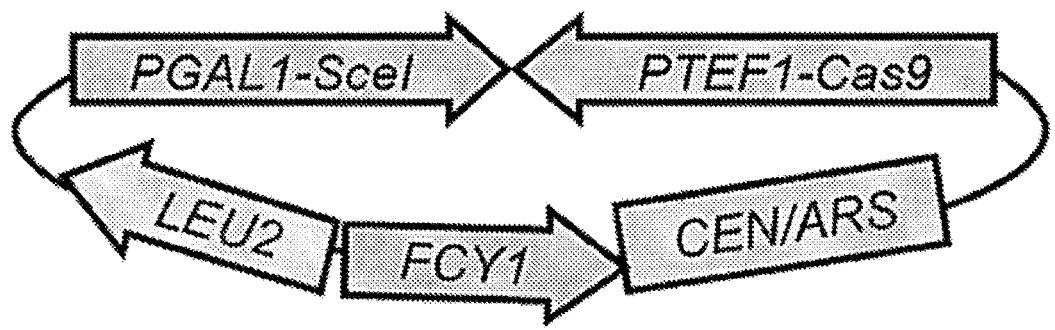
Figure 4B:
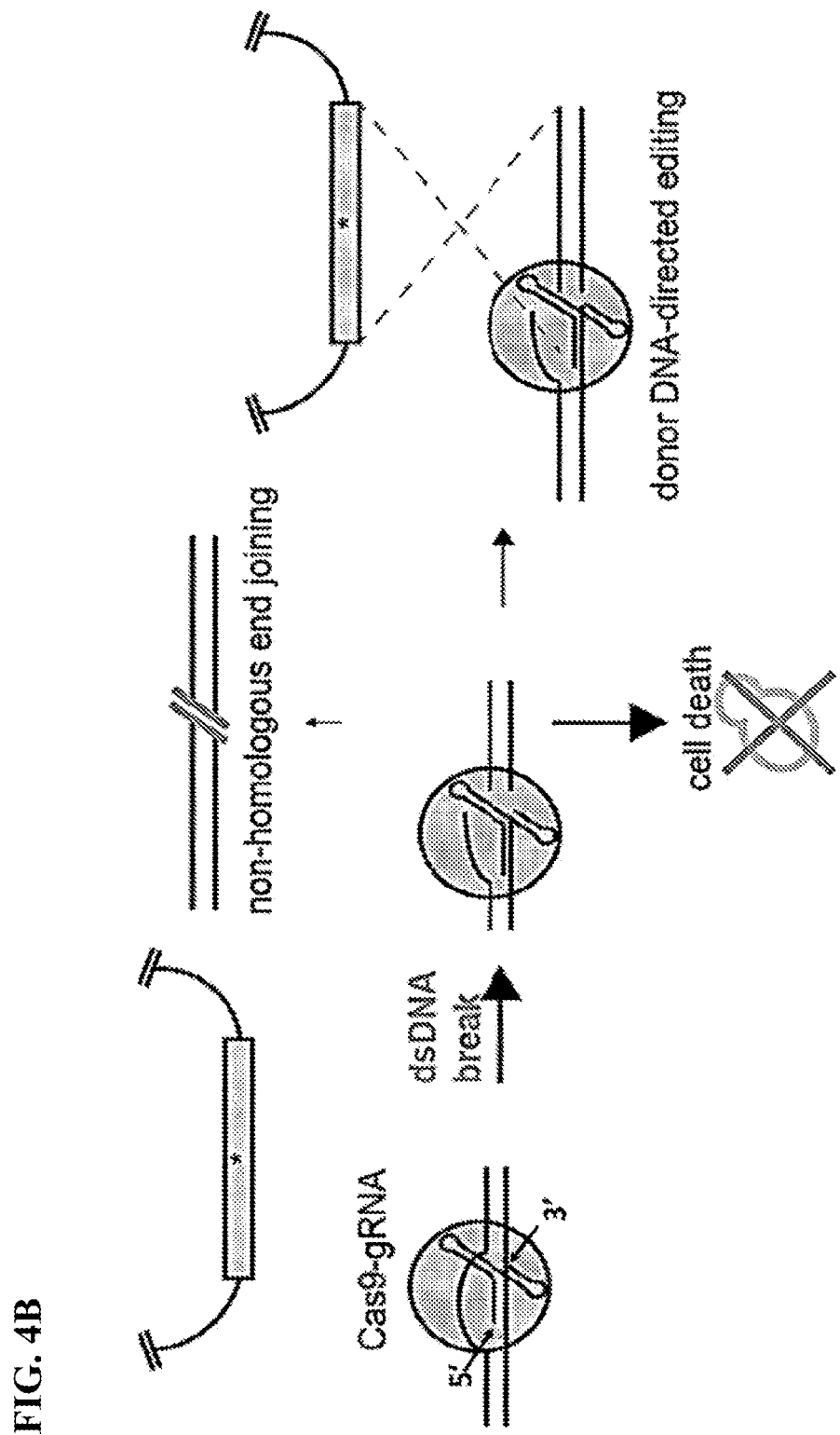
Figure 4C:
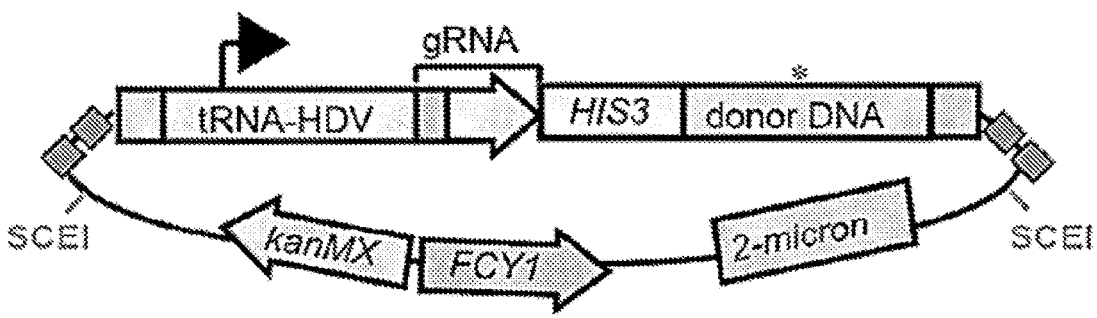
Figure 4C:
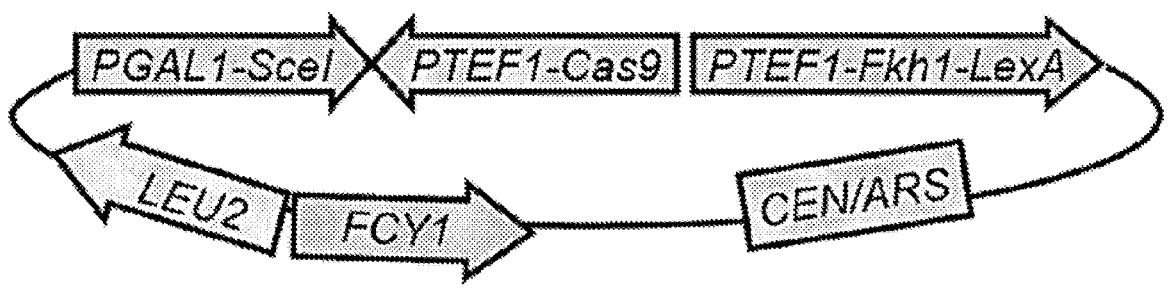
Figure 4D:
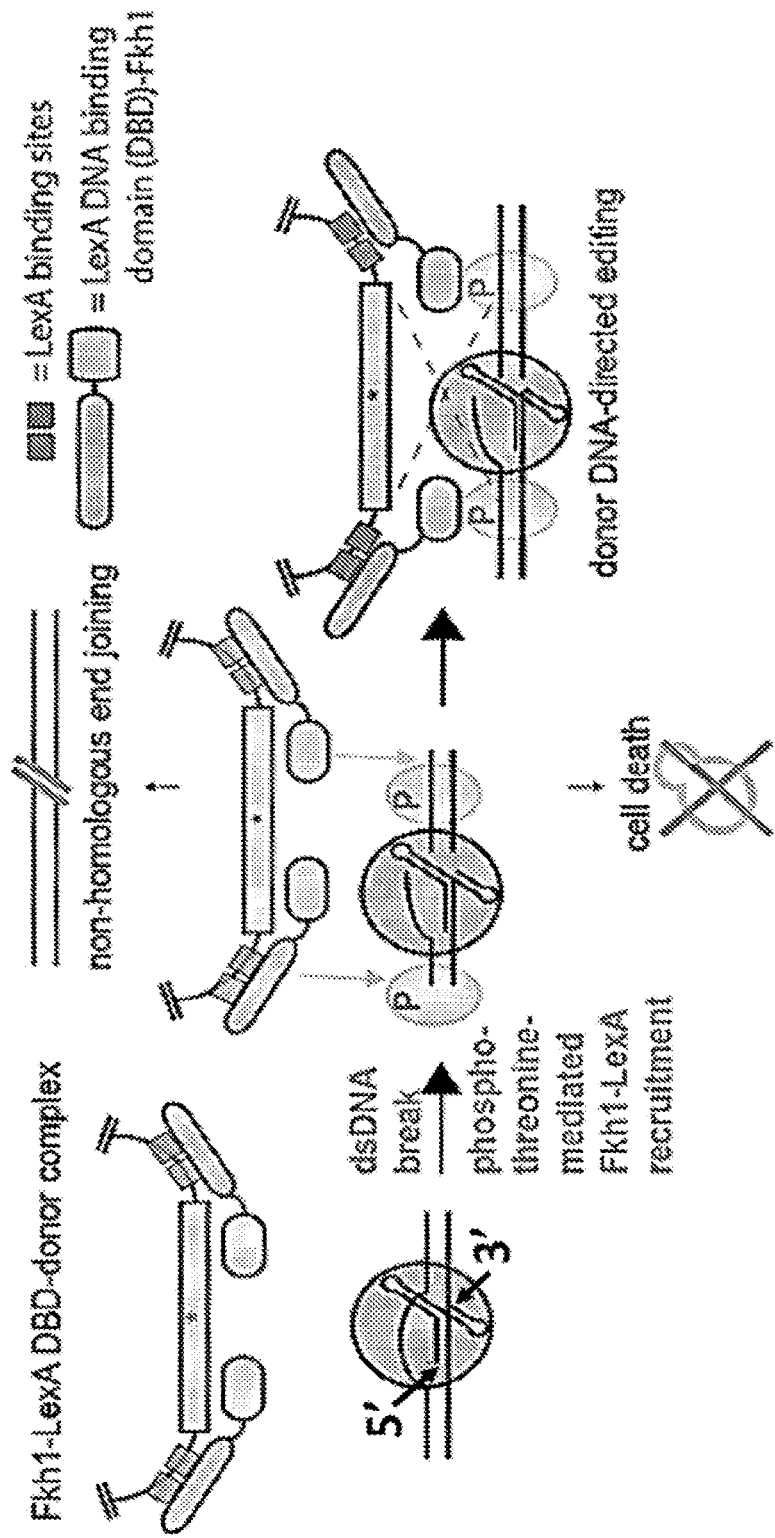
Figure 4E:
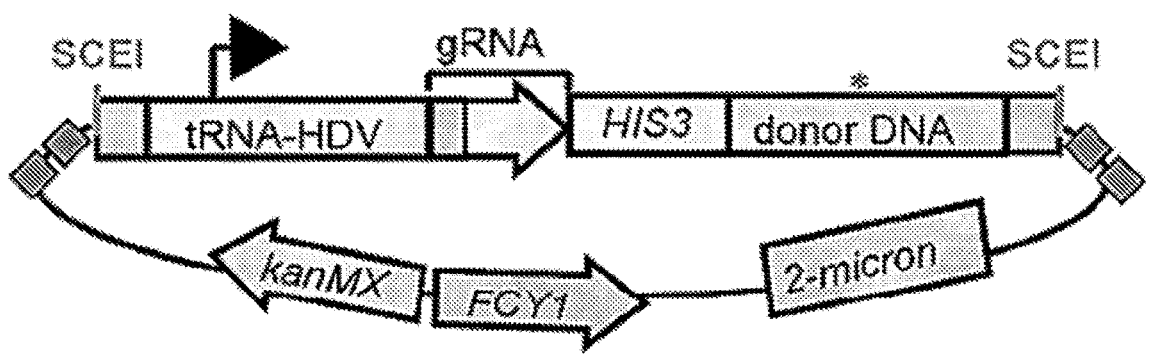
Figure 4E:
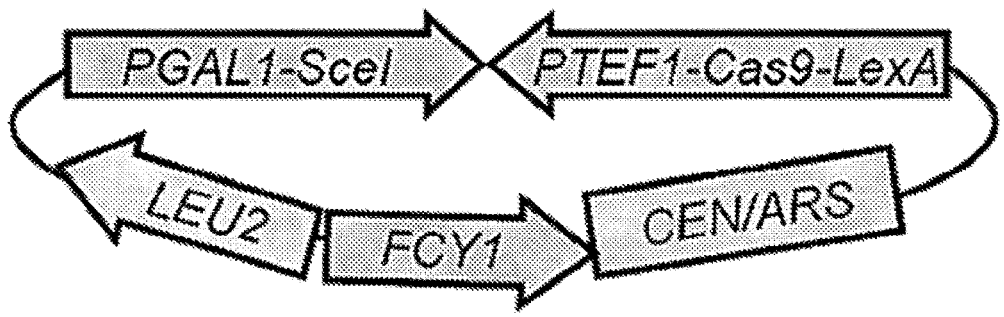
Figure 4F:
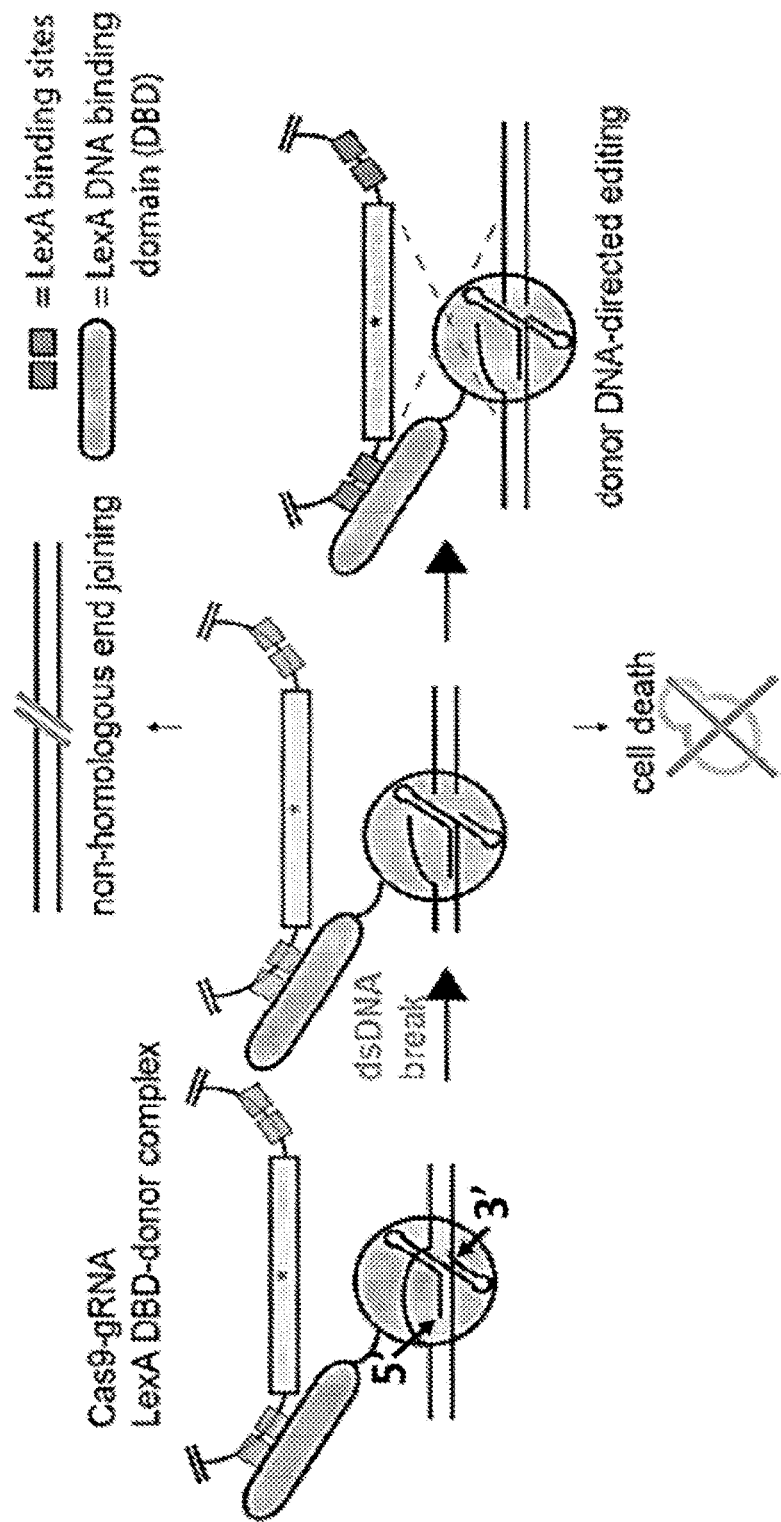
Figure 10A:
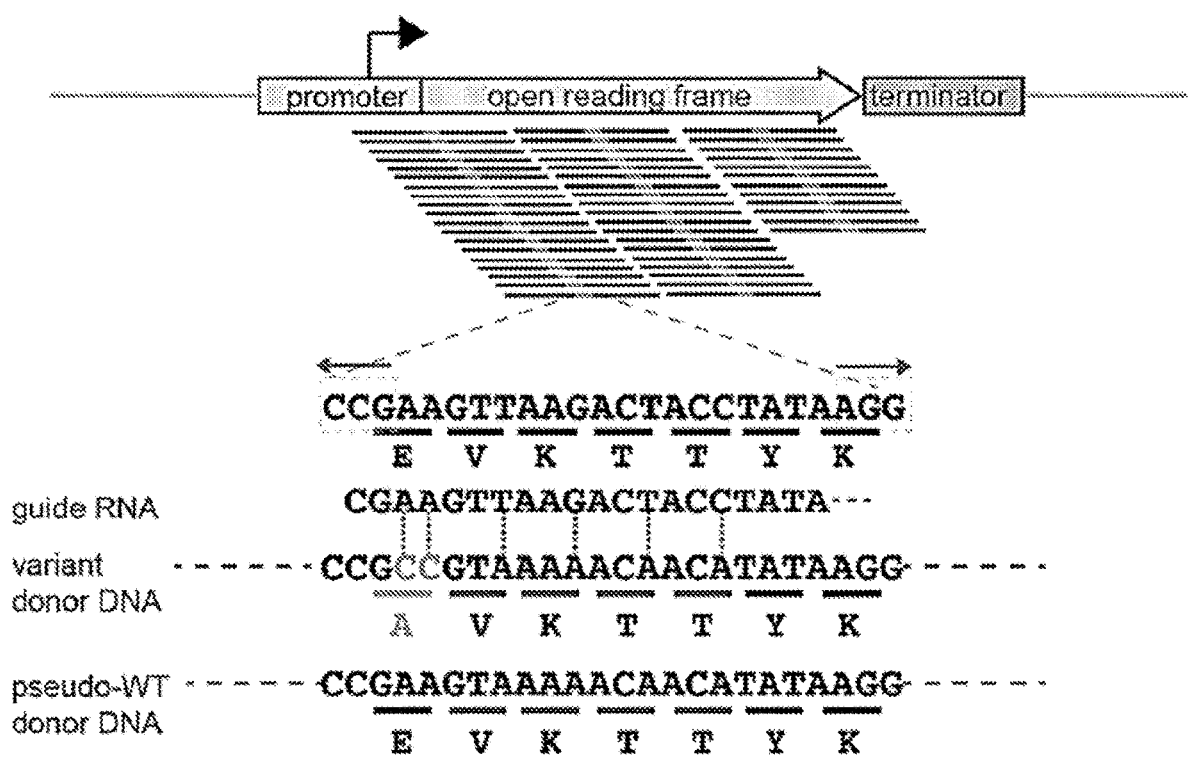

To establish the scalability of our method, we designed and ordered (Agilent Technologies) a library of gRNA-donor DNAs to saturate a heterologous ORF (mCherry) with single amino acid mutations. To enable complete saturation of the ORF and ensure that the cells incorporated the intended changes, we devised a novel synonymous codon spreading strategy to enable editing at sites outside of guide recognition regions (FIG. 10). We selected a few guide-donors isolated from the pool to verify their functionality. Unexpectedly, one of the guide-donor plasmids resulted in high toxicity and low survival (FIG. 3, right panel). This guide RNA targeted the initiating methionine codon (ATG) and adjacent TPI1 promoter sequence. The same guide RNA target sequence is also present at the native yeast TPI1 gene. Thus, it is expected that the construct will induce double strand breaks at two locations in the yeast genome. While containing homology to the TPI1 promoter, the donor DNA lacked any homology to the beginning of the TPI1 ORF, suggesting that repair of target cut sites requires sufficient homology on both sides of the dsDNA break. Together with our data demonstrating the toxicity of pre-expressed Cas9 and gRNA in the absence of donor DNA (FIG. 2A), this result suggests that gRNAs with strong off-target effects are likely to cause cell death after transformation if there is no donor DNA to repair these breaks. Importantly, we expect that these guide-donor sequences will not be captured by our REDI isolation protocol, and therefore will not lead to false positives or negatives. This indicates that the editing system we have described has extremely high fidelity, underscoring its utility for exploring the genome-wide impact of natural and artificial variants.

We noticed that relative to plasmids containing non-functional guide RNAs, transforming cells with plasmids having functional gRNAs and pre-expressing Cas9 led to significantly fewer (~10-fold) colonies, suggesting that ~90% of cells transformed with the guide-donor are unable to complete homologous repair despite the presence of the donor on the plasmid in the nucleus. We reasoned that Rad51-mediated homology searching for the donor DNA might be rate limiting for cell survival in our system.

To test this hypothesis, we developed a system for actively recruiting the donor to the site of the dsDNA break (FIG. 4). We noticed that less than ~0.01% of transformants survived the Cas9-gRNA expression in the absence of donor DNA, and less than ~10% survived in the presence of donor DNA. All survivors incorporated the sequence change specified by the donor DNA, indicating that the vast majority of survivors utilized homologous recombination to repair the dsDNA break. Furthermore, the presence of non-functional gRNA sequences in a pooled editing experiment resulted in significant bottleneck for the edited cells, and enrichment of the pool for gRNAs that did not yield any genome modification. This is an important issue to address because typical array synthesis errors of 1 in 200 are expected to result in ~10% of the 20-mer guide sequences containing at least one error $[(1-1/200)^{20} \sim 0.1]$.

Figure 5A:
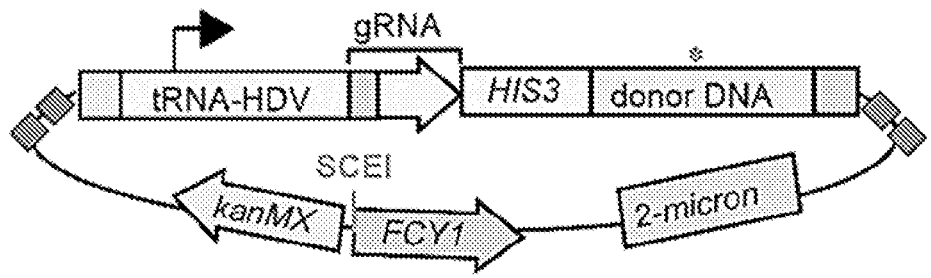
FIGS. 5A and 5B show that active donor recruitment enables high frequencies of donor directed repair.

To increase the fraction of cells surviving the editing process and reduce bottleneck effects, we implemented a system for active donor recruitment, reasoning that random diffusion of donor DNA to the cut site is rate-limiting for homologous repair. We co-expressed a LexA DNA Binding Domain (DBD) fused to Fkh1 (Fkh1 binds HML recombination enhancer, regulates donor preference during mating-type switching by recruiting DNA with Fkh1 bound to be the donor DNA [*Saccharomyces* Genome Database, Li et al. (2012) PLoS Genet. 8(4):e1002630) with Cas9, and transformed guide-donor plasmids containing LexA binding sites (FIG. 4). We also designed a system for direct fusion of LexA to Cas9 to ensure the presence of donor concurrent with dsDNA cleavage. This resulted in a dramatic increase in the survival rate and efficiency of homologous recombination-directed precision editing (FIG. 5A). We are currently testing a Cas9-LexA DBD fusion that we expect to yield a similar increase in editing efficiency, and should be generally applicable to all model systems in which RGNs can be introduced.

Figure 5B:
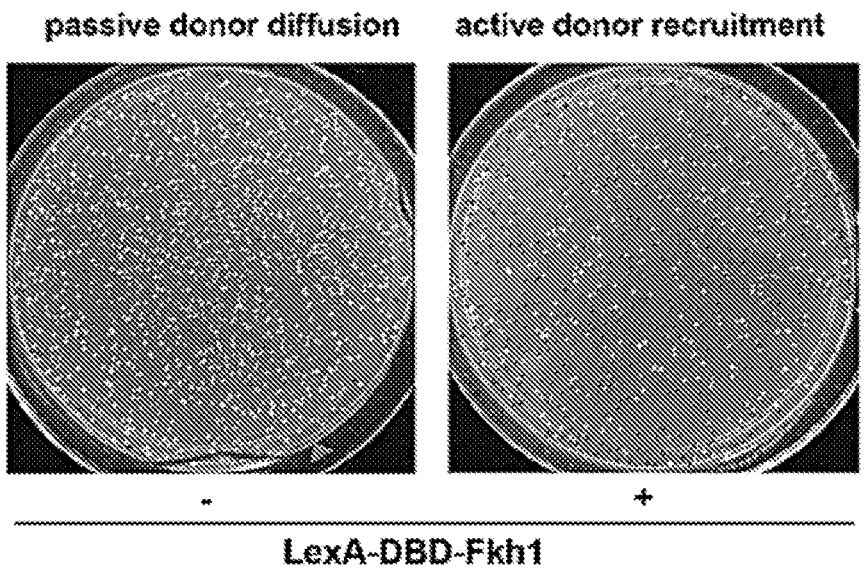

Multiple cell generations are required for 2-micron plasmids to accumulate to their highest levels within the nucleus. Therefore, we tested whether pre-expressed guide-donor would have the same effect as pre-expressed Cas9 when the opposite plasmid was transformed. Under identical transformation conditions, we were surprised to find that transforming Cas9 plasmid into cells harboring guide-donors led to significantly higher number of edited colonies, with similar or superior editing efficiency (FIG. 5B). Using an inducible Cas9 lead to a similar improved outcome. Additionally, we learned if we included a cleavage site on the guide-donor plasmid in addition to in the genome we dramatically improved editing efficiency to the point where we had very high survival with editing at both the Ade2 locus and the REDI locus concurrently.

Figure 11:
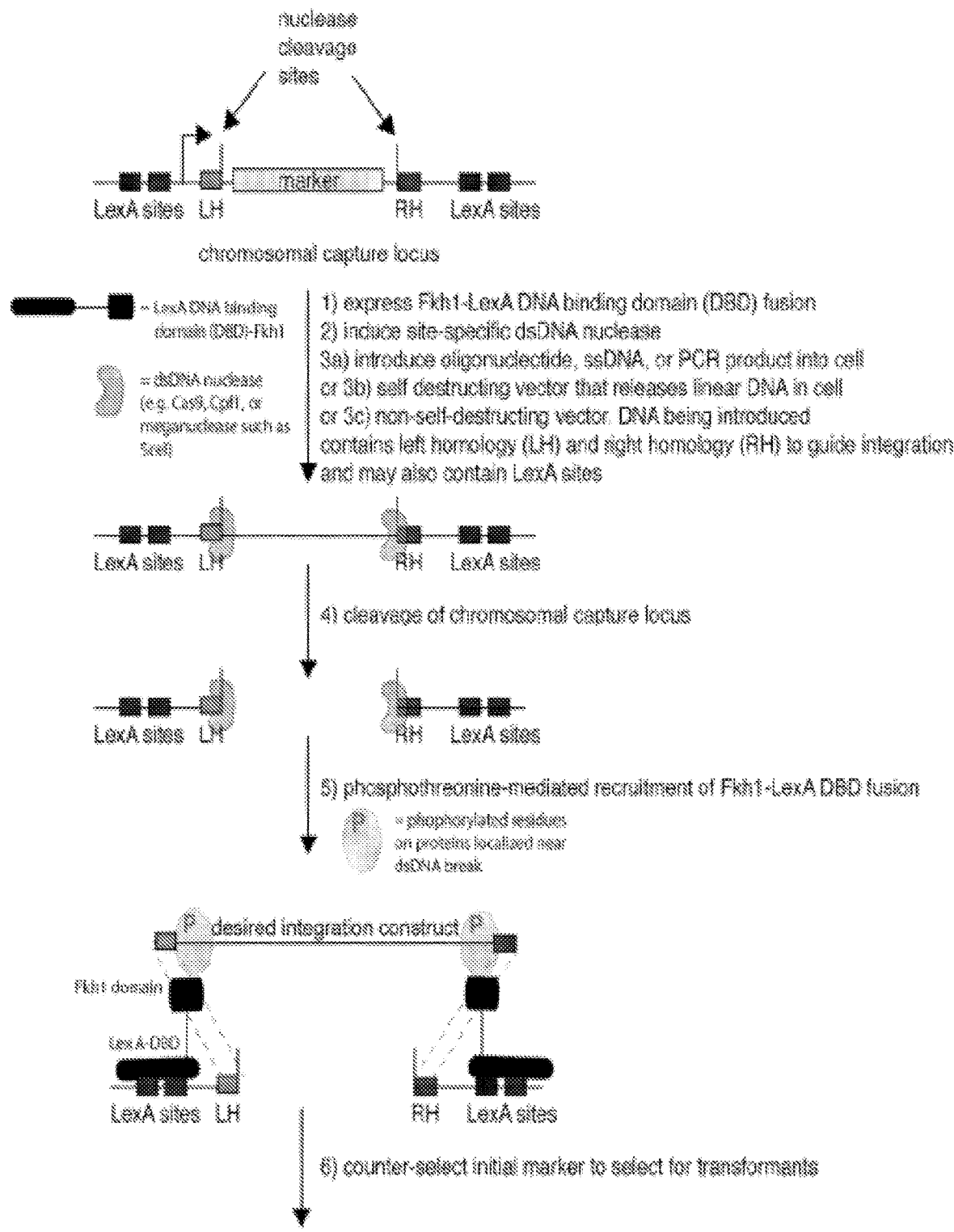
FIG. 11 shows repair directly with a genome integrated editing cassette.
Figure 11:
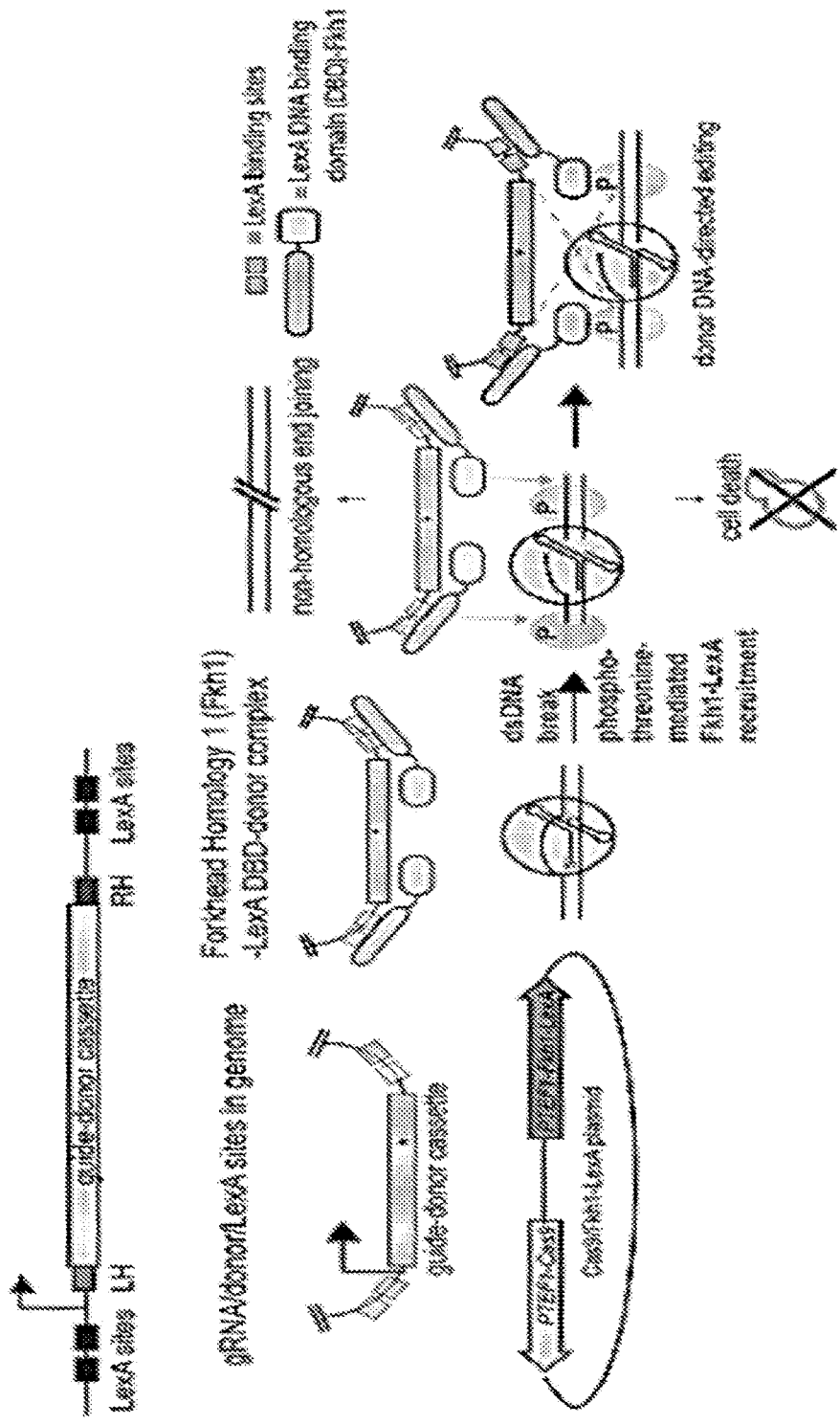

Finally, we are currently testing repair directly of genome integrated cassettes using the SceI meganuclease to cut a chromosomal barcode locus with a counterselecteable marker flanked by SceI sites, which is inside a region containing a promoter and terminator for the expression of the guide RNA which is then flanked by LexA-Fkh1 binding sites (FIG. 11). We suspect that this may lead to a similar level of editing efficiency and allow for direct genome integration from an amplified oligonucleotide library followed by induction of expression of Cas9. It further holds the advantage that this would guarantee only one edit per cell.

Figure 6A:
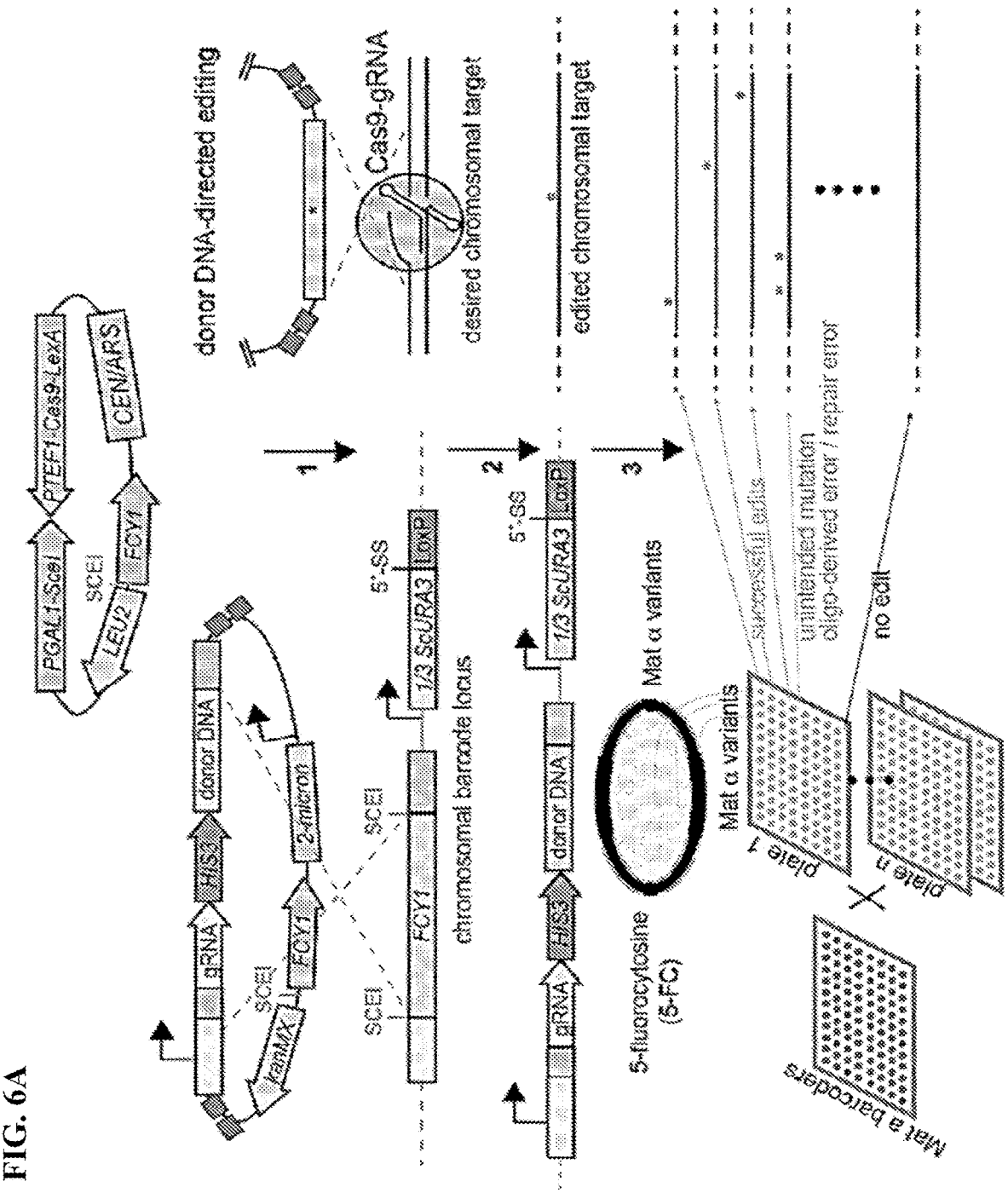
FIGS. 6A and 6B show a dual editing and barcoding system combined with Recombinase Directed Indexing (REDI).
Figure 6B:
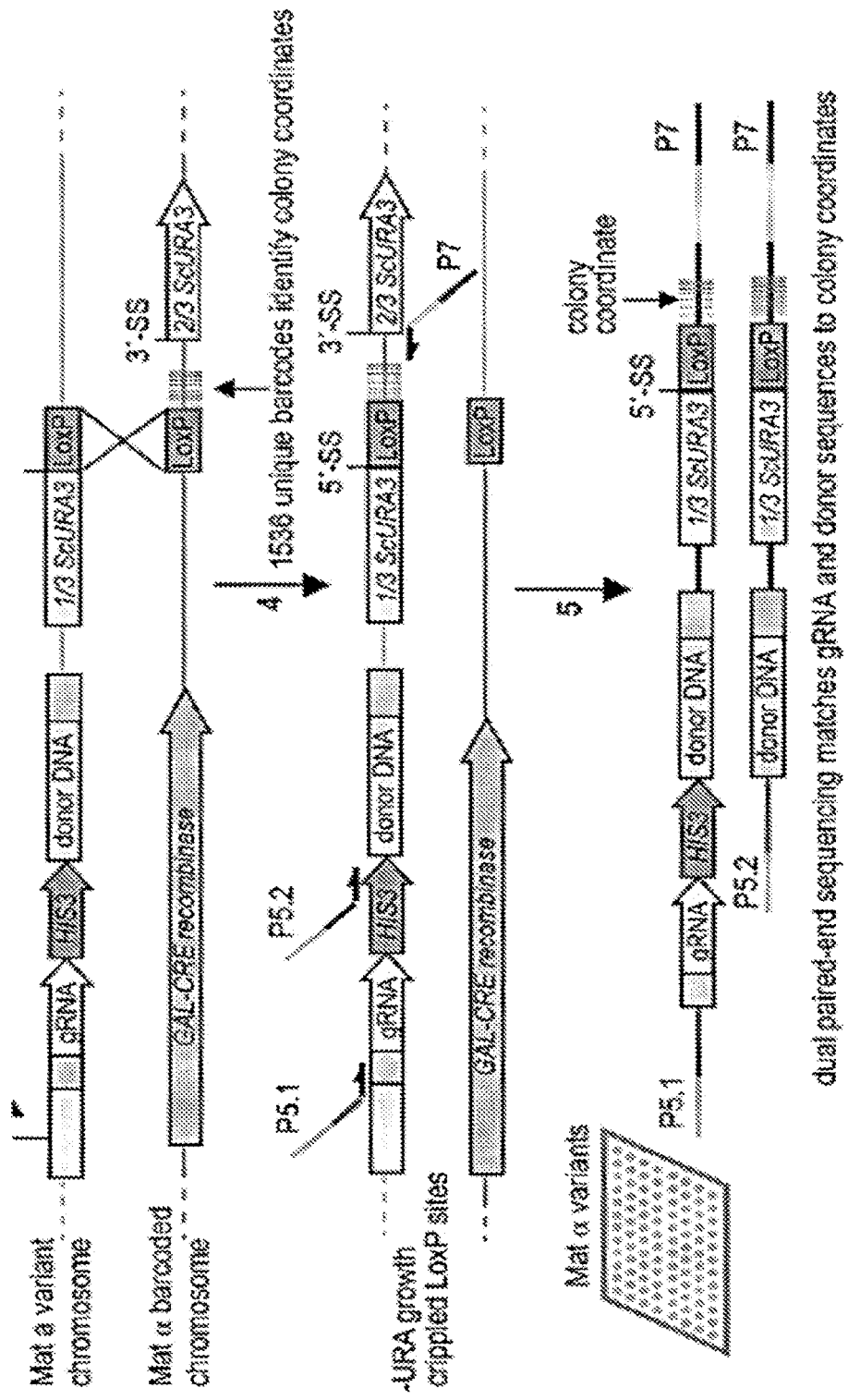
Figure 7A:
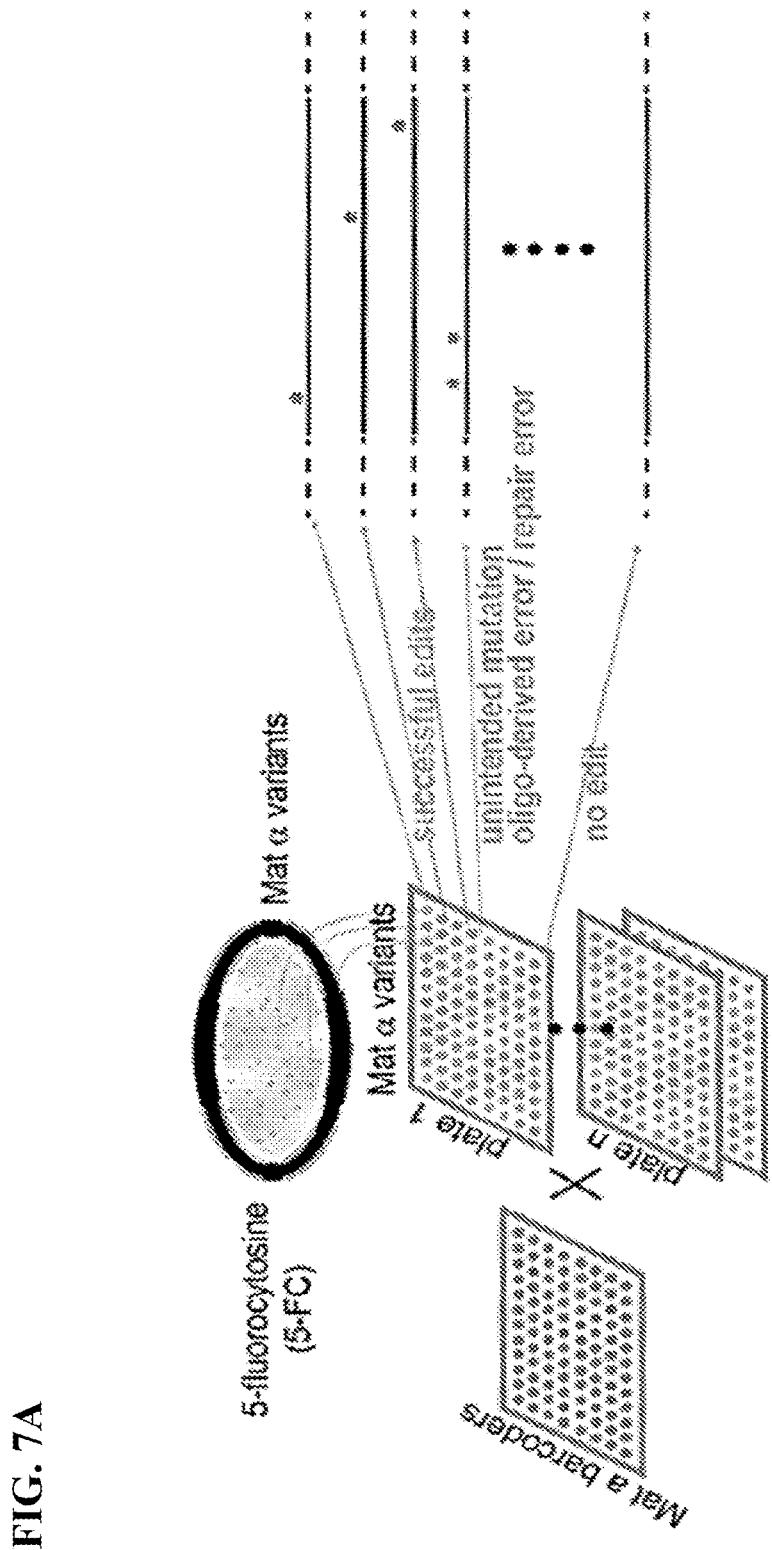
FIGS. 7A-7C show REDI-mediated massively parallel strain validation.
Figure 7B:
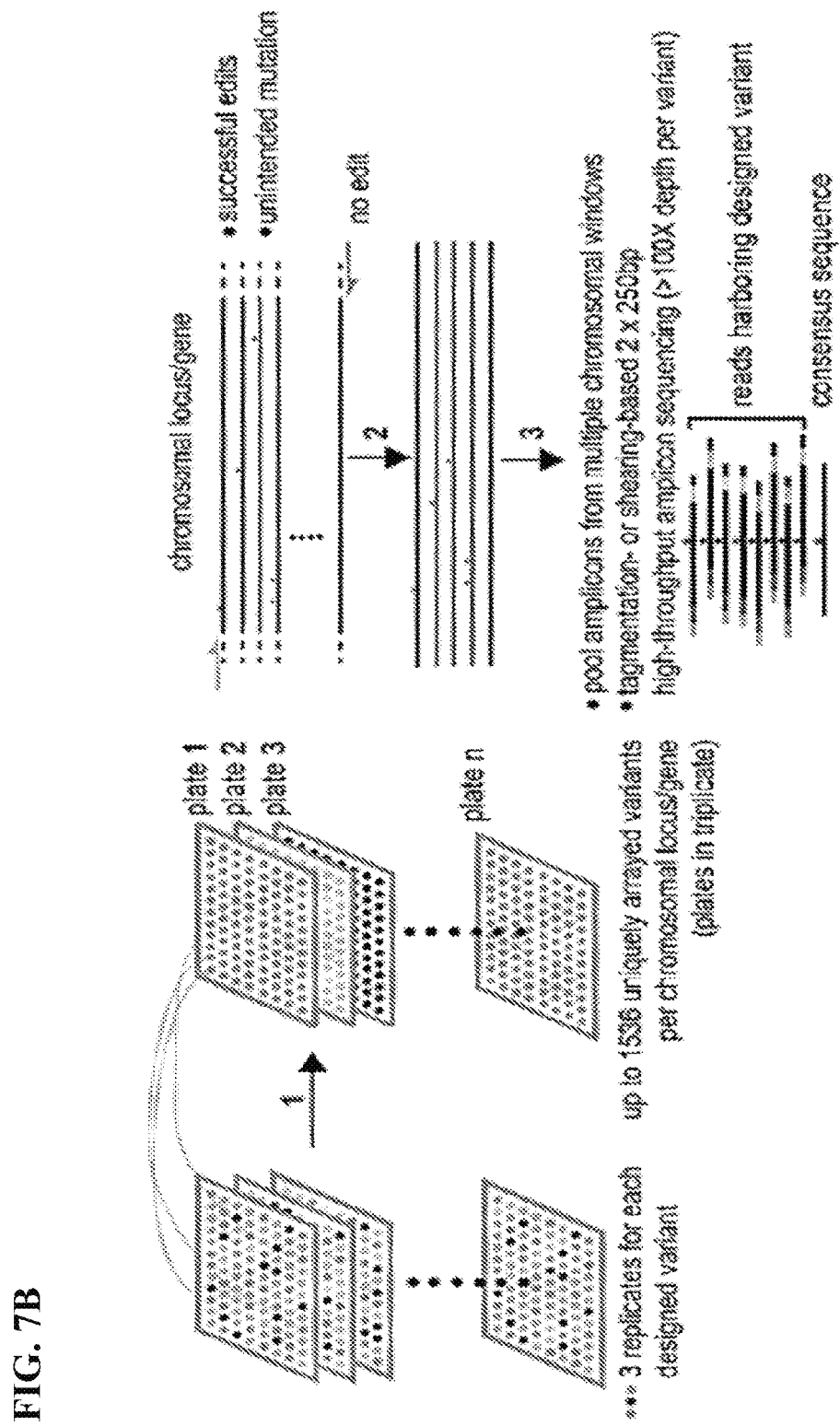
Figure 7C:
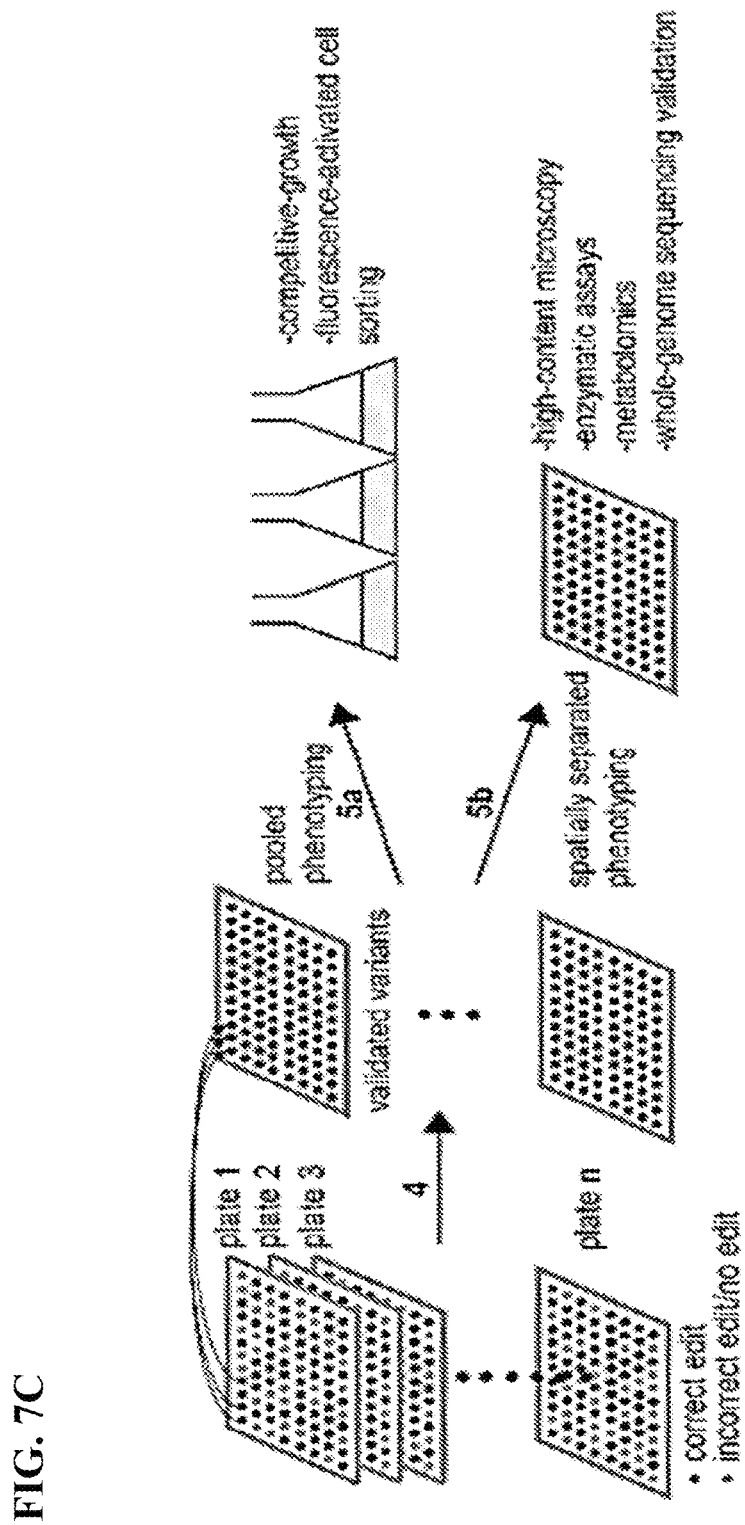
Figure 8:
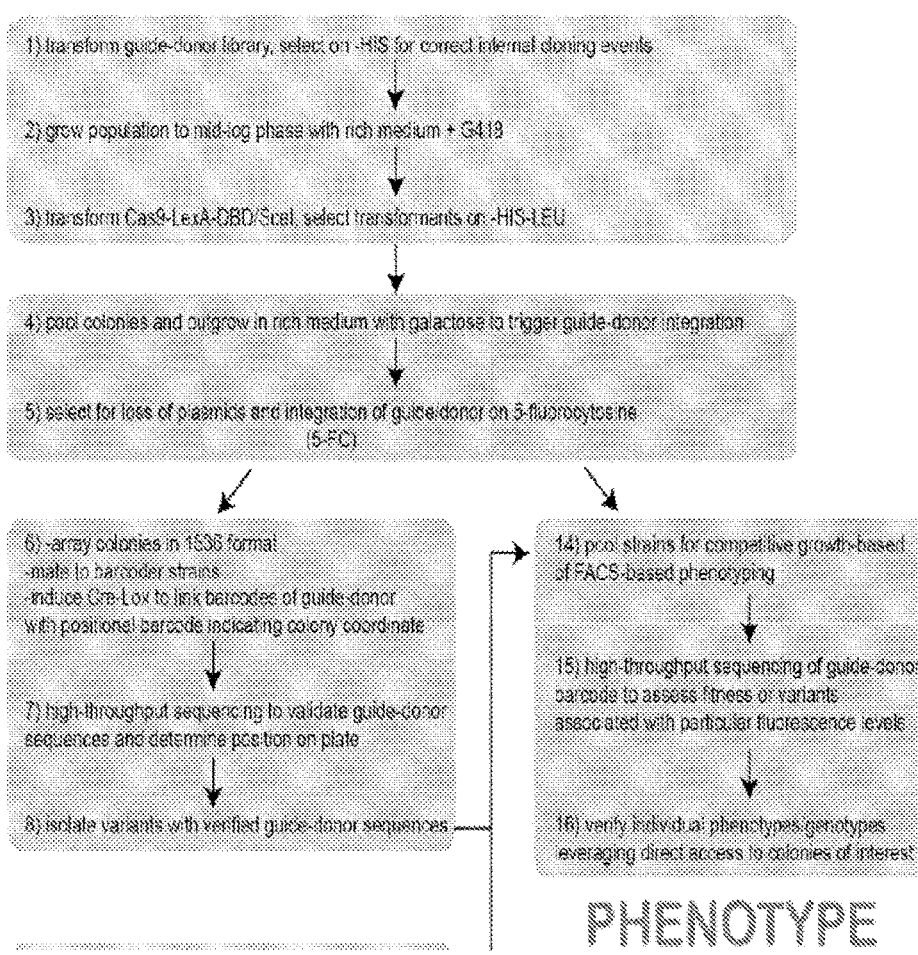
FIG. 8 shows one potential workflow for editing, barcoding, validating and phenotyping strains.

A major advantage of our system is that it leverages both our REDI strain parsing technology with our platform for high-throughput precision editing with guide-donor integration and active donor recruitment to the RGN dsDNA break site. This technology was previously applied for purifying oligos (United States Patent Application Publication No. 20160122748, which is incorporated herein by reference in its entirety), but we have here adapted the technology to allow for the creation of functional strain collections. Specifically, this enables us to parse individual edited strains, and verify both gRNA and donor sequences, allowing isolation of sequence perfect guide-donors and equimolar pooling of variant strains (FIG. 6). Another key aspect of our technology is that REDI-mediated strain parsing and re-arraying allows unambiguous confirmation of the edited locus (FIG. 7). This is not possible with any of the available strategies employing multiplexed editing, and enables assaying validated strains in separate wells for non-growth based phenotyping, which is of particular importance in numerous functional genomics applications (e.g. improving strains for production of a compound, protein, or enzymatic activity, analyzing protein localization, and for validating edited strains by multiplexed whole genome sequencing). Our platform promises to revolutionize high-throughput genome editing, enabling more efficient, accurate, and validated editing than any currently available technology or model system. The entire workflow for our platform is detailed in FIG. 8.

Figure 12:
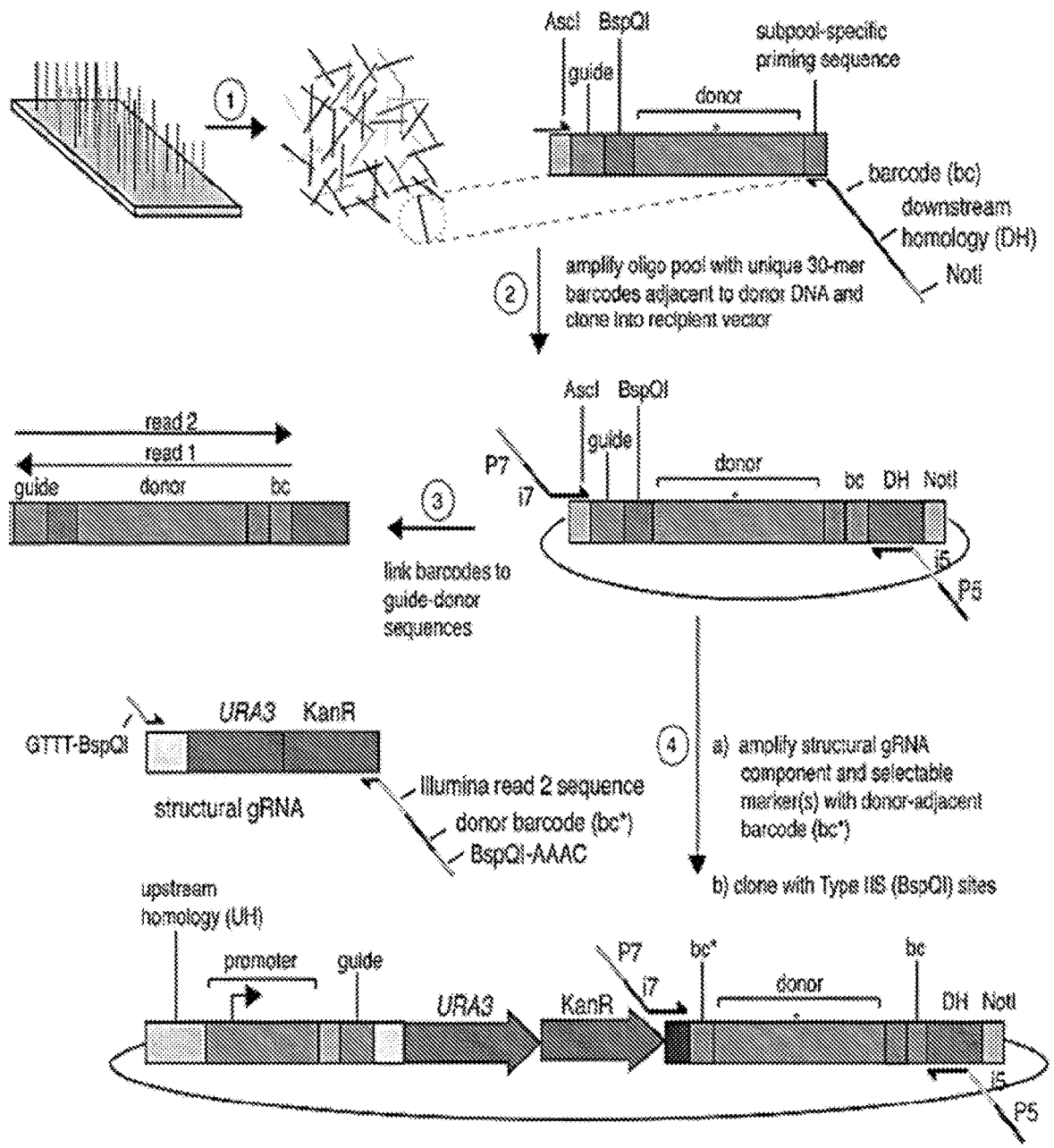
FIG. 12 shows library cloning to link guide-donors with unique DNA barcodes. (1) Oligonucleotides encoding guide-donors are synthesized in high-density array format and cleaved off of the array surface to generate a complex pool. (2) Each oligo contains common amplification sequences flanking the guide-donor cassette to enable amplification of specific subpools. The forward primer harbors a restriction site (AscI) at its 3'-end and the reverse primer encodes a distinct restriction site (NotI) at its 5'-end followed by a degenerate barcode (bc) encoding a pseudo-random sequence (either NNNVHTGNNNVHTGNNNVHTGNNNVHTGNNN or NNNTGVHNNNTGVHNNNTGVHNNNTGVHNNN) that excludes illegal restriction sites (NotI, AscI, and BspQI). The degenerate barcode is flanked by a 50 bp downstream homology sequence (DH). NotI and AscI sites enable sticky end cloning into a multi-copy recipient vector, with the AscI site at the 3'-end of the guide RNA promoter. The guide and donor sequences are separated by a type IIS restriction site (BspQI) that enables cloning with an arbitrary overhang, in this case the GTTT directly 3' of the guide sequence, to enable cloning in the constant structural component of the guide RNA.
(3) High-throughput sequencing (HTS) of the first-step cloning products enables linking the guide-BspQI-donor sequences with unique barcodes (bc). Paired-end sequencing can be used to increase confidence of base calls following quality-based merging of read 1 and read 2. (4) (a) The structural guide RNA component along with yeast-specific (e.g. URA3) and bacterial-specific (e.g. kanR) selection markers are amplified with primers harboring BspQI sequences at their 5'-ends. The reverse primer includes an additional barcode (bc*; either NNNNNN or NNNNNNHVVNHBBHBHD) situated 3' of the Illumina read 2 priming sequence, modified to contain a G-to-A SNP at the first position of the BspQI site. (b) Cleavage of the first step cloning products with BspQI followed by phosphatase treatment enables scarless cloning of the structural gRNA insert. These second-step libraries are selected with kanamycin to enable enrichment of vectors harboring the insert. Paired-end HTS of bc*-donor and bc enables mapping the barcodes to unique guide-donor combinations.
Figure 13:
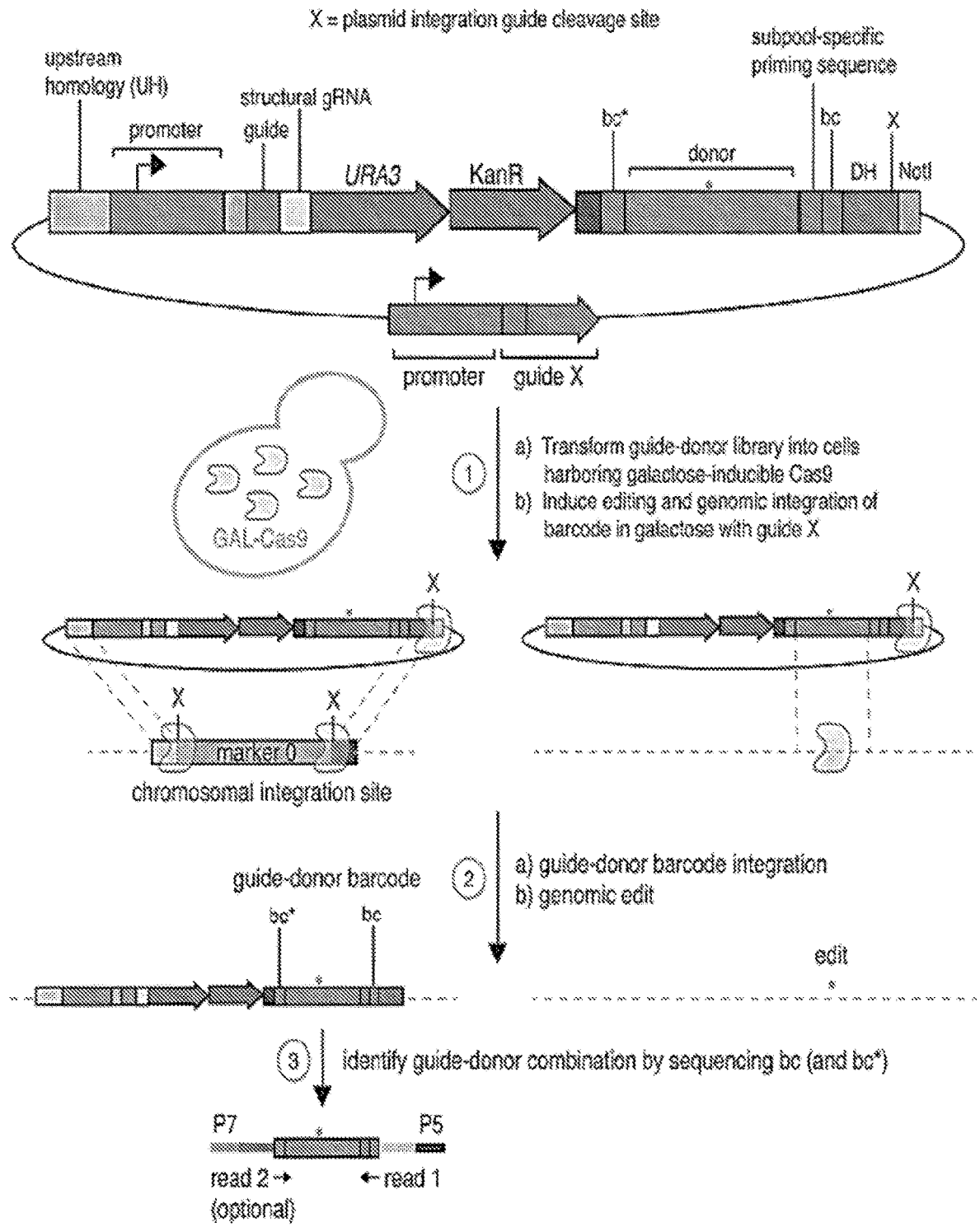
FIG. 13 shows simultaneous editing and barcode integration via self-destructing plasmids. (1) The guide-donor vectors after the second-step cloning are transformed into yeast and selected with the insert-specific marker (URA3). The recipient strain is modified to harbor a barcode integration locus with a counter-selectable marker (FCY1). In addition to the guide sequences from the library, the guide-donor plasmids also harbor a guide X expression unit to promote barcode integration, as guide X cleavage sites flank FCY1. Following transformation, the guide-donor plasmids accumulate to high copy number through outgrowth. At the 5'-end of the downstream homology (DH) sequence on the guide-donor plasmid resides a guide X cleavage site, which enables later linearization of the plasmid to accelerate plasmid loss after editing. (2) Induction of Cas9 results in guide X cleaving the plasmid and genomic barcode locus, and in the library-derived guide cleavage elsewhere in the genome. (a) Guide X cleavage results in genomic integration of the entire guide RNA-bc*-donor DNA-bc cassette via upstream homology (UH) sequence present on both the guide-donor plasmid and in the chromosomal barcode site. (b) The edit-directing guide cleavage is followed by donor DNA-directed homologous recombination to generate the intended genomic edit.

For improved phenotyping in bulk culture, we have also developed a system to barcode our editing cassette. In this system, each editing cassette is associated with a random barcode (FIG. 12). These associations are then determined by paired end sequencing of the guide and the donor with the barcode. The small barcode can then be sequenced for phenotyping experiments as a proxy for the editing cassette, reducing the cost of phenotyping and enabling internal editing replicates (FIG. 13).

Discussion

High-throughput genetic engineering using RGNs in combination with array-synthesized oligonucleotides encoding guide RNAs and donor DNAs has tremendous potential for a variety of applications[1]. Current progress in this area has been rapid, but limited to generating large mutant libraries in pools, which are not amenable to many phenotyping methods. By combining REDI with a novel high-throughput Cas9-based genome editing system using array-derived oligonucleotides, we have addressed this key limitation. Our method provides a simple mechanism to rapidly create arrayed libraries of yeast variants. It can be applied to generate mutations anywhere in the yeast genome, or in heterologous genes and pathways expressed in a yeast host and may be particularly valuable for engineering strains for high value chemical synthesis.

Methods

Figure 1B:
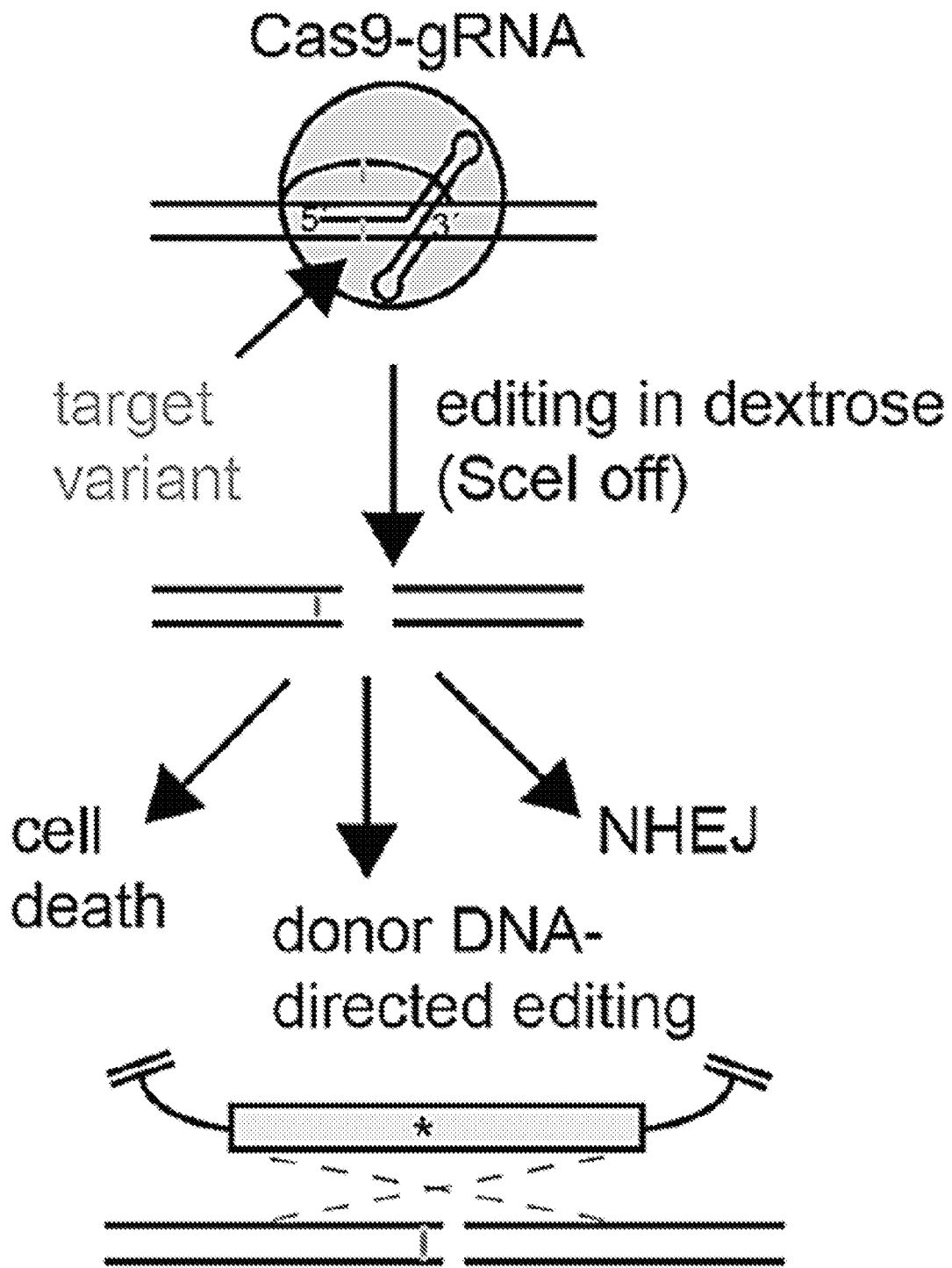
Figure 1C:
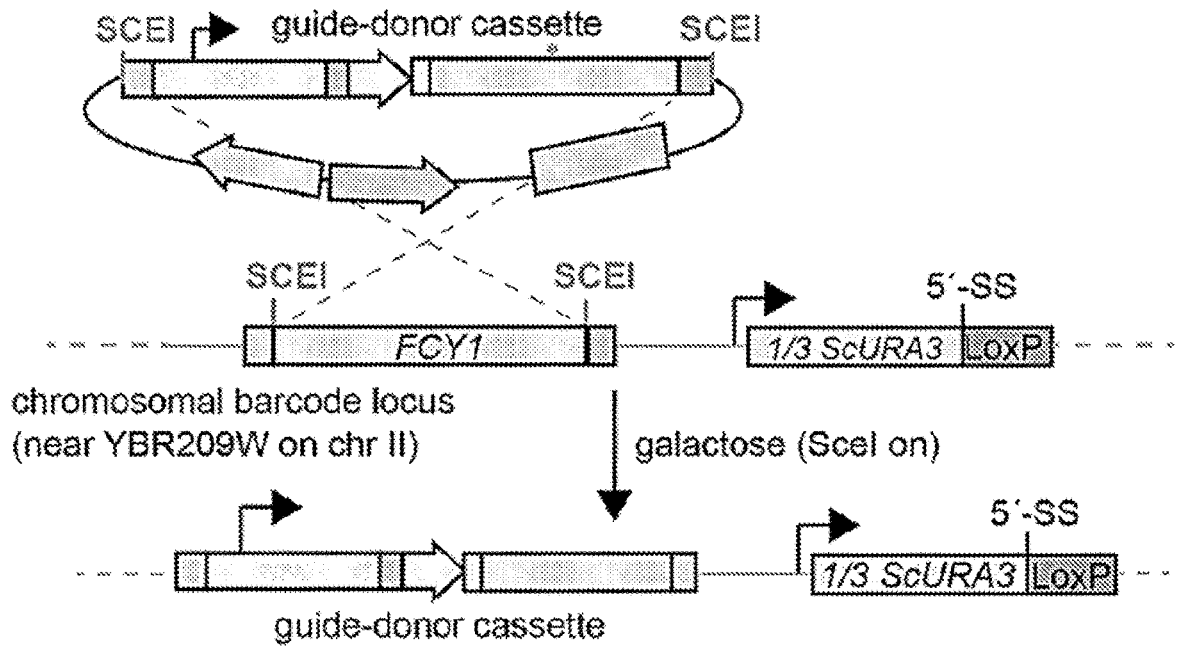

Oligonucleotide libraries are ordered from Agilent or Twist Biosciences. The basic oligo design is a sequence containing a ~20 nt specificity sequence for a CRISPR nuclease such as Cas9 or Cpf1 as well as a donor sequence that includes a desired mutation (FIG. 1). Additionally, we can add additional synonymous mutations that allow us to obtain amino acid changes outside of the cut site without requiring a PAM mutation (FIG. 10). On either side of these modification sequences is a homology sequence of ~30-90 nt that matches the genomic target.

Figure 9:
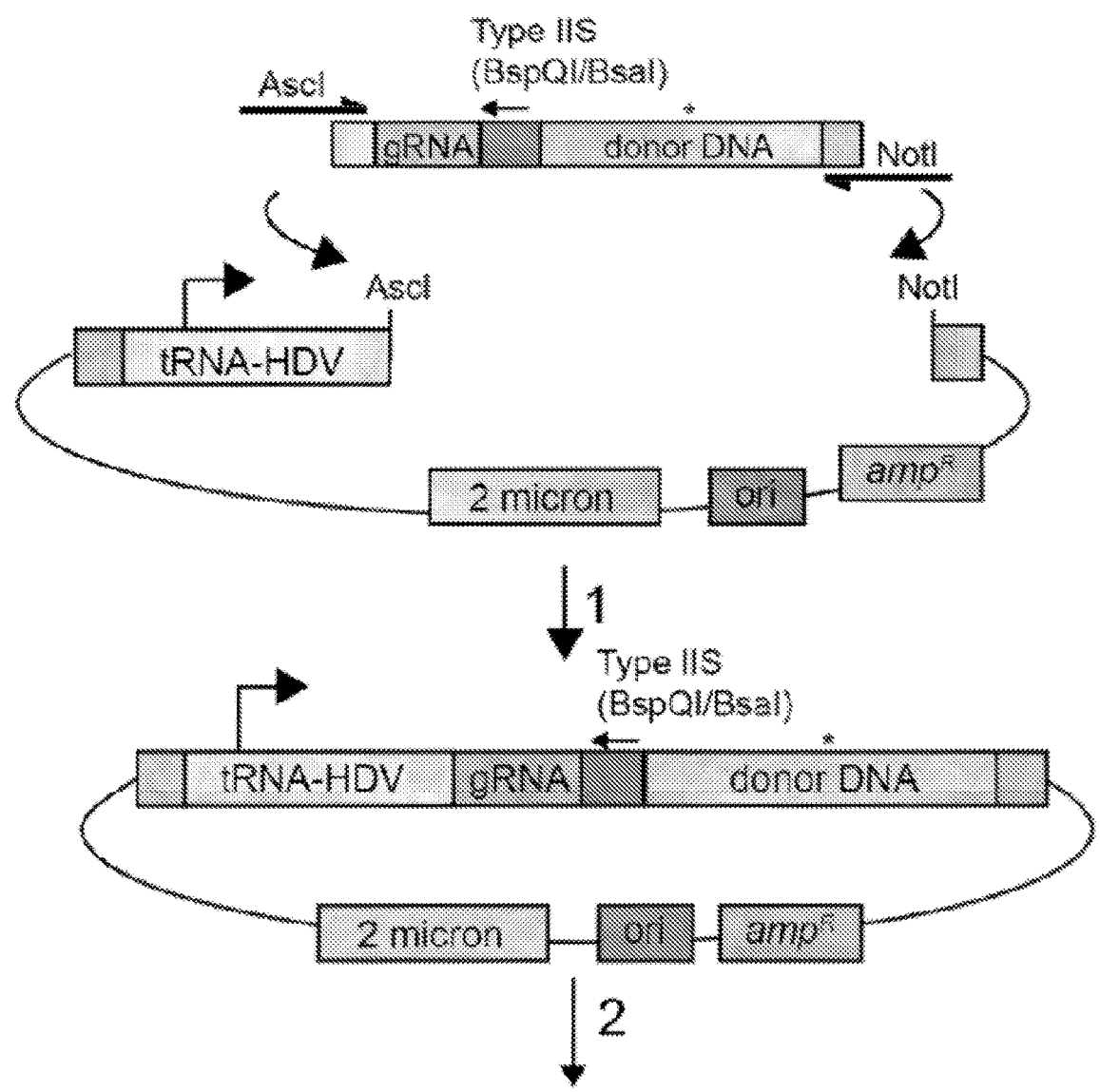
FIG. 9 shows a library cloning strategy to minimize non-functional vector background. Step 1: Oligo pools are amplified with primers containing 5'-extensions to facilitate Gibson- or sticky end-mediated cloning into vector backbones. Step 2: The amplified oligos contain an internal Type IIS restriction site. The cloned vector is treated with the Type IIS enzyme and a phosphatase. This enables scarless internal cloning of the structural guide RNA component, a Pol III terminator, and a selectable marker (e.g. HIS3). Step 3: The constant insert is treated with BspQI only to retain 5'-phosphates. Step 4: The insert is ligated into the vector backbone, and can then be transformed into recipient yeast with selection on -HIS medium.
Figure 9:
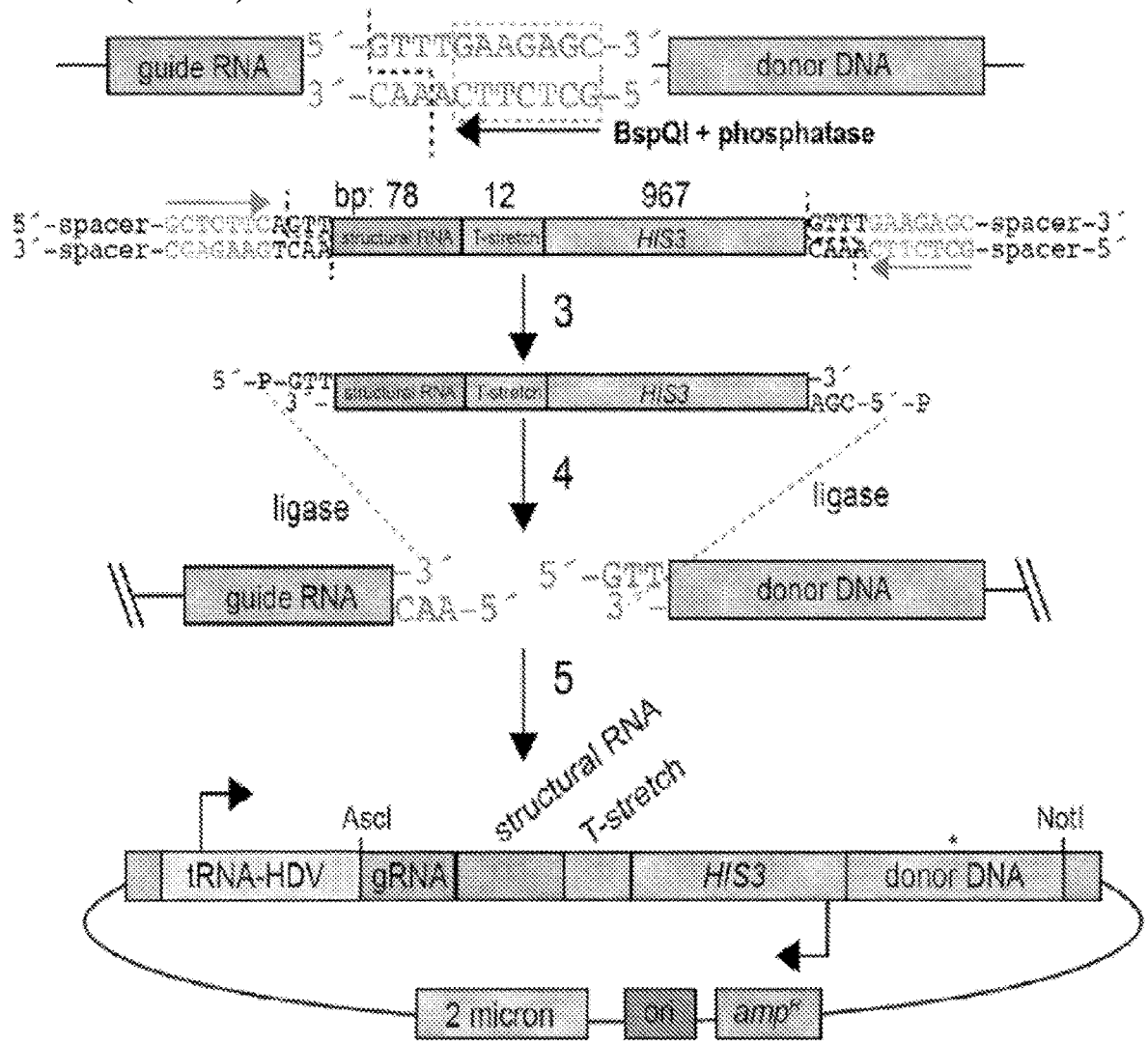

The oligos are PCR amplified with primers that can add additional sequence and then are either ligated or assembled via Gibson Assembly into a plasmid that contains a promotor to express the gRNA, and is flanked by homology for the REDI integration locus (FIG. 9). Additionally, we have developed a method that allows for internal cloning of constant parts of the gRNA as well as a selectable marker such as His3 or KanR2, which allows us to select only cassettes that have successfully incorporated the constant part of the gRNA and cut down on background due to synthesis errors or cloning errors (FIGS. 10 and 12).

Figure 5B:
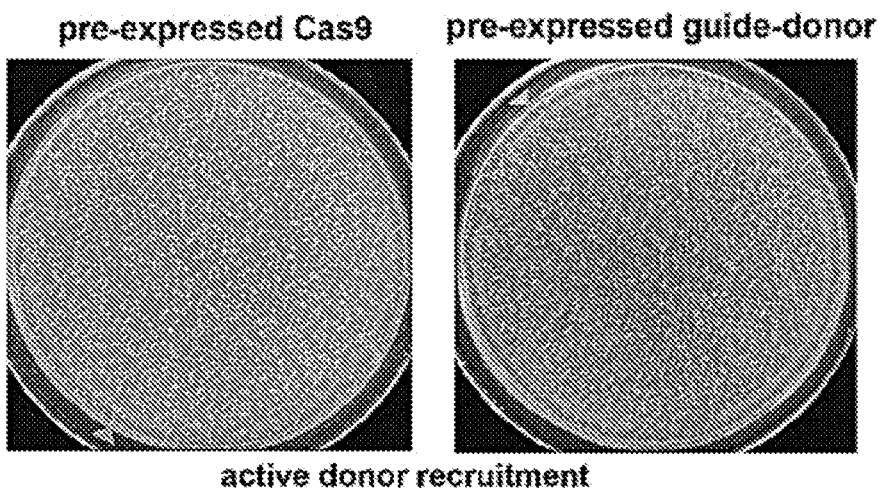

The cassettes encode two edits, one to modify the genome, and one to integrate the cassette into the REDI locus (FIGS. 1 and 13). Cas9 and the gRNA are expressed from different plasmids (FIG. 1). In different iterations of the method, either the gRNA plasmid or the Cas9 plasmid are transformed into the host (yeast) first followed by a second transformation of the other plasmid (FIGS. 1 and 5). Both are expressed under a constitutive promoter. Alternatively, we can express either under and inducible promoter such as a galactose inducible promoter or a tetracycline inducible promoter. One of the two plasmids will also contain the SceI or other site-specific nuclease gene either under an inducible or constitutive promoter. By selecting for both plasmids, we ensure that the Cas9 edit is made to the genome. We can then induce the SceI gene to integrate the gRNA-donor cassette at the REDI locus (FIG. 6), in the process deleting a counter selectable marker such as Fcy1. Alternatively, we can achieve this using a second constant guide RNA to recruit Cas9 to cut the REDI barcoding locus deleting Fcy1 and integrating the gRNA-donor-barcode cassette (FIG. 13) in a manner similar to SceI meganuclease cleavage. We can then select for successful integration of this cassette, which will serve as a barcode for the edit it encodes. These barcodes allow for parsing of edited strains with REDI and for pooled competitive growth experiments. When we perform REDI we can select only for cassettes that perfectly encode the desired edit and no other undesired edits, making our method highly specific.

In addition to Cas9, our plasmids can contain enzymes such as Fkh1-LexA or Cas9-LexA to bring the donor DNA to the site of DNA double strand breaks (FIG. 4). This can dramatically increase the survival rate of editing as well as the efficiency of homologous recombination. After editing, the resulting editing cells can be parsed in a method akin to our previously reported REDI method (FIG. 6). This additionally allows us to parse edited cells into subpools and validate that we did indeed make the intended edit by sequencing a specific region where we expect all the edits for a single plate to occur (FIG. 7). If an edit is absent from that location, we assume the strain representing that edit did not successfully make the edit and remove it from the collection.

Either before or after REDI and edit confirmation, our integrated gRNA-donor cassettes and/or their associated barcodes can be used to track edited cells. This allows high-throughput bulk culture phenotyping. Additionally, we are able to phenotype strains on arrayed plates through methods such as microscopy.

Example 2

Gene Editing Using a Cpf1-Donor System Results in Highly Efficient Editing

When a Cpf1 guide-donor system was used in a method similar to that described in Example 1, the Cpf1 guide-donor system resulted in highly efficient (>99%) editing and editing with Cpf1 was enhanced ~10-fold with donor recruitment to a similar extent as Cas9.

Figure 14A:
FIGS. 14A and 14B show that Cpf1 guide-donor system results in highly efficient (>99%) editing and editing with Cpf1 is enhanced ~10-fold with donor recruitment to a similar extent as Cas9.
Figure 14B:
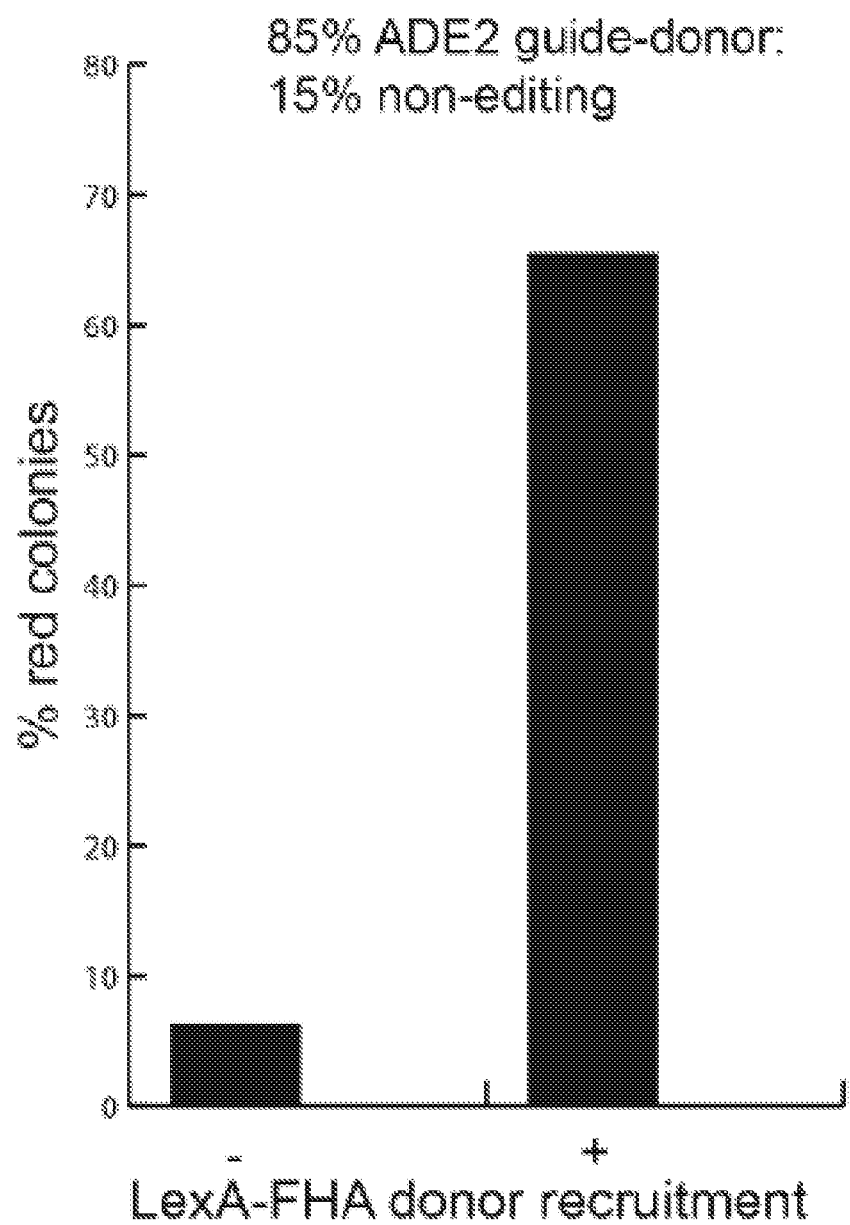
Figure 15:
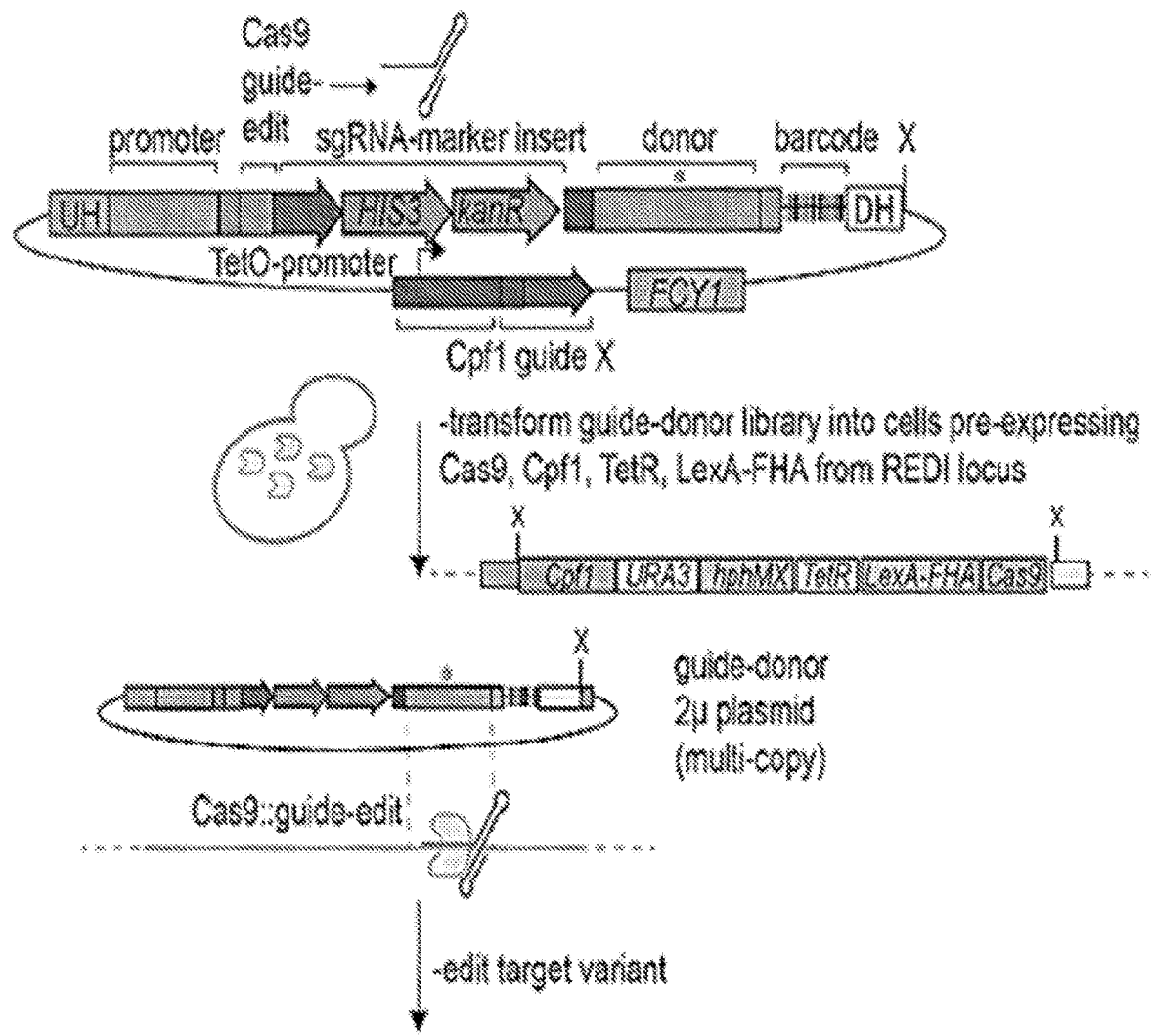
FIG. 15 shows a modified version of the multiplex genome editing system, where Cpf1 and/or Cas9 or other RNA-guided nuclease (RGN) or site-specific nuclease (e.g. SceI, other meganucleases, ZFNs, or TALENs) are expressed from the REDI locus, optionally along with other multiplex editing components, e.g. TetR and LexA-FHA and markers for forward and counter selection (URA3 and hphMX). In this arrangement, the self-destructing guide-donor vector integrates into the REDI barcoding locus with simultaneous removal of Cas9, Cpf1, and all genes in between. The genetic removal of Cas9 at the DNA level followed by sufficient outgrowth to dilute out Cas9 mRNA and protein ensures that subsequent fitness assays are not confounded by effects of Cas9::guide-edit binding to chromatin. The editing guide can be paired with either Cas9 or Cpf1, and likewise the barcoding guide X can be paired with either Cas9 or Cpf1. The advantage of having dedicated nucleases for RGNs is that there is no competition between editing and barcoding guides for associating with the RGN. This arrangement also increases the flexibility of the multiplex system with regards to allowing targeting more genomic regions by utilizing RNA-guided nucleases with different PAM requirements.
Figure 15:
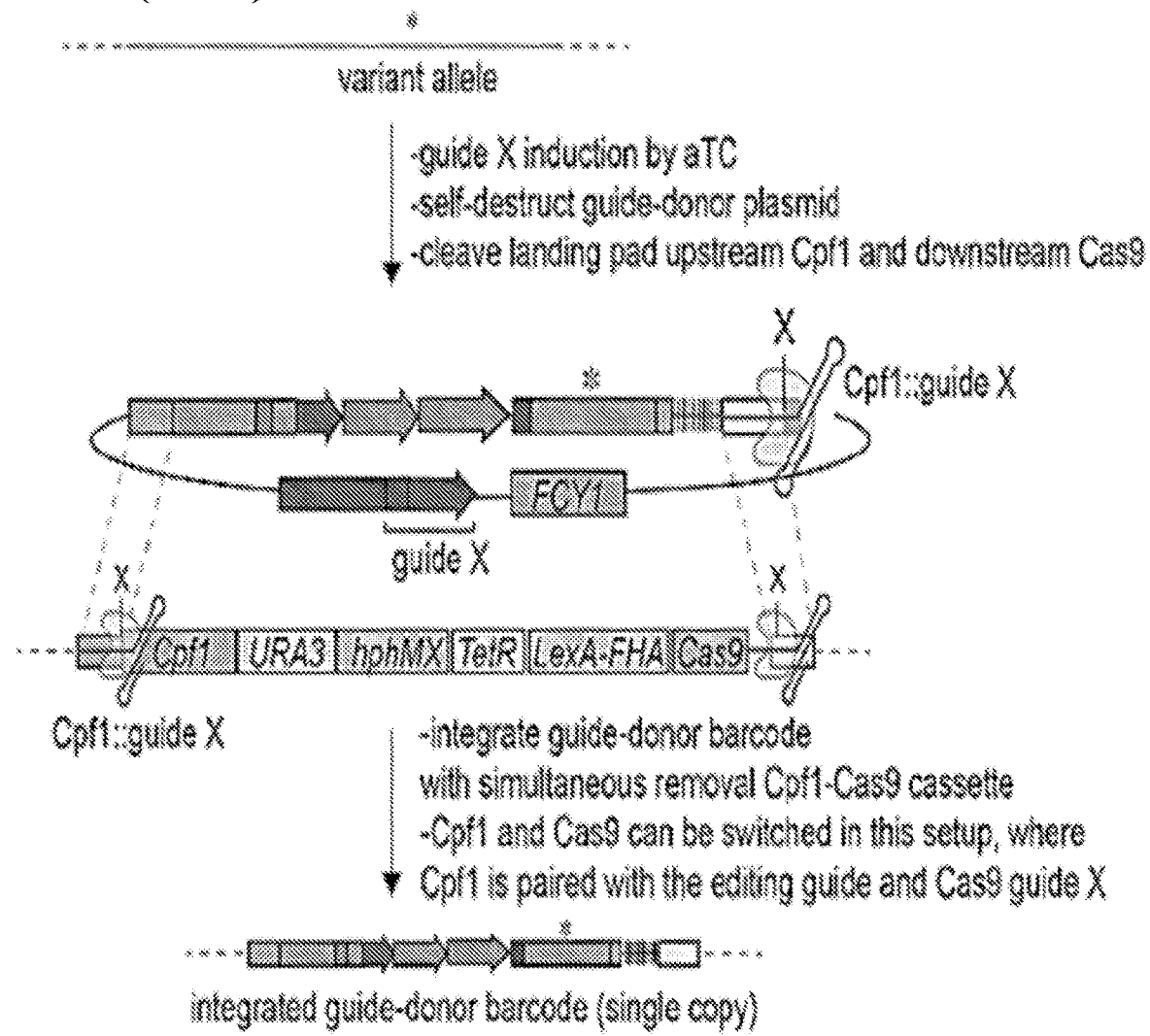

Data are provided in FIGS. 14A and 14B. FIG. 14A shows colonies of cells pre-expressing Cpf1, transformed with a Cpf1 guide-donor plasmid (the guide has the Cpf1 scaffold) targeting the ADE2 gene. The donor DNA encodes a frameshift-causing deletion. FIG. 14B shows % red colonies (ratio of red:white colonies) when Cpf1 guide-donor was mixed with a non-editing plasmid at a ratio of 17:3 and transformed into cells expressing Cpf1 without (left) or with (right) LexA-FHA.

Example 3

Figure 16:
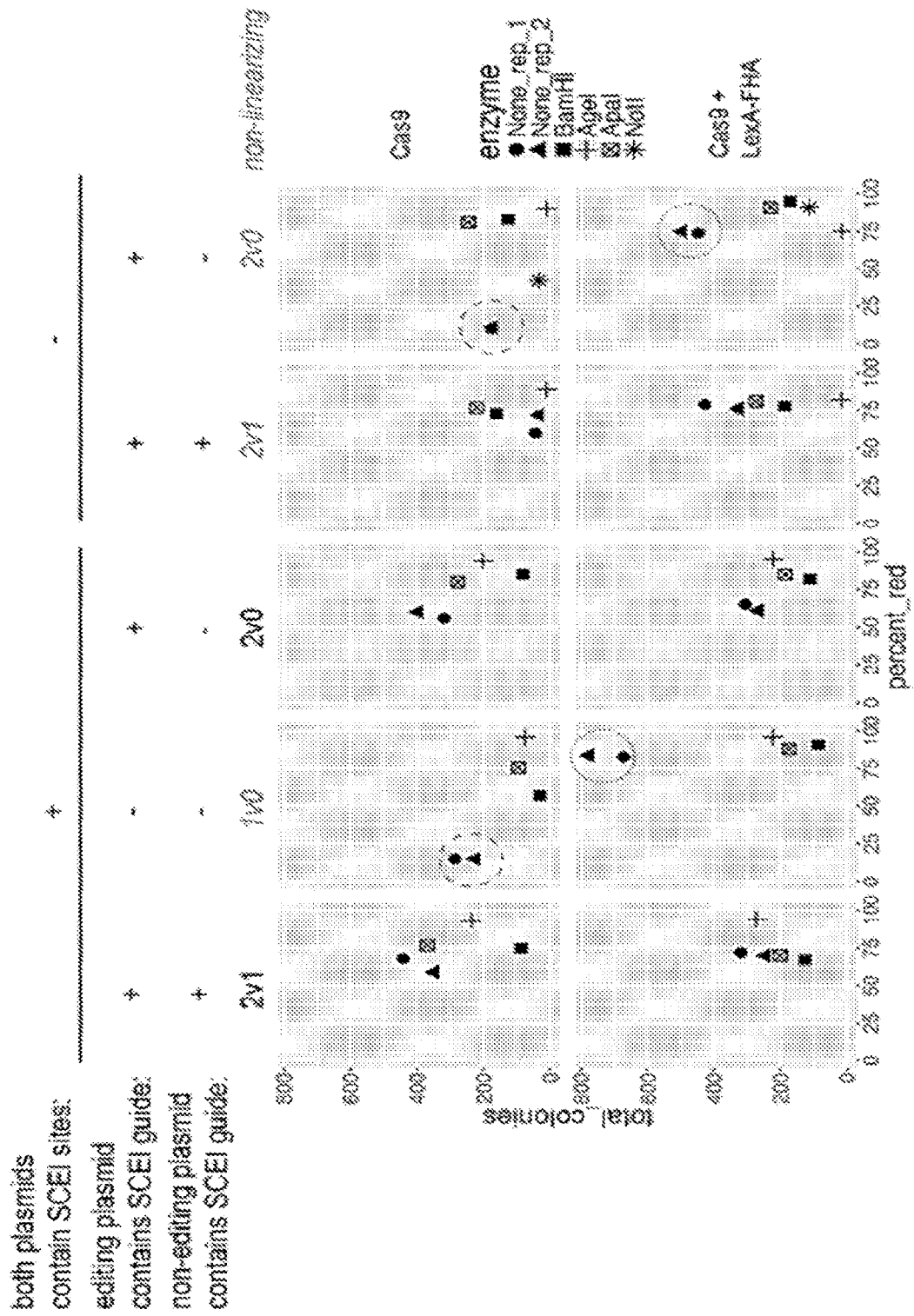
FIG. 16 shows plasmid spike-in experiments demonstrating that both LexA-FHA and linearized vectors enhance HDR efficiency and editing survival. Note that LexA-FHA with a circular plasmid results in the overall highest transformation survival.

Plasmid Spike-In Experiments Demonstrate that Both LexA-FHA and Linearized Vectors Enhance HDR Efficiency and Editing Survival A plasmid editing the ADE2 ORF was mixed at 85% (17:3) with a non-editing plasmid and transformed into a strain harboring either Cas9 (FIG. 16, top panel) or both Cas9 and LexA-FHA (FIG. 16, bottom panel). The use of the same strain for each transformation enables direct comparison of total colonies for each row.

Data are provided in FIG. 16. The y-axis indicates the total number of colonies observed in each transformation, while the x-axis indicates the percentage of colonies which are red, which is a proxy for survival of the process of editing ADE2. The shape of each point corresponds to the restriction enzyme used to linearize the plasmid in vitro, prior to transformation. The 5 different columns correspond to different versions of spike-in mixes. The first number corresponds to the number of genomic loci cut by the ADE2 editing plasmid (2 indicates cutting at ADE2 and the chromosomal barcode locus, while 1 indicates cutting only at ADE2), and the second number corresponds to the number of genomic loci cut by the non-editing plasmid (1 indicates cutting at the guide X recognition site (in this case the SceI site) at the chromosomal barcode locus, while 0 indicates no guide RNAs on the non-editing plasmids). For example, 2v1 corresponds to a mix where the ADE2 editing plasmid is cutting the genome at both the ADE2 ORF and the chromosomal barcode locus, and the non-editing plasmid only cuts the chromosomal barcode locus. Additionally the plasmids either contain the SceI site, in which case they are cleaved by the SceI guide RNA which also targets the chromosomal barcode locus, or they do not contain the SceI site, in which case the plasmids remain intact even if the SceI guide is expressed. Plasmids cut with the SceI gRNA become linearized in vivo. As these different mixes are prepared separately (although quantified at 85% by mass), the most valid comparisons for % red colonies can be made in each column separately. The toxicity of editing in the absence of LexA-FHA or plasmid linearization results in little survival (samples in dashed circles, no enzyme—None reps 1 and 2). The greatest transformation survival occurs with LexA-FHA without plasmid linearization (samples in dotted circles, no enzyme—None reps 1 and 2).

These data show either plasmid linearization prior to transformation or the use of a targeting fusion protein (e.g., LexA-FHA) can greatly boost editing efficiency relative to non-editing plasmids. Additionally, this method does not require plasmids to be transformed, it is also compatible with linear donor molecules because the barcode is captured in the barcoding locus. Furthermore, plasmid linearization in vivo increases the ratio of properly edited cells to those with a non-editing guide. The amplification of non-editing guide vectors is reduced either with linear donor, self cleaving donor plasmid, or LexA-FHA. The overall number of colonies that can be obtained, which is important for making complex libraries, is highest in the presence of a donor recruitment protein, such as LexA-FHA.

Example 4

Donor DNA Recruitment in Human Cells

The donor recruitment technology described herein can also be used in mammalian cells. Applying the same concepts that worked for yeast, a protein was selected that is recruited to DNA double strand breaks, TP53BP1. The normal role of TP53BP1 in the cell is to bind to double strand breaks and promoter non-homologous end joining (NHEJ). A subdomain of this protein, amino acids 1221 to 1718, has been shown to act in a dominant negative fashion to NHEJ (dn53BP1) (Xie et al., 2007). We hypothesized that this protein would be recruited to breaks, and when fused to LexA DNA binding domain, could be used to bring donor DNA to the site of breaks when the donor DNA contained LexA sites. Additionally, because it could inhibit NHEJ, it might increase the rate of homology directed repair (HDR) regardless of whether or not LexA sites were provided.

To test this, two versions of a plasmid expressing an NLS, dn53BP1, with a C-terminal LexA DNA binding domain fused to it were created. One version expresses a gRNA to CACNA1D and the other version expresses a gRNA to the gene PPP1R12C. The gRNAs for these sites were previously characterized (Wang et al., 2018). A second plasmid expressing Cas9 and a third plasmid containing a donor sequence (~300 nt of homology flanking either side of an XbaI site that would be introduced, deleting a small section of DNA including the gRNA PAM sequence) to either CACNA1D or PPP1R12C were used. There were two version of each donor plasmid, one with 4 LexA sites and one with no LexA sites. The plasmids were built with Gibson Assembly. Cas9 and the dn53BP1-LexA were both expressed from the EF1 alpha promoter.

Each of the three plasmids (25 ng) were transiently transfected into Hek293 cells that were plated the day before at a density of 10,000 cells per well in 96 well plates, using the X-tremeGENE 9 transfection reagent (Sigma Aldrich). Each set of conditions was tested in triplicate. The cells were grown for 72 hours post transfection and then harvested by removing the media and washing the cells with water. Half the cells were transferred to a 96 well PCR plate, pelleted, and then the DNA was extracted using 100 µl per sample of Lucigen QuickExtract DNA extraction solution.

The QuickExtract solution was then diluted 1/5 by adding 5 µl of QuickExtract to 20 µl of water. From this 2 µl was used to inoculate PCRs. 14 cycles of PCR were performed in 25 µl of Q5 PCR mix with inner primers that bound to the gene target of interest and also add the Read1 and Read2 TruSeq primers (Illumina). One primer bound far enough away from the edit site as to not be found in the provided homology region of the donor DNA, such that only genomic DNA would be amplified (not donor DNA). The other primer bound 32 or 33 nt away from the DNA sequence to be introduced by homology directed repair (HDR). This primer was used with Read1. After the first 14 cycles, and additional 25 µl of Q5 PCR mix with primers that added P5 and P7 adapter (Illumina) as well as sequencing indices.

The samples were sequenced on an Illumina MiSeq to look at the distribution of edits at the cut site. As the Read1 primer was much closer to the cut site, Read1 was analyzed to determine the rates of HDR and NHEJ. NHEJ was defined as sequences that that contained insertions or deletions within the gRNA recognition sequence or PAM sequence of the target gene. HDR was defined as sequences that mapped to the donor sequence.

Results

Figure 17:
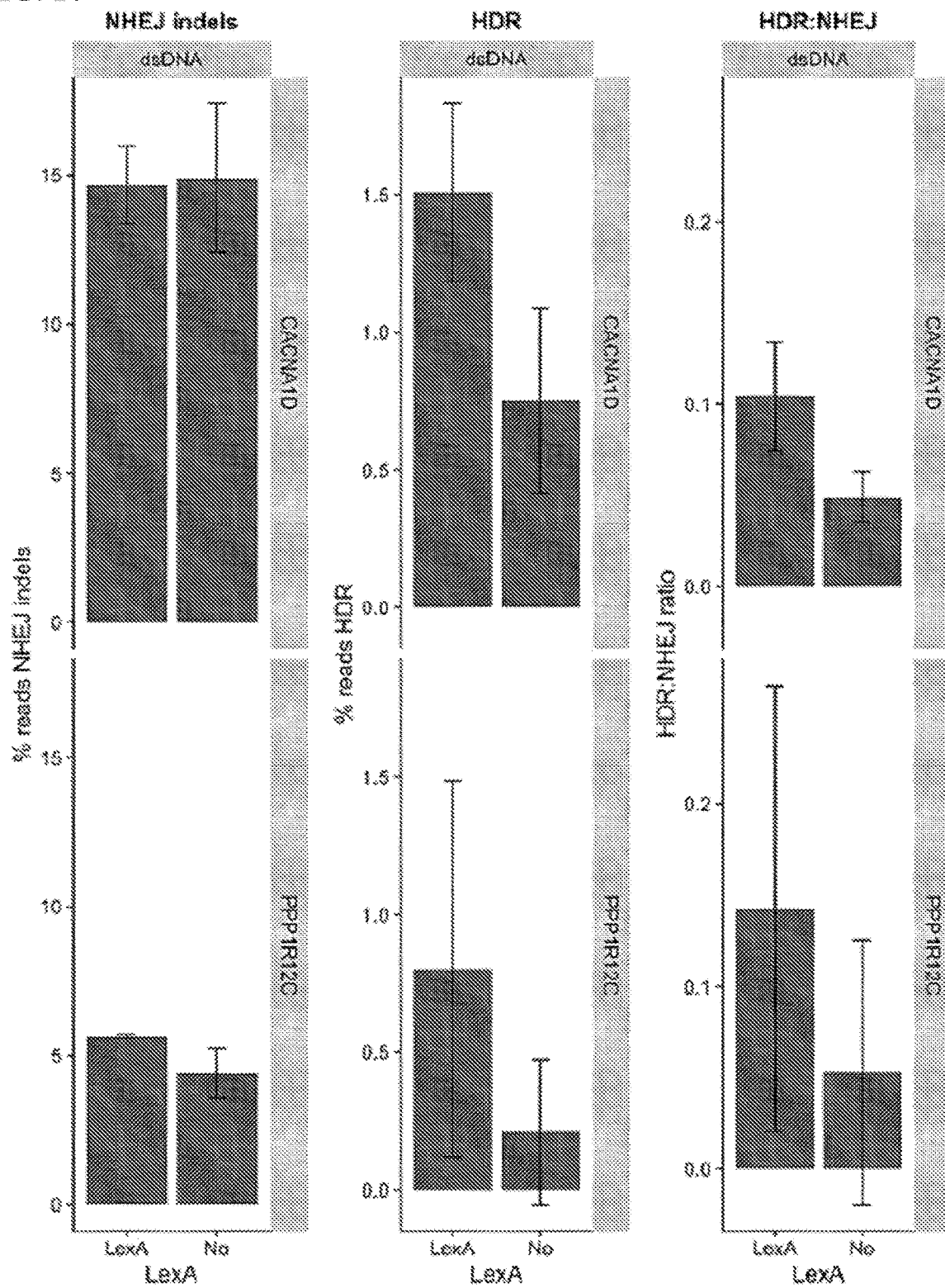
FIG. 17 shows the efficiency of HDR in human cells with or without LexA sites in the presence of the donor recruitment protein, dn53BP1-LexA. Two independent genes were targeted (CACNA1D (CAC) and PPP1R12C (PPP)). The first panel shows the rate of NHEJ at the cut site. The second panel shows the percentage total HDR at the cut site, and the third panel shows the ratio of HDR to NHEJ in the cells.

FIG. 17 shows the efficiency of HDR with or without LexA sites in the presence of the donor recruitment protein, dn53BP1-LexA. Two independent genes were targeted (CACNA1D (CAC) and PPP1R12C (PPP)). The first panel shows the rate of NHEJ at the cut site. The second panel shows the percentage total HDR at the cut site, and the third panel shows the ratio of HDR to NHEJ in the cells.

It was found that dn53BP1-LexA fusions could increase the rate of HDR at the gRNA cut site in the presence of LexA DNA sites on the donor plasmid DNA. When LexA sites are absent on the donor plasmid, no increase in HDR was observed, but there was a similar rate of NHEJ. This suggests DNA repair can generally be improved through the use of fusion proteins that are recruited to breaks and contain a domain that binds to the donor DNA and brings it to the site of breaks.

REFERENCES

1. Garst A D, Bassalo M C, Pines G, Lynch S A, Halweg-Edwards A L, Liu R, et al. Genome-wide mapping of mutations at single-nucleotide resolution for protein, metabolic and genome engineering. Nat Biotechnol [Internet]. 2016 Dec. 12; Available from: http://www.ncbi.nlm.nih.gov/pubmed/27941803
2. Jinek M, Chylinski K, Fonfara I, Hauer M, Doudna J A, Charpentier E. A programmable dual-RNA-guided DNA endonuclease in adaptive bacterial immunity. Science. 2012 August; 337(6096):816-21.
3. Koike-Yusa H, Li Y, Tan E-P, Velasco-Herrera M D C, Yusa K. Genome-wide recessive genetic screening in mammalian cells with a lentiviral CRISPR-guide RNA library. Nat Biotechnol. 2014 March; 32(3):267-73.
4. Shalem O, Sanjana N E, Hartenian E, Shi X, Scott D A, Mikkelsen T S, et al. Genome-scale CRISPR-Cas9 knock-out screening in human cells. Science. 2014 January; 343(6166):84-7.
5. Wang T, Wei J J, Sabatini D M, Lander E S. Genetic screens in human cells using the CRISPR-Cas9 system. Science. 2014 January; 343(6166):80-4.
6. Zhou Y, Zhu S, Cai C, Yuan P, Li C, Huang Y, et al. High-throughput screening of a CRISPR/Cas9 library for functional genomics in human cells. Nature. 2014 May; 509(7501):487-91.
7. Gilbert L A, Horlbeck M A, Adamson B, Villalta J E, Chen Y, Whitehead E H, et al. Genome-Scale CRISPR-Mediated Control of Gene Repression and Activation. Cell. 2014 October; 159(3):647-61.
8. Konermann S, Brigham M D, Trevino A E, Joung J, Abudayyeh O O, Barcena C, et al. Genome-scale transcriptional activation by an engineered CRISPR-Cas9 complex. Nature. 2015 January; 517(7536):583-8.
9. Ronda C, Maury J, Jakočiunas T, Jacobsen S A B, Germann S M, Harrison S J, et al. CrEdit: CRISPR mediated multi-loci gene integration in *Saccharomyces cerevisiae*. Microb Cell Fact. 2015; 14:97.
10. Ryan O W, Skerker J M, Maurer M J, Li X, Tsai J C, Poddar S, et al. Selection of chromosomal DNA libraries using a multiplex CRISPR system. Elife. 2014; 3.
11. Jakočiūnas T, Bonde I, Herrgård M, Harrison S J, Kristensen M, Pedersen L E, et al. Multiplex metabolic pathway engineering using CRISPR/Cas9 in *Saccharomyces cerevisiae*. Metab Eng. 2015 March; 28:213-22.
12. Bao Z, Xiao H, Liang J, Zhang L, Xiong X, Sun N, et al. Homology-integrated CRISPR-Cas (HI-CRISPR) system for one-step multigene disruption in *Saccharomyces cerevisiae*. ACS Synth Biol. 2015 May; 4(5):585-94.
13. DiCarlo J E, Norville J E, Mali P, Rios X, Aach J, Church G M. Genome engineering in *Saccharomyces cerevisiae* using CRISPR-Cas systems. Nucleic Acids Res. 2013 April; 41(7):4336-43.
14. Ryan O W, Cate J H D. Multiplex engineering of industrial yeast genomes using CRISPRm. Methods Enzymol. 2014; 546:473-89.
15. Richardson C D, Ray G J, DeWitt M A, Curie G L, Corn J E. Enhancing homology-directed genome editing by catalytically active and inactive CRISPR-Cas9 using asymmetric donor DNA. Nat Biotechnol. 2016 January;
16. Chu V T, Weber T, Wefers B, Wurst W, Sander S, Rajewsky K, et al. Increasing the efficiency of homology-directed repair for CRISPR-Cas9-induced precise gene editing in mammalian cells. Nat Biotechnol. 2015 May; 33(5):543-8.
17. Justin D. Smith, Ulrich Schlecht, Weihong Xu, Sundari Suresh, Joe Horecka, Michael J. Proctor, Raeka S. Aiyar, Richard A. O. Bennett, Angela Chu, Yong Fuga Li, Kevin Roy, Ronald W. Davis, Lars M. Steinmetz, Richard W. Hyman, Sasha F. Levy RPSO. High-throughput Parsing of Complex DNA Libraries for Isolation and Functional Characterization of Clonal, Sequence-verified DNA. Revis Mol Syst Biol.
18. Wang, Y., Liu, K. I., Sutrisnoh, N.-A. B., Srinivasan, H., Zhang, J., Li, J., . . . Tan, M. H. (2018). Systematic evaluation of CRISPR-Cas systems reveals design principles for genome editing in human cells. Genome Biology, 19(1), 62. https://doi.org/10.1186/s13059-018-1445-x
19. Xie, A., Hartlerode, A., Stucki, M., Odate, S., Puget, N., Kwok, A., . . . Scully, R. (2007). Distinct roles of chromatin-associated proteins MDC1 and 53BP1 in mammalian double-strand break repair. Molecular Cell, 28(6), 1045-1057. https://doi.org/10.1016/j.molcel.2007.12.005

EMBODIMENTS

Embodiment 1

A method for multiplex genetic modification and barcoding of cells, the method comprising: a) providing a plurality of recombinant polynucleotides, wherein each recombinant polynucleotide comprises a genome editing cassette comprising a polynucleotide encoding a guide RNA (gRNA) capable of hybridizing at a genomic target locus to be modified and a donor polynucleotide comprising a 5' homology arm that hybridizes to a 5' genomic target sequence and a 3' homology arm that hybridizes to a 3' genomic target sequence flanking a nucleotide sequence comprising an intended edit to be integrated into the genomic target locus, wherein each recombinant polynucleotide comprises a different genome editing cassette comprising a different guide RNA-donor polynucleotide combination, such that the plurality of recombinant polynucleotides is capable of producing a plurality of different intended edits at one or more genomic target loci; and b) transfecting the cells with the plurality of recombinant polynucleotides; c) culturing the transfected cells under conditions suitable for transcription, wherein guide RNAs are produced from each genome editing cassette; d) introducing an RNA-guided nuclease into the cells, wherein the RNA-guided nuclease forms complexes with the guide RNAs produced in the cells, said guide RNAs directing the complexes to the one or more genomic target loci, wherein the RNA-guided nuclease creates double-stranded breaks in the genomic DNA of the cells at the one or more genomic target loci, and the donor polynucleotide present in each cell is integrated at the genomic target locus recognized by its 5' homology arm and 3' homology arm by homology directed repair (HDR) such that a plurality of genetically modified cells are produced;

and e) barcoding the plurality of genetically modified cells by integrating the genome editing cassette present in each genetically modified cell at a chromosomal barcode locus.

Embodiment 2

The method of embodiment 1, wherein each genome editing cassette further comprises a promoter operably linked to the polynucleotide encoding the guide RNA.

Embodiment 3

The method of embodiment 1, wherein the chromosomal barcode locus further comprises a promoter that becomes operably linked to the polynucleotide encoding the guide RNA of any genome editing cassette that integrates at the chromosomal barcode locus.

Embodiment 4

The method of embodiment 1, wherein each recombinant polynucleotide is provided by a vector.

Embodiment 5

The method of embodiment 4, wherein the vector comprises a promoter that is operably linked to the polynucleotide encoding the guide RNA.

Embodiment 6

The method of embodiment 5, wherein the promoter is a constitutive or inducible promoter.

Embodiment 7

The method of embodiment 4, further comprising replication of the vector inside the transfected cells.

Embodiment 8

The method of embodiment 4, wherein the vector is a plasmid or viral vector.

Embodiment 9

The method of embodiment 4, wherein the vector is a high copy number vector.

Embodiment 10

The method of embodiment 1, wherein the RNA-guided nuclease is provided by a vector or a recombinant polynucleotide integrated into the genome of the cells.

Embodiment 11

The method of embodiment 10, wherein the genome editing cassette and the RNA-guided nuclease are provided by a single vector or separate vectors.

Embodiment 12

The method of embodiment 1, wherein the genome editing cassette further comprises a tRNA sequence at the 5' end of the nucleotide sequence encoding the guide RNA.

Embodiment 13

The method of embodiment 1, wherein the genome editing cassette further comprises a nucleotide sequence encoding a hepatitis delta virus (HDV) ribozyme at the 5' end of the nucleotide sequence encoding the guide RNA.

Embodiment 14

The method of embodiment 1, wherein the RNA-guided nuclease is a Cas nuclease or an engineered RNA-guided Fold-nuclease.

Embodiment 15

The method of embodiment 14, wherein the Cas nuclease is Cas9 or Cpf1.

Embodiment 16

The method of embodiment 1, wherein each donor polynucleotide introduces a different mutation into the genomic DNA.

Embodiment 17

The method of embodiment 16, wherein the mutation is selected from the group consisting of an insertion, deletion, and substitution.

Embodiment 18

The method of embodiment 16, wherein at least one donor polynucleotide introduces a mutation that inactivates a gene in the genomic DNA.

Embodiment 19

The method of embodiment 1, wherein at least one donor polynucleotide removes a mutation from a gene in the genomic DNA.

Embodiment 20

The method of embodiment 1, wherein the plurality of recombinant polynucleotides is capable of producing mutations at multiple sites within a single gene or non-coding region.

Embodiment 21

The method of embodiment 1, wherein the plurality of recombinant polynucleotides is capable of producing mutations at multiple sites in different genes or non-coding regions.

Embodiment 22

The method of embodiment 1, wherein said integrating the genome editing cassette present in each genetically modified cell at the chromosomal barcode locus is performed using HDR.

Embodiment 23

The method of embodiment 22, wherein each recombinant polynucleotide further comprises a pair of universal homology arms flanking the genome editing cassette that are capable of hybridizing to complementary sequences at the chromosomal barcode locus to allow said integration of the genome editing cassette at the chromosomal barcode locus by the HDR.

Embodiment 24

The method of embodiment 23, wherein each recombinant polynucleotide further comprises a second guide RNA capable of hybridizing at the chromosomal barcode locus.

Embodiment 25

The method of embodiment 24, wherein the RNA-guided nuclease further forms a complex with the second guide RNA, said second guide RNA directing said complex to the chromosomal barcode locus, wherein the RNA-guided nuclease creates a double-stranded break at the chromosomal barcode locus, and the genome editing cassette is integrated into the chromosomal barcode locus by the HDR.

Embodiment 26

The method of embodiment 1, wherein said integrating the genome editing cassette present in each genetically modified cell at the chromosomal barcode locus is performed using a site-specific recombinase system.

Embodiment 27

The method of embodiment 26, wherein the site-specific recombinase system is a Cre-loxP site-specific recombinase system, a Flp-FRT site-specific recombinase system, a PhiC31-att site-specific recombinase system, or a Dre-rox site-specific recombinase system.

Embodiment 28

The method of embodiment 27, wherein the chromosomal barcode locus further comprises a first recombination target site for a site-specific recombinase and the recombinant polynucleotide further comprises a second recombination target site for the site-specific recombinase, and site-specific recombination between the first recombination target site and the second site-specific recombination site results in said integrating of the genome editing cassette at the chromosomal barcode locus.

Embodiment 29

The method of embodiment 1, further comprising using a selectable marker that selects for clones that have undergone successful integration of the donor polynucleotide at the genomic target locus or successful integration of the genome editing cassette at the chromosomal barcode locus.

Embodiment 30

The method of embodiment 1, wherein the cells are yeast cells.

Embodiment 31

The method of embodiment 1, wherein the yeast cells are haploid yeast cells.

Embodiment 32

The method of embodiment 1, wherein each recombinant polynucleotide further comprises a pair of restriction sites flanking the genome editing cassette.

Embodiment 33

The method of embodiment 32, wherein the restriction sites are recognized by a meganuclease that generates a DNA double-strand break.

Embodiment 34

The method of embodiment 33, wherein expression of the meganuclease is controlled by an inducible promoter.

Embodiment 35

The method of embodiment 34, wherein the meganuclease is SceI.

Embodiment 36

The method of embodiment 1, further comprising performing additional rounds of genetic modification and genomic barcoding on the genetically modified cells by repeating (a)-(e) using different genome editing cassettes.

Embodiment 37

The method of embodiment 1, wherein each genome editing cassette further comprises a unique barcode sequence for identifying the guide RNA and the donor polynucleotide encoded by each genome editing cassette.

Embodiment 38

The method of embodiment 37, further comprising sequencing each genome editing cassette.

Embodiment 39

The method of embodiment 38, wherein said sequencing is performed prior to transfecting the cells.

Embodiment 40

The method of embodiment 37, further comprising deleting the polynucleotide encoding the guide RNA and the donor polynucleotide at the chromosomal barcode locus where each genome editing cassette integrates while retaining the unique barcode at said chromosomal barcode locus.

Embodiment 41

The method of embodiment 40, further comprising sequencing the barcode at the chromosomal barcode locus of at least one genetically modified cell to identify the genome editing cassette used in genetically modifying said cell.

Embodiment 42

The method of embodiment 1, further comprising inhibiting non-homologous end joining (NHEJ).

Embodiment 43

The method of embodiment 42, wherein said inhibiting comprises contacting cells with a small molecule inhibitor selected from the group consisting of wortmannin and Scr7.

Embodiment 44

The method of embodiment 42, wherein said inhibiting comprises using RNA interference or CRISPR-interference to inhibit expression of a protein component of the NHEJ pathway.

Embodiment 45

The method of embodiment 1, further comprising using an HDR enhancer or active donor recruitment to increase the frequency of HDR in the cells.

Embodiment 46

The method of embodiment 1, further comprising using a selectable marker that selects for clones that have undergone successful integration of the donor polynucleotides at the one or more genomic target loci by HDR.

Embodiment 47

The method of embodiment 1, further comprising phenotyping at least one genetically modified cell.

Embodiment 48

The method of embodiment 1, further comprising sequencing an entire genome of at least one genetically modified cell.

Embodiment 49

The method of embodiment 1, further comprising sequence verification and arraying of the plurality of genetically modified cells, the method comprising: a) plating the plurality of genetically modified cells in an ordered array on media suitable for growth of the genetically modified cells; b) culturing the plurality of genetically modified cells under conditions whereby each genetically modified cell produces a colony of clones in the ordered array; c) introducing a genome editing cassette from a colony in the ordered array into a barcoder cell, wherein the barcoder cell comprises a nucleic acid comprising a recombination target site for a site-specific recombinase and a barcode sequence that identifies the position of the colony in the ordered array to which the genome editing cassette corresponds; d) translocating the genome editing cassette to a position adjacent to the barcode sequence of the barcoder cell using a site-specific recombinase system, wherein site-specific recombination with the recombination target site of the barcoder cell generates a nucleic acid comprising the barcode sequence linked to the genome editing cassette; e) sequencing the nucleic acid comprising the barcode sequence of the barcoder cell linked to the genome editing cassette to identify the sequences of the guide RNA and the donor polynucleotide of the genome editing cassette from the colony, wherein the barcode sequence of the barcoder cell is used to identify the position of the colony in the ordered array from which the genome editing cassette originated; and f) picking a clone comprising the genome editing cassette from the colony in the ordered array identified by the barcode of the barcoder cell.

Embodiment 50

The method of embodiment 49, wherein the genetically modified cells are haploid yeast cells and the barcoder cells are haploid yeast cells capable of mating with the genetically modified cells.

Embodiment 51

The method of embodiment 50, wherein said introducing a genome editing cassette from a colony in the ordered array into a barcoder cell comprises mating the clone from the colony with the barcoder cell to produce a diploid yeast cell.

Embodiment 52

The method of embodiment 51, wherein the genetically modified cells are of strain MATα and the barcoder yeast cells are of strain MATa.

Embodiment 53

The method of embodiment 51, wherein the genetically modified cells are of strain MATa and the barcoder yeast cells are of strain MATα.

Embodiment 54

The method of embodiment 49, wherein the genome editing cassette is flanked by restriction sites recognized by a meganuclease.

Embodiment 55

The method of embodiment 54, wherein the recombinase system in the barcoder cell uses the meganuclease to generate a DNA double-strand break.

Embodiment 56

The method of embodiment 49, wherein the recombinase system in the barcoder cell is a Cre-loxP site-specific recombinase system, a Flp-FRT site-specific recombinase system, a PhiC31-att site-specific recombinase system, or a Dre-rox site-specific recombinase system.

Embodiment 57

The method of embodiment 49, further comprising repeating c) through f) with all the colonies in the ordered array to identify the sequences of the guide RNAs and the donor polynucleotides of the genome editing cassettes for every colony in the ordered array.

Embodiment 58

An ordered array of colonies comprising clones of the genetically modified cells produced by the method of embodiment 49, wherein the colonies are indexed according to the verified sequences of their guide RNAs and donor polynucleotides.

Embodiment 59

A method of promoting homology directed repair (HDR) by active donor recruitment to a DNA break, the method comprising: a) introducing into a cell a fusion protein comprising a protein that selectively binds to the DNA break connected to a polypeptide comprising a nucleic acid binding domain; and b) introducing into the cell a donor polynucleotide comprising i) a nucleotide sequence sufficiently complementary to hybridize to a sequence adjacent to the DNA break, and ii) a nucleotide sequence comprising a binding site recognized by the nucleic acid binding domain of the fusion protein, wherein the nucleic acid binding domain selectively binds to the binding site on the donor polynucleotide to produce a complex between the donor polynucleotide and the fusion protein, thereby recruiting the donor polynucleotide to the DNA break and promoting HDR.

Embodiment 60

The method of embodiment 59, wherein the protein that is recruited to the DNA break is an RNA-guided nuclease.

Embodiment 61

The method of embodiment 59, wherein the RNA-guided nuclease is a Cas nuclease or an engineered RNA-guided FokI-nuclease.

Embodiment 62

The method of embodiment 61, wherein the Cas nuclease is Cas9 or Cpf1.

Embodiment 63

The method of embodiment 59, wherein the DNA break is a single-stranded or double-stranded DNA break.

Embodiment 64

The method of embodiment 63, wherein the fusion protein comprises a protein that selectively binds to the single-stranded DNA break or the double-stranded DNA break.

Embodiment 65

The method of embodiment 59, wherein the donor polynucleotide is single-stranded or double-stranded.

Embodiment 66

The method of embodiment 59, wherein the nucleic acid binding domain is an RNA-binding domain and the binding site comprises an RNA sequence recognized by the RNA binding domain.

Embodiment 67

The method of embodiment 59, wherein the nucleic acid binding domain is a DNA-binding domain and the binding site comprises an DNA sequence recognized by the DNA binding domain.

Embodiment 68

The method of embodiment 67, wherein the DNA binding domain is a LexA DNA binding domain and the binding site is a LexA binding site.

Embodiment 69

The method of embodiment 67, wherein the DNA binding domain is a forkhead homolog 1 (FKH1) DNA binding domain and the binding site is a FKH1 binding site.

Embodiment 70

The method of embodiment 59, wherein the polypeptide comprising the nucleic acid binding domain further comprises a forkhead-associated (FHA) phosphothreonine-binding domain, wherein the donor polynucleotide is selectively recruited to a DNA break having a protein comprising a phosphorylated threonine residue located sufficiently close to the DNA break for the FHA phosphothreonine-binding domain to bind to the phosphorylated threonine residue.

Embodiment 71

The method of embodiment 59, wherein the polypeptide comprising the nucleic acid binding domain comprises a LexA DNA binding domain linked to a FHA phosphothreonine-binding domain.

Embodiment 72

The method of embodiment 59, wherein the donor polynucleotide is provided by a recombinant polynucleotide comprising a promoter operably linked to the donor polynucleotide.

Embodiment 73

The method of embodiment 59, wherein the fusion protein is provided by a recombinant polynucleotide comprising a promoter operably linked to a polynucleotide encoding the fusion protein.

Embodiment 74

The method of embodiment 59, wherein the donor polynucleotide and the fusion protein are provided by a single vector or multiple vectors.

Embodiment 75

The method of embodiment 74, wherein at least one vector is a viral vector or a plasmid.

Embodiment 76

The method of embodiment 50, wherein the donor polynucleotide is RNA or DNA.

Embodiment 77

The method of embodiment 76, further comprising reverse transcribing the donor polynucleotide comprising RNA with reverse transcriptase to produce a donor polynucleotide comprising DNA.

Embodiment 78

The method of embodiment 59, wherein the DNA break is created by a site-specific nuclease.

Embodiment 79

The method of embodiment 78, wherein the site-specific nuclease is selected from the group consisting of a Cas nuclease, an engineered RNA-guided FokI-nuclease, a meganuclease, a zinc finger nuclease (ZFN), and a transcription activator-like effector-based nuclease (TALEN).

Embodiment 80

A kit for multiplex genetic modification and barcoding of cells, the kit comprising: a) a plurality of recombinant polynucleotides, wherein each recombinant polynucleotide comprises a genome editing cassette comprising a polynucleotide encoding a guide RNA (gRNA) capable of hybridizing at a genomic target locus to be modified and a donor polynucleotide comprising a 5' homology arm that hybridizes to a 5' genomic target sequence and a 3' homology arm that hybridizes to a 3' genomic target sequence flanking a nucleotide sequence comprising an intended edit to be integrated into the genomic target locus, wherein each recombinant polynucleotide comprises a different genome editing cassette comprising a different guide RNA-donor polynucleotide combination, such that the plurality of recombinant polynucleotides is capable of producing a plurality of different intended edits at one or more genomic target loci; and b) an RNA-guided nuclease; and c) cells comprising a chromosomal barcode locus, wherein the barcode locus comprises a site for integration of the genome editing cassette of at least one recombinant polynucleotide.

Embodiment 81

The kit of embodiment 80, wherein each recombinant polynucleotide further comprises a pair of universal homology arms flanking the genome editing cassette that are capable of hybridizing to complementary sequences at the site for integration at the chromosomal barcode locus to allow said integration of the genome editing cassette at the chromosomal barcode locus by homology directed repair (HDR).

Embodiment 82

The kit of embodiment 81, wherein each recombinant polynucleotide further comprises a second guide RNA capable of hybridizing at the chromosomal barcode locus.

Embodiment 83

The kit of embodiment 80, further comprising a site-specific recombinase system.

Embodiment 84

The kit of embodiment 83, wherein the site-specific recombinase system is a Cre-loxP site-specific recombinase system, a Flp-FRT site-specific recombinase system, a PhiC31-att site-specific recombinase system, or a Dre-rox site-specific recombinase system.

Embodiment 85

The kit of embodiment 83, wherein the chromosomal barcode locus further comprises a first recombination target site for a site-specific recombinase and the recombinant polynucleotide further comprises a second recombination target site for the site-specific recombinase, such that site-specific recombination can occur between the first recombination target site and the second site-specific recombination site to allow said integration of the genome editing cassette at the chromosomal barcode locus.

Embodiment 86

The kit of embodiment 80, wherein the RNA-guided nuclease is a Cas nuclease or an engineered RNA-guided Fold-nuclease.

Embodiment 87

The kit of embodiment 86, wherein the Cas nuclease is Cas9 or Cpf1.

Embodiment 88

The kit of embodiment 80, further comprising a fusion protein comprising a polypeptide comprising a nucleic acid binding domain connected to a protein that selectively binds to a DNA break generated by the RNA-guided nuclease.

Embodiment 89

The kit of embodiment 88, wherein the donor polynucleotide further comprises a nucleotide sequence sufficiently complementary to hybridize to a sequence adjacent to the DNA break, and a nucleotide sequence comprising a binding site recognized by the nucleic acid binding domain of the fusion protein.

Embodiment 90

The kit of embodiment 89, wherein the nucleic acid binding domain is a LexA DNA binding domain and the binding site is a LexA binding site or nucleic acid binding domain is a forkhead homolog 1 (FKH1) DNA binding domain and the binding site is a FKH1 binding site.

Embodiment 91

The kit of embodiment 90, wherein the polypeptide comprising the nucleic acid binding domain further comprises a forkhead-associated (FHA) phosphothreonine-binding domain.

Embodiment 92

The kit of embodiment 91, wherein the polypeptide comprising the nucleic acid binding domain comprises a LexA DNA binding domain linked to a FHA phosphothreonine-binding domain.

While the preferred embodiments of the present disclosure have been illustrated and described, it will be appreciated that various changes can be made therein without departing from the spirit and scope of the disclosure.

What is claimed is:
1. A method for localizing a donor polynucleotide to a genomic target locus in a target cell, the method comprising:
(a) transfecting a target cell with a first recombinant polynucleotide, the first recombinant polynucleotide comprising a genome editing cassette comprising:
(i) a promoter operably linked to a nucleic acid sequence encoding a guide RNA (gRNA) capable of hybridizing at a genomic target locus to be modified, and
(ii) a donor polynucleotide comprising a sequence to be integrated into the genomic target locus;
(b) transfecting the target cell with a second recombinant polynucleotide that encodes a first polypeptide and encodes a second polypeptide, wherein:
(i) the first polypeptide is an RNA-guided nuclease, wherein the RNA-guided nuclease when complexed with the gRNA recognizes and creates a DNA break at the genomic target locus; and

(ii) the second polypeptide is a donor recruitment protein, wherein the donor recruitment protein comprises:
(1) a DNA binding domain that binds to the donor polynucleotide, and
(2) a DNA break site localizing domain that binds to a region near the DNA break at the genomic target locus;
wherein the donor recruitment protein when bound to both the region near the DNA break site and to the donor polynucleotide selectively recruits the donor polynucleotide to the DNA break site, thereby localizing the donor polynucleotide to the genomic target locus,
wherein the DNA binding domain comprises a LexA DNA binding domain and the DNA break site localizing domain comprises a forkhead-associated (FHA) phosphothreonine-binding domain or comprises a TP53BP1 domain.

2. The method of claim 1, wherein the RNA-guided nuclease modifies the genomic target locus by integrating the donor polynucleotide into the genomic target locus, thereby producing a genetically engineered cell.

3. The method of claim 1, wherein the genome editing cassette comprises a unique polynucleotide barcode or the donor polynucleotide comprises a unique polynucleotide barcode.

4. The method of claim 1, wherein the RNA-guided nuclease is a Cas nuclease or an engineered RNA-guided FokI-nuclease.

5. The method of claim 4, wherein the Cas nuclease is Cas9 or Cpf1.

6. The method of claim 1, wherein the donor recruitment protein exists independent of the first RNA-guided nuclease.

7. The method of claim 1, wherein the recruitment protein comprises a LexA DNA binding domain linked to the DNA break site localizing domain comprising an FHA phosphothreonine-binding domain.

8. The method of claim 1, wherein the first recombinant polynucleotide is circular and further comprises a second nucleic acid sequence encoding a second gRNA (guide X) capable of hybridizing with the first recombinant polynucleotide, wherein the guide X forms a complex with a nuclease in each cell such that the guide X-nuclease complex cleaves the first recombinant polynucleotide.

9. The method of 2, wherein the genetically engineered cell is a genetically engineered therapeutic cell.

10. The method of 9, wherein the genetically engineered therapeutic cell is a genetically engineered immune cell.

11. The method of 10, wherein the genetically engineered immune cell is a T cell or a natural killer cell that targets a cancer.

12. The method of claim 3, wherein the target cell is modified to harbor a barcode integration locus for integration of the unique polynucleotide barcode.

13. A kit comprising the first recombinant polynucleotide and the second recombinant polynucleotide used in the method of claim 1.

14. A method for localizing a donor polynucleotide to a genomic target locus in a target cell, the method comprising:
(a) transfecting a target cell with a first recombinant polynucleotide, the first recombinant polynucleotide comprising a genome editing cassette comprising:
(i) a promoter operably linked to a nucleic acid sequence encoding a guide RNA (gRNA) capable of hybridizing at a genomic target locus to be modified, and
(ii) a donor polynucleotide comprising a sequence to be integrated into the genomic target locus;
(b) transfecting the target cell with a second recombinant polynucleotide that encodes a first polypeptide and encodes a second polypeptide, wherein:
(i) the first polypeptide is an RNA-guided nuclease, wherein the RNA-guided nuclease when complexed with the gRNA recognizes and creates a DNA break site at the genomic target locus; and
(ii) the second polypeptide is a donor recruitment protein, wherein the donor recruitment protein comprises:
(1) a DNA binding domain that binds to the donor polynucleotide, and
(2) a DNA break site localizing domain that binds to a region near the DNA break at the genomic target locus;
wherein the donor recruitment protein when bound to both the region near the DNA break site and to the donor polynucleotide selectively recruits the donor polynucleotide to the DNA break site, thereby localizing the donor polynucleotide to the genomic target locus; and
wherein the genome editing cassette comprises a unique polynucleotide barcode or the donor polynucleotide comprises a unique polynucleotide barcode.

15. A method for localizing a donor polynucleotide to a genomic target locus in a target cell, the method comprising:
(a) transfecting a target cell with a first recombinant polynucleotide, the first recombinant polynucleotide comprising a genome editing cassette comprising:
(i) a promoter operably linked to a nucleic acid sequence encoding a guide RNA (gRNA) capable of hybridizing at a genomic target locus to be modified, and
(ii) a donor polynucleotide comprising a sequence to be integrated into the genomic target locus;
(b) transfecting the target cell with a second recombinant polynucleotide that encodes a first polypeptide and encodes a second polypeptide, wherein:
(i) the first polypeptide is an RNA-guided nuclease, wherein the RNA-guided nuclease when complexed with the gRNA recognizes and creates a DNA break site at the genomic target locus; and
(ii) the second polypeptide is a donor recruitment protein, wherein the donor recruitment protein comprises:
(1) a DNA binding domain that binds to the donor polynucleotide, and
(2) a DNA break site localizing domain that binds to a region near the DNA break at the genomic target locus;
wherein the donor recruitment protein when bound to both the region near the DNA break site and to the donor polynucleotide selectively recruits the donor polynucleotide to the DNA break site, thereby localizing the donor polynucleotide to the genomic target locus; and
wherein the first recombinant polynucleotide is circular and further comprises a second nucleic acid sequence encoding a second gRNA (guide X) capable of hybridizing with the first recombinant polynucleotide, wherein the guide X forms a complex with a nuclease in each cell such that the guide X-nuclease complex cleaves the first recombinant polynucleotide.

* * * * *

UNITED STATES PATENT AND TRADEMARK OFFICE
CERTIFICATE OF CORRECTION

| | | |
|---|---|---|
| PATENT NO. | : 12,416,015 B2 | Page 1 of 1 |
| APPLICATION NO. | : 16/646999 | |
| DATED | : September 16, 2025 | |
| INVENTOR(S) | : Kevin Roy et al. | |

It is certified that error appears in the above-identified patent and that said Letters Patent is hereby corrected as shown below:

In the Specification

At Column 1, the paragraph following the sub-heading "STATEMENT REGARDING FEDERALLY SPONSORED RESEARCH OR DEVELOPMENT" should be changed as follows:
Delete:
"This invention was made with government support under contract HG000205 awarded by the National Institutes of Health and contract 70NANB15H268 awarded by the National Institute of Standards and Technology. The government has certain rights in the invention."
And insert:
--This invention was made with Government support under contract 70NANB15H268 awarded by the National Institute of Standards & Technology and under contracts GM020056 and HG000205 awarded by the National Institutes of Health. The Government has certain rights in the invention.--

Signed and Sealed this
Fourteenth Day of October, 2025

John A. Squires
*Director of the United States Patent and Trademark Office*